US010085985B2

(12) United States Patent
Bogdan et al.

(10) Patent No.: US 10,085,985 B2
(45) Date of Patent: *Oct. 2, 2018

(54) BROMODOMAIN INHIBITORS

(71) Applicant: AbbVie Inc., North Chicago, IL (US)

(72) Inventors: Andrew Bogdan, Evanston, IL (US); Warren M. Kati, Gurnee, IL (US); Keith F. McDaniel, Wauconda, IL (US); Chang H. Park, Wadsworth, IL (US); George S. Sheppard, Wilmette, IL (US); Le Wang, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/216,855

(22) Filed: Jul. 22, 2016

(65) Prior Publication Data

US 2016/0331749 A1 Nov. 17, 2016

Related U.S. Application Data

(62) Division of application No. 14/564,352, filed on Dec. 9, 2014, now Pat. No. 9,428,514.

(30) Foreign Application Priority Data

Dec. 9, 2013 (WO) ................ PCT/CN2013/088844

(51) Int. Cl.
| | |
|---|---|
| *A61K 31/506* | (2006.01) |
| *C07D 487/04* | (2006.01) |
| *C07D 211/86* | (2006.01) |
| *C07D 405/04* | (2006.01) |
| *C07D 401/04* | (2006.01) |
| *C07D 417/04* | (2006.01) |
| *C07D 401/12* | (2006.01) |
| *C07D 405/12* | (2006.01) |
| *C07D 413/12* | (2006.01) |
| *C07D 417/12* | (2006.01) |
| *C07D 213/69* | (2006.01) |
| *A61K 31/4412* | (2006.01) |
| *A61K 31/4433* | (2006.01) |
| *A61K 31/4439* | (2006.01) |
| *A61K 31/444* | (2006.01) |
| *A61K 31/4709* | (2006.01) |
| *A61K 31/497* | (2006.01) |

(52) U.S. Cl.
CPC .......... *A61K 31/506* (2013.01); *A61K 31/444* (2013.01); *A61K 31/4412* (2013.01); *A61K 31/4433* (2013.01); *A61K 31/4439* (2013.01); *A61K 31/4709* (2013.01); *A61K 31/497* (2013.01); *C07D 211/86* (2013.01); *C07D 213/69* (2013.01); *C07D 401/04* (2013.01); *C07D 401/12* (2013.01); *C07D 405/04* (2013.01); *C07D 405/12* (2013.01); *C07D 413/12* (2013.01); *C07D 417/04* (2013.01); *C07D 417/12* (2013.01); *C07D 487/04* (2013.01)

(58) Field of Classification Search
CPC ...................................................... A61K 31/506
USPC ........................................................ 546/294
See application file for complete search history.

(56) References Cited

U.S. PATENT DOCUMENTS 9,561,231 B2 * 2/2017 Hubbard .............. A61K 31/541

OTHER PUBLICATIONS

Freshney (Culture of Animal Cells, A Manual of Basic Technique, Alan R. Liss, Inc., 1983, New York, p.*
Venkatesh et al., J. Pharm. Sci. 89, 145-54 (2000) (p. 146, left column).*
Sporn et al. The American Journal of Medicine, Jun. 1981, 70(6), 1231-1236.*
Cecil Textbook of Medicine, 20th ed. J.C. Bennett. Philadelphia: WB Saunders Co., 1996.*
Herrmann, et al., "Small-molecule inhibition of BRD4 as a new potent approach to eliminate leukemic stem- and progenitor cells in acute myeloid leukemia (AML) ", Oncotarget, 2012 3:1588-1599.
Wyce, et al. "Inhibition of BET bromodomain proteins as a therapeutic approach in prostate cancer", Oncotarget 2013; 4.

* cited by examiner

*Primary Examiner* — Nizal S Chandrakumar
(74) *Attorney, Agent, or Firm* — Michael S. Montgomery

(57) ABSTRACT

The present invention provides for compounds of formula (I)

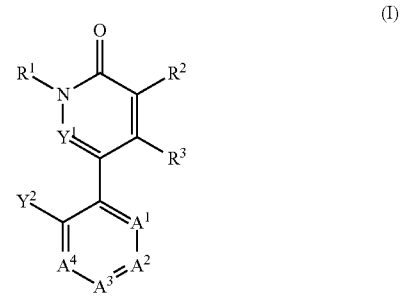

wherein $Y^1$, $Y^2$, $R^1$, $R^2$, $R^3$, $A^1$, $A^2$, $A^3$, and $A^4$, have any of the values defined in the specification, and pharmaceutically acceptable salts thereof, that are useful as agents for the treatment of diseases and conditions, including inflammatory diseases, cancer, and AIDS. Also provided are pharmaceutical compositions comprised of one or more compounds of formula (I).

21 Claims, No Drawings

BROMODOMAIN INHIBITORS

This application is a divisional of U.S. application Ser. No. 14/564,352, filed Dec. 9, 2014, which claims the benefit of International Patent Application No. PCT/CN2013/088844, filed Dec. 9, 2013, which are incorporated by reference in their entirety.

BACKGROUND

Bromodomains refer to conserved protein structural folds which bind to N-acetylated lysine residues that are found in some proteins. The BET family of bromodomain containing proteins is comprised of four members (BRD2, BRD3, BRD4 and BRDt). Each member of the BET family employs two bromodomains to recognize N-acetylated lysine residues found primarily, but not exclusively, on the amino-terminal tails of histone proteins. These interactions modulate gene expression by recruiting transcription factors to specific genome locations within chromatin. For example, histone-bound BRD4 recruits the transcription factor P-TEFb to promoters, resulting in the expression of a subset of genes involved in cell cycle progression (Yang et al., Mol. Cell. Biol. 28: 967-976 (2008)). BRD2 and BRD3 also function as transcriptional regulators of growth promoting genes (LeRoy et al., Mol. Cell 30: 51-60 (2008)). BET family members were recently established as being important for the maintenance of several cancer types (Zuber et al., Nature 478: 524-528 (2011); Mertz et al; Proc. Nat'l. Acad. Sci. 108: 16669-16674 (2011); Delmore et al., Cell 146: 1-14, (2011); Dawson et al., Nature 478: 529-533 (2011)). BET family members have also been implicated in mediating acute inflammatory responses through the canonical NF-KB pathway (Huang et al., Mol. Cell. Biol. 29: 1375-1387 (2009)) resulting in the upregulation of genes associated with the production of cytokines (Nicodeme et al., Nature 468: 1119-1123, (2010)). Suppression of cytokine induction by BET bromodomain inhibitors has been shown to be an effective approach to treat inflammation-mediated kidney disease in an animal model (Zhang, et al., J. Biol. Chem. 287: 28840-28851 (2012)). BRD2 function has been linked to predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). BET bromodomain inhibitors have also been shown to reactivate HIV transcription in models of latent T cell infection and latent monocyte infection (Banerjee, et al, J. Leukocyte Biol. doi:10.1189/j1b.0312165). BRDt has an important role in spermatogenesis that is blocked by BET bromodomain inhibitors (Matzuk, et al., Cell 150: 673-684 (2012)). Thus, compounds that inhibit the binding of BET family bromodomains to their cognate acetylated lysine proteins are being pursued for the treatment of cancer, inflammatory diseases, kidney diseases, diseases involving metabolism or fat accumulation, and some viral infections, as well as for providing a method for male contraception. Accordingly, there is an ongoing medical need to develop new drugs to treat these indications.

SUMMARY

In one aspect the present invention provides for compounds of formula (I) or pharmaceutically acceptable salts thereof,

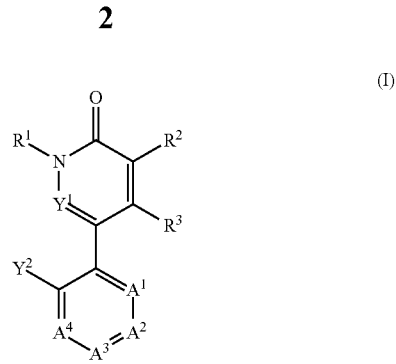

(I)

wherein
$R^1$ is $C_1$-$C_3$ alkyl or $C_1$-$C_3$ haloalkyl;
$R^2$ is H;
$R^3$ is —O—$C_1$-$C_6$ alkyl, —OCD$_2$CH$_3$, or —OCD$_2$CD$_3$;
$Y^1$ is N or CR$^4$, wherein R$^4$ is H, $C_1$-$C_3$ alkyl, or $C_1$-$C_3$ haloalkyl;
$A^2$ is CR$^5$, and A$^1$, A$^3$, and A$^4$ are CR$^6$; or
$A^2$ is CR$^5$, A$^1$ and A$^3$ are CR$^6$, and A$^4$ is N;
$R^5$ is —N(R$^{5d}$)—$C_1$-$C_6$ alkylenyl-R$^{5a}$, —N(R$^{5d}$)C(O)—$C_1$-$C_6$ alkylenyl-R$^{5b}$, —N(R$^{5d}$)SO$_2$—$C_1$-$C_6$ alkylenyl-R$^{5c}$, —N(R$^{5d}$)C(O)N(R$^{5d}$)-G$^1$, —N(R$^{5d}$)C(O)N(R$^{5d}$)—$C_1$-$C_6$ alkylenyl-R$^{5a}$, —N(R$^{5d}$)SO$_2$N(R$^{5d}$)—$C_1$-$C_6$ alkylenyl-R$^{5a}$, —C(O)N(R$^{5d}$)—$C_1$-$C_6$ alkylenyl-R$^{5a}$, or —SO$_2$N(R$^{5d}$)—$C_1$-$C_6$ alkylenyl-R$^{5a}$, wherein
$R^{5a}$, at each occurrence, is independently G$^1$, —OR$^{5aa}$, —OC(O)R$^{5dd}$, —SR$^{5aa}$, —S(O)R$^{5aa}$, —SO$_2$R$^{5aa}$, —SO$_2$NR$^{5bb}$R$^{5cc}$, —NR$^{5bb}$R$^{5cc}$, —NR$^{5bb}$C(O)R$^{5dd}$, —NR$^{5bb}$SO$_2$R$^{5dd}$, —NR$^{5bb}$C(O)OR$^{5dd}$, —NR$^{5bb}$C(O)NR$^{5bb}$R$^{5cc}$, —NR$^{5bb}$SO$_2$NR$^{5bb}$R$^{5cc}$, —C(O)R$^{5aa}$, —C(O)OR$^{5aa}$, or —C(O)NR$^{5bb}$R$^{5cc}$,
$R^{5b}$ is G$^1$, —OR$^{5aa}$, —OC(O)R$^{5dd}$, —SR$^{5aa}$, —S(O)R$^{5aa}$, —SO$_2$R$^{5aa}$, —SO$_2$NR$^{5bb}$R$^{5cc}$, —N(R$^{5bb}$)(G$^1$), —NR$^{5bb}$—(C$_1$-C$_6$ alkylenyl)-G$^1$, —NR$^{5bb}$C(O)R$^{5dd}$, —NR$^{5bb}$SO$_2$R$^{5dd}$, —NR$^{5bb}$C(O)OG$^1$, —NR$^{5bb}$C(O)O—(C$_1$-C$_6$ alkylenyl)-G$^1$, —NR$^{5bb}$C(O)NR$^{5bb}$R$^{5cc}$, —NR$^{5bb}$SO$_2$NR$^{5bb}$R$^{5cc}$, —C(O)R$^{5aa}$, —C(O)OR$^{5aa}$, or —C(O)NR$^{5bb}$R$^{5cc}$,
$R^{5c}$ is —OR$^{5aa}$, —OC(O)R$^{5dd}$, —SR$^{5aa}$, —S(O)R$^{5aa}$, —SO$_2$R$^{5aa}$, —SO$_2$NR$^{5bb}$R$^{5cc}$, —NR$^{5bb}$R$^{5cc}$, —NR$^{5bb}$C(O)R$^{5dd}$, —NR$^{5bb}$SO$_2$R$^{5dd}$, —NR$^{5bb}$C(O)OR$^{5dd}$, —NR$^{5bb}$C(O)NR$^{5bb}$R$^{5cc}$, —NR$^{5bb}$SO$_2$NR$^{5bb}$R$^{5cc}$, —C(O)R$^{5aa}$, —C(O)OG$^1$, —C(O)O—(C$_1$-C$_6$ alkylenyl)-G$^1$, or —C(O)NR$^{5bb}$R$^{5cc}$,
$R^{5d}$, at each occurrence, is independently H, $C_1$-$C_6$ alkyl, $C_2$-$C_6$ alkenyl, $C_2$-$C_6$ alkynyl, $C_1$-$C_6$ haloalkyl, G$^1$, —OR$^{5aa}$, —OC(O)R$^{5dd}$, —SR$^{5aa}$, —S(O)R$^{5aa}$, —SO$_2$R$^{5aa}$, —SO$_2$NR$^{5bb}$R$^{5cc}$, —NR$^{5bb}$R$^{5cc}$, —NR$^{5bb}$C(O)R$^{5dd}$, —NR$^{5bb}$SO$_2$R$^{5dd}$, —NR$^{5bb}$C(O)OR$^{5dd}$, —NR$^{5bb}$C(O)NR$^{5bb}$R$^{5cc}$, —NR$^{5bb}$SO$_2$NR$^{5bb}$R$^{5cc}$, —C(O)R$^{5aa}$, —C(O)OR$^{5aa}$, —C(O)NR$^{5bb}$R$^{5cc}$, —(C$_1$-C$_6$ alkylenyl)-G$^1$, —(C$_1$-C$_6$ alkylenyl)-OR$^{5aa}$, —(C$_1$-C$_6$ alkylenyl)-OC(O)R$^{5dd}$, —(C$_1$-C$_6$ alkylenyl)-SR$^{5aa}$, —(C$_1$-C$_6$ alkylenyl)-S(O)R$^{5aa}$, —(C$_1$-C$_6$ alkylenyl)-SO$_2$R$^{5aa}$, —(C$_1$-C$_6$ alkylenyl)-SO$_2$NR$^{5bb}$R$^{5cc}$, —(C$_1$-C$_6$ alkylenyl)-NR$^{5bb}$R$^{5cc}$, —(C$_1$-C$_6$ alkylenyl)-NR$^{5bb}$C(O)R$^{5dd}$, —(C$_1$-C$_6$ alkylenyl)-NR$^{5bb}$SO$_2$R$^{5dd}$, —(C$_1$-C$_6$ alkylenyl)-NR$^{5bb}$C(O)OR$^{5dd}$, —(C$_1$-C$_6$ alkylenyl)-NR$^{5bb}$C(O)NR$^{5bb}$R$^{5cc}$, —(C$_1$-C$_6$ alkylenyl)-NR$^{5bb}$SO$_2$NR$^{5bb}$R$^{5cc}$, —(C$_1$-C$_6$ alkylenyl)-C(O)

$R^{5aa}$, —($C_1$-$C_6$ alkylenyl)-C(O)O$R^{5aa}$, or —($C_1$-$C_6$ alkylenyl)-C(O)N$R^{5bb}R^{5cc}$;

$R^6$ is H, $C_1$-$C_6$ alkyl, halogen, $C_1$-$C_6$ haloalkyl, or —CN;

$R^{5aa}$, $R^{5bb}$, and $R^{5cc}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^1$, or —($C_1$-$C_6$ alkylenyl)-$G^1$;

$R^{5dd}$, at each occurrence, is independently $C_1$-$C_6$ alkyl, $C_2$-$C_6$ alkenyl, $C_2$-$C_6$ alkynyl, $C_1$-$C_6$ haloalkyl, $G^1$, or —($C_1$-$C_6$ alkylenyl)-$G^1$;

$G^1$, at each occurrence, is independently aryl, heteroaryl, heterocycle, cycloalkyl, or cycloalkenyl, each of which is optionally substituted with 1, 2, 3, 4, or 5 $R^{1g}$ groups, $Y^2$ is -L-$G^2$; wherein
L is O or N($R^x$) wherein $R^x$ is H or $C_1$-$C_6$ alkyl;
$G^2$ is aryl, heteroaryl, heterocycle, cycloalkyl, or cycloalkenyl, each of which is optionally substituted with 1, 2, 3, 4, or 5 $R^{2g}$ groups, $R^{1g}$ and $R^{2g}$, at each occurrence, are each independently oxo, $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{z1}$, —OC(O)$R^{z2}$, —OC(O)N$R^{z3}R^{z4}$, —$SR^{z1}$, —S(O)$_2R^{z1}$, —S(O)$_2$N$R^{z3}R^{z4}$, —C(O)$R^{z1}$, —C(O)$R^{z1}$, —C(O)N$R^{z3}R^{z4}$, —N$R^{z3}R^{z4}$, —N($R^{z3}$)C(O)$R^{z2}$, —N($R^{z3}$)S(O)$_2R^{z2}$, —N($R^{z3}$)C(O)O($R^{z2}$), —N($R^{z3}$)C(O)N$R^{z3}R^{z4}$, —N($R^{z3}$)S(O)$_2$N$R^{z3}R^{z4}$, $G^3$, —($C_1$-$C_6$ alkylenyl)-CN, —($C_1$-$C_6$ alkylenyl)-$OR^{z1}$, —($C_1$-$C_6$ alkylenyl)-OC(O)$R^{z2}$, —($C_1$-$C_6$ alkylenyl)-OC(O)N$R^{z3}R^{z4}$, —($C_1$-$C_6$ alkylenyl)-S(O)$_2R^{z1}$, —($C_1$-$C_6$ alkylenyl)-S(O)$_2$N$R^{z3}R^{z4}$, —($C_1$-$C_6$ alkylenyl)-C(O)$R^{z1}$, —($C_1$-$C_6$ alkylenyl)-C(O)O$R^{z1}$, —($C_1$-$C_6$ alkylenyl)-C(O)N$R^{z3}R^{z4}$, —($C_1$-$C_6$ alkylenyl)-N$R^{z3}R^{z4}$, —($C_1$-$C_6$ alkylenyl)-N($R^{z3}$)C(O)$R^{z2}$, —($C_1$-$C_6$ alkylenyl)-N($R^{z3}$)S(O)$_2R^{z2}$, —($C_1$-$C_6$ alkylenyl)-N($R^{z3}$)C(O)O($R^{z2}$), —($C_1$-$C_6$ alkylenyl)-N($R^{z3}$)C(O)N$R^{z3}R^{z4}$, —($C_1$-$C_6$ alkylenyl)-N($R^{z3}$)S(O)$_2$N$R^{z3}R^{z4}$, —($C_1$-$C_6$ alkylenyl)-CN, or —($C_1$-$C_6$ alkylenyl)-$G^3$;

$R^{z1}$, $R^{z3}$, and $R^{z4}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^3$, or —$C_1$-$C_6$ alkylenyl-$G^3$;

$R^{z2}$, at each occurrence, is independently $C_1$-$C_6$ alkyl, $C_2$-$C_6$ alkenyl, $C_2$-$C_6$ alkynyl, $C_1$-$C_6$ haloalkyl, $G^3$, or —$C_1$-$C_6$ alkylenyl-$G^3$;

$G^3$ is aryl, heteroaryl, heterocycle, cycloalkyl, or cycloalkenyl, each of which is optionally substituted with 1, 2, 3, 4, or 5 $R^{3g}$ groups, $R^{3g}$, at each occurrence, is independently oxo, $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^a$, —OC(O)$R^b$, —OC(O)N$R^cR^d$, —$SR^a$, —S(O)$_2R^a$, —S(O)$_2$N$R^cR^d$, —C(O)$R^a$, —C(O)O$R^a$, —C(O)N$R^cR^d$, —N$R^cR^d$, —N($R^c$)C(O)$R^b$, —N($R^c$)S(O)$_2R^b$, —N($R^c$)C(O)O($R^b$), —N($R^c$)C(O)N$R^cR^d$, —N($R^c$)S(O)$_2$N$R^cR^d$, —($C_1$-$C_6$ alkylenyl)-CN, —($C_1$-$C_6$ alkylenyl)-$OR^a$, —($C_1$-$C_6$ alkylenyl)-OC(O)$R^b$, —($C_1$-$C_6$ alkylenyl)-OC(O)N$R^cR^d$, —($C_1$-$C_6$ alkylenyl)-S(O)$_2R^a$, —($C_1$-$C_6$ alkylenyl)-S(O)$_2$N$R^cR^d$, —($C_1$-$C_6$ alkylenyl)-C(O)$R^a$, —($C_1$-$C_6$ alkylenyl)-C(O)O$R^a$, —($C_1$-$C_6$ alkylenyl)-C(O)N$R^cR^d$, —($C_1$-$C_6$ alkylenyl)-N$R^cR^d$, —($C_1$-$C_6$ alkylenyl)-N($R^c$)C(O)$R^b$, —($C_1$-$C_6$ alkylenyl)-N($R^c$)S(O)$_2R^b$, —($C_1$-$C_6$ alkylenyl)-N($R^c$)C(O)O($R^b$), ($C_1$-$C_6$ alkylenyl)-N($R^c$)C(O)N$R^cR^d$, —($C_1$-$C_6$ alkylenyl)-N($R^c$)S(O)$_2$N$R^cR^d$, or —($C_1$-$C_6$ alkylenyl)-CN;

$R^a$, $R^c$, and $R^d$, at each occurrence, are each independently H, $C_1$-$C_6$ alkyl, $C_2$-$C_6$ alkenyl, $C_2$-$C_6$ alkynyl, or $C_1$-$C_6$ haloalkyl, and $R^b$, at each occurrence, is independently $C_1$-$C_6$ alkyl, $C_2$-$C_6$ alkenyl, $C_2$-$C_6$ alkynyl, or $C_1$-$C_6$ haloalkyl.

In another aspect, the present invention provides for methods for treating or preventing disorders that are ameliorated by inhibition of BET. Such methods comprise of administering to the subject a therapeutically effective amount of a compound of formula (I), or a pharmaceutically acceptable salt thereof, alone, or in combination with a pharmaceutically acceptable carrier.

Some of the methods are directed to treating or preventing an inflammatory disease or cancer or AIDS.

In another aspect, the present invention relates to methods of treating cancer in a subject comprising administering a therapeutically effective amount of a compound of formula (I) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor. In certain embodiments, the methods further comprise administering a therapeutically effective amount of at least one additional therapeutic agent. In certain embodiments, the additional therapeutic agent is selected from the group consisting of cytarabine, bortezomib, and 5-azacitidine.

In another aspect, the present invention relates to methods of treating a disease or condition in a subject comprising administering a therapeutically effective amount of a compound of formula (I) or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, cardiac myopathy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of formula (I) or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of formula (I) or a pharmaceutically acceptable salt thereof, to a subject in need thereof, wherein said acute kidney injury or disease or condition is selected from the group consisting of: ischemia-reperfusion induced, cardiac and major surgery induced, percutaneous coronary intervention induced, radio-contrast agent induced, sepsis induced, pneumonia induced, and drug toxicity induced. In certain embodiments, the methods further comprise administering a therapeutically effective amount of at least one additional therapeutic agent.

In another aspect, the present invention relates to methods of treating AIDS in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of preventing conception by inhibiting spermatogenesis in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

A further aspect of the invention provides the use of a compound of formula (I), alone or in combination with at least one additional therapeutic agent, in the manufacture of a medicament for treating or preventing conditions and disorders disclosed herein, and with or without a pharmaceutically acceptable carrier.

Pharmaceutical compositions comprising a compound of formula (I), or a pharmaceutically acceptable salt, alone or in combination with at least one additional therapeutic agent, are also provided.

DETAILED DESCRIPTION

Disclosed herein are compounds of formula (I)

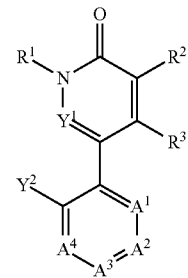

(I)

wherein $Y^1$, $Y^2$, $R^1$, $R^2$, $R^3$, $A^1$, $A^2$, $A^3$, and $A^4$ are defined above in the Summary of the Invention and below in the Detailed Description. Further, compositions comprising such compounds and methods for treating conditions and disorders using such compounds and compositions are also disclosed.

Compounds disclosed herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more optional pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_6$ alkenyl" means an alkenyl group containing 2-6 carbon atoms. Non-limiting examples of alkenyl include buta-1,3-dienyl, ethenyl, 2-propenyl, 2-methyl-2-propenyl, 3-butenyl, 4-pentenyl, and 5-hexenyl.

The term "$C_2$-$C_6$ alkenylene" means a divalent group derived from a straight or branched chain hydrocarbon of 2 to 6 carbon atoms and contains at least one carbon-carbon double bond. Representative examples of $C_2$-$C_6$ alkenylene include, but are not limited to, —CH═CH— and —CH$_2$CH═CH—.

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" refers to an alkyl substituent containing from 1 to 6 carbon atoms and "$C_1$-$C_3$ alkyl" refers to an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms ($C_1$-$C_4$ alkylenyl) or of 1 to 3 carbon atoms ($C_1$-$C_3$ alkylenyl) or of 2 to 6 carbon atoms ($C_2$-$C_6$ alkylenyl). Examples of alkylene and alkylenyl include, but are not limited to, —CH$_2$—, —CH$_2$CH$_2$—, —C(CH$_3$)$_2$— CH$_2$CH$_2$CH$_2$—, —CH$_2$CH$_2$CH$_2$CH$_2$—, and —CH$_2$CH (CH$_3$)CH$_2$—.

The term "$C_2$-$C_6$ alkynyl" as used herein, means a straight or branched chain hydrocarbon radical containing from 2 to 6 carbon atoms and containing at least one carbon-carbon triple bond. Representative examples of $C_2$-$C_6$ alkynyl include, but are not limited, to acetylenyl, 1-propynyl, 2-propynyl, 3-butynyl, 2-pentynyl, and 1-butynyl.

The term "$C_2$-$C_6$ alkynylene" means a divalent group derived from a straight or branched chain hydrocarbon of from 2 to 6 carbon atoms containing at least one triple bond. Representative examples of alkynylene include, but are not limited to, —C≡C—, —CH$_2$C≡C—, —CH(CH$_3$)CH$_2$C≡C—, —C≡CCH$_2$—, and —C≡CCH(CH$_3$)CH$_2$—.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl, indenyl, naphthyl, dihydronaphthalenyl, and tetrahydronaphthalenyl. The bicyclic aryls are attached to the parent molecular moiety through any carbon atom contained within the bicyclic ring systems.

The term "cycloalkyl" as used herein, refers to a radical that is a monocyclic cyclic alkyl, a bicyclic cycloalkyl, or a spiro cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic and the bicyclic cycloalkyl groups may contain one or two alkylene bridges, each consisting of one, two, three, or four carbon atoms in length, and each bridge links two non-adjacent carbon atoms of the ring system. Non-limiting examples of bicyclic ring systems include bicyclo[3.1.1]heptane, bicyclo[2.2.1]heptane, bicyclo[2.2.2]octane, bicyclo[3.2.2]nonane, bicyclo[3.3.1] nonane, and bicyclo[4.2.1]nonane, tricyclo[3.3.1.0$^{3,7}$] nonane (octahydro-2,5-methanopentalene or noradamantane), and tricyclo[3.3.1.1$^{3,7}$]decane (adamantane). A spiro cycloalkyl is a monocyclic cycloalkyl wherein two substituents on the same carbon atom of the monocyclic cycloalkyl ring together with said carbon atom form a second monocyclic cycloalkyl ring. The monocyclic, the bicyclic, and the spiro cycloalkyl groups are attached to the parent molecular moiety through any substitutable atom contained within the ring system.

The term "$C_3$-$C_6$ cycloalkyl" as used herein, means cyclopropyl, cyclobutyl, cyclopentyl, and cyclohexyl.

The term "cycloalkenyl" as used herein, refers to a monocyclic or a bicyclic hydrocarbon ring radical. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, or three carbon atoms, and each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyls can be attached to the parent molecular moiety through any substitutable atom contained within the ring systems.

The term "$C_5$-$C_8$ cycloalkenyl" as used herein, means a cyclohexenyl, cyclohexadienyl, cyclopentenyl, cycloheptenyl, and cyclooctenyl. The $C_5$-$C_8$ cycloalkenyls can be attached to the parent molecular moiety through any substitutable atom contained within the ring systems.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, or six hydrogen atoms are replaced by halogen. The term "$C_1$-$C_3$ haloalkyl" means a $C_1$-$C_3$ alkyl group, as defined herein, in which one, two, or three hydrogen atoms are replaced by halogen. Representative examples of haloalkyl include, but are not limited to, chloromethyl, 2-fluoroethyl, 2,2-difluoroethyl, 2,2,2-trifluoroethyl, trifluoromethyl, difluoromethyl, pentafluoroethyl, 2-chloro-3-fluoropentyl, trifluorobutyl, and trifluoropropyl.

The term "heterocycle" or "heterocyclic" as used herein, means a radical of a monocyclic heterocycle, a bicyclic heterocycle, and a spiro heterocycle. A monocyclic heterocycle is a three-, four-, five-, six-, seven-, or eight-membered carbocyclic ring also containing at least one heteroatom independently selected from the group consisting of O, N, and S. A three- or four-membered ring contains zero or one double bond, and one heteroatom selected from the group consisting of O, N, and S. When two O atoms or one O atom and one S atom are present in a heterocyclic ring, then the two O atoms or one O atom and one S atom are not bonded directly to each other. A five-membered ring contains zero or one double bond and one, two, or three heteroatoms selected from the group consisting of O, N, and S. Examples of five-membered heterocyclic rings include those containing in the ring: 1 O; 1 S; 1 N; 2 N; 3 N; 1 S and 1 N; 1 S, and 2 N; 1 O and 1 N; or 1 O and 2 N. Examples of 5-membered heterocyclic groups include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl. A six-membered ring contains zero, one, or two double bonds and one, two, or three heteroatoms selected from the group consisting of O, N, and S. Examples of six-membered heterocyclic rings include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 Q and 1 N; and 1 O and 2 N. Examples of 6-membered heterocyclic groups include tetrahydropyranyl, dihydropyranyl, 1,4-dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydropyranyl, tetrahydrothiopyranyl, 1,1-dioxo-hexahydro-1-thiopyranyl, 1,1-dioxo-1$\lambda^6$-thiomorpholinyl, thiomorpholinyl, thioxanyl, and trithianyl. Seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,4-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, benzopyranyl, benzothiopyranyl, 2,3-dihydrobenzofuranyl, 2,3-dihydrobenzothienyl, 3,4-dihydro-2H-chromen-6-yl, 2,3-dihydro-1H-indolyl, 3,4-dihydroisoquinolin-2(1H)-yl, 2,3,4,6-tetrahydro-1H-pyrido[1,2-a]pyrazin-2-yl, and hexahydropyrano[3,4-b][1,4]oxazin-1(5H)-yl. The monocyclic heterocycle and the bicyclic heterocycle may contain one or two alkylene bridges or an alkenylene bridge, or mixture thereof, each consisting of no more than four carbon atoms and each linking two non adjacent atoms of the ring system. Examples of such bridged heterocycle include, but are not limited to, azabicyclo[2.2.1]heptyl (including 2-azabicyclo [2.2.1]hept-2-yl), 8-azabicyclo[3.2.1]oct-8-yl, octahydro-2, 5-epoxypentalene, hexahydro-2H-2,5-methanocyclopenta [b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). A spiro heterocycle is a monocyclic heterocycle wherein two substituents on the same carbon atom of the monocyclic heterocycle ring together with said carbon atom form a second ring system selected from a monocyclic cycloalkyl, a bicyclic cycloalkyl, a monocyclic heterocycle, or a bicyclic heterocycle. Examples of spiro heterocycle include, but not limited to, 6-azaspiro[2.5]oct-6-yl, 1'H, 4H-spiro[1,3-benzodioxine-2,4'-piperidin]-1'-yl, 1'H, 3H-spiro[2-benzofuran-1,4'-piperidin]-1'-yl, and 1,4-dioxa-8-azaspiro[4.5]dec-8-yl. The monocyclic, the bicyclic, and the Spiro heterocycles can be unsubstituted or substituted. The monocyclic, the bicyclic and the Spiro heterocycles are connected to the parent molecular moiety through any carbon atom or any nitrogen atom contained within the ring systems. The nitrogen and sulfur heteroatoms in the heterocycle rings may optionally be oxidized (e.g. 1,1-dioxidotetrahydrothienyl, 1,1-dioxido-1,2-thiazolidinyl, 1,1-dioxidothiomorpholinyl)) and the nitrogen atoms may optionally be quarternized.

The term "$C_4$-$C_6$ heterocycle" as used herein, means a 4-, 5-, or 6-membered monocyclic heterocyclic ring as described above. Examples of $C_4$-$C_6$ heterocycle include azetidinyl, oxetanyl, pyrrolidinyl, tetrahydrofuranyl, and tetrahydropyranyl.

The term "heteroaryl" as used herein, means a monocyclic heteroaryl and a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, phthalazinyl, 2,6-dihydropyrrolo[3,4-c] pyrazol-5(4H)-yl, 6,7-dihydro-5H-pyrrolo[1,2-a]imidazol-2-yl, 6,7-dihydro-pyrazolo[1,5-a]pyrazin-5(4H)-yl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups are connected to the parent molecular moiety through any substitutable carbon atom or any substitutable nitrogen atom contained within the ring systems. The nitrogen atom in the heteroaryl rings may optionally be oxidized and may optionally be quarternized.

The term "$C_5$-$C_6$ heteroaryl" as used herein, means a 5- or 6-membered monocyclic heteroaryl ring as described above. Examples of $C_5$-$C_6$ heteroaryl include furanyl, thienyl, imidazolyl, pyrazolyl, 1,2,4-oxadiazolyl, 1,2,4-trazolyl, 1,3-thiazolyl, pyridinyl, and pyrazinyl.

The term "heteroatom" as used herein, means a nitrogen, oxygen, and sulfur.

The term "oxo" as used herein, means a =O group.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, horses, dogs, cats, rabbits, rats, mice and the like. In preferred embodiments, the subject is a human.

Compounds

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

In certain embodiments of formula (I), $R^1$ is $C_1$-$C_3$ alkyl or $C_1$-$C_3$ haloalkyl.

In certain embodiments, $R^1$ is $C_1$-$C_3$ alkyl.

In certain embodiments, $R^1$ is methyl.

In certain embodiments, $R^2$ is H.

In certain embodiments of formula (I), $R^3$ is O—$C_1$-$C_6$ alkyl, —$OCD_2CH_3$, or —$OCD_2CD_3$.

In certain embodiments, $R^3$ is —O—$C_1$-$C_6$ alkyl.

In certain embodiments, $R^3$ is —O—$C_1$-$C_3$ alkyl.

In certain embodiments, $R^3$ is —O—$CH_2CH_3$.

In certain embodiments, $R^3$ is —$OCD_2CH_3$ or —$OCD_2CD_3$.

In certain embodiments of formula (I), $Y^1$ is N or $CR^4$, wherein $R^4$ is H, $C_1$-$C_3$ alkyl, or $C_1$-$C_3$ haloalkyl.

In certain embodiments, $Y^1$ is N.

In certain embodiments, $Y^1$ is $CR^4$. In some such embodiments, $R^4$ is H.

In certain embodiments of formula (I), $A^2$ is $CR^5$, and $A^1$, $A^3$, and $A^4$ are $CR^6$; or $A^2$ is $CR^5$, $A^1$ and $A^3$ are $CR^6$, and $A^4$ is N.

In certain embodiments, $A^2$ is $CR^5$, and $A^1$, $A^3$, and $A^4$ are $CR^6$.

In certain embodiments, $A^2$ is $CR^5$, $A^1$ and $A^3$ are $CR^6$, and $A^4$ is N.

In certain embodiments of formula (I), $R^5$ is O—$C_1$-$C_6$ alkylenyl-$R^{5a}$, $N(R^{5d})$—$C_1$-$C_6$ alkylenyl-$R^{5a}$, $N(R^{5d})C(O)$—$C_1$-$C_6$ alkylenyl-$R^{5b}$, $N(R^{5d})SO_2$—$C_1$-$C_6$ alkylenyl-$R^{5c}$, $N(R^{5d})C(O)N(R^{5d})$-$G^1$, $N(R^{5d})C(O)N(R^{5d})$—$C_1$-$C_6$ alkylenyl-$R^{5a}$, $N(R^{5d})SO_2N(R^{5d})$—$C_1$-$C_6$ alkylenyl-$R^{5a}$, $C(O)N(R^{5d})$—$C_1$-$C_6$ alkylenyl-$R^{5a}$, or $SO_2N(R^{5d})$—$C_1$-$C_6$ alkylenyl-$R^{5a}$.

In certain embodiments, $R^5$ is $N(R^{5d})$—$C_1$-$C_6$ alkylenyl-$R^{5a}$, $N(R^{5d})C(O)$—$C_1$-$C_6$ alkylenyl-$R^{5b}$, $N(R^{5d})SO_2$—$C_1$-$C_6$ alkylenyl-$R^{5c}$, or $N(R^{5d})C(O)N(R^{5d})$-$G^1$.

In certain embodiments, $R^5$ is $N(R^{5d})$—$C_1$-$C_6$ alkylenyl-$R^{5a}$. In some such embodiments, $R^{5d}$ is H or $SO_2R^{5aa}$. In some such embodiments, $R^{5d}$ is H. In some such embodiments, $R^{5d}$ is $SO_2R^{5aa}$ wherein $R^{5aa}$ is $C_1$-$C_6$ alkyl or ($C_1$-$C_6$ alkylenyl)-$G^1$. In some such embodiments, $R^{5d}$ is $SO_2R^{5aa}$ wherein $R^{5aa}$ is $C_1$-$C_3$ alkyl or —($C_1$-$C_3$ alkylenyl)-$G^1$. In some such embodiments, $R^{5d}$ is $SO_2R^{5aa}$ wherein $R^{5aa}$ is $C_1$-$C_3$ alkyl or ($C_1$-$C_3$ alkylenyl)-$G^1$, wherein $G^1$ is optionally substituted phenyl. In some such embodiments, $R^{5d}$ is $SO_2R^{5aa}$ wherein $R^{5aa}$ is ethyl. In some such embodiments, $R^{5d}$ is $SO_2R^{5aa}$ wherein $R^{5aa}$ is —($CH_2$)-$G^1$ and $G^1$ is optionally substituted phenyl. In some such embodiments, $R^{5a}$ is $G^1$ or —$C(O)OR^{5dd}$. In some such embodiments, $R^{5a}$ is —$C(O)OR^{5dd}$ wherein $R^{5dd}$ is $C_1$-$C_6$ alkyl. In some such embodiments, $R^{5a}$ is $G^1$. In some such embodiments, $R^{5a}$ is $G^1$ wherein $G^1$ is phenyl, naphthyl, $C_3$-$C_6$ cycloalkyl, heterocycle, or heteroaryl, each of which is optionally substituted. In the embodiments wherein $R^{5a}$ is $G^1$, examples of $G^1$ include phenyl, naphthyl, cyclopropyl, cyclohexyl, bicyclo[2.2.1]heptyl, furanyl, oxazolyl, thiazolyl, pyrazolyl, imidazolyl, 1,2,4-triazolyl, pyridinyl, pyrimidinyl, pyrazinyl, 3,4-dihydro-2H-chromen-6-yl, 6,7-dihydro-5H-pyrrolo[1,2-a]imidazol-2-yl, benzoxazolyl, quinolinyl, tetrahydropyranyl, and 1,4-dioxanyl; each of which is optionally substituted. In some such embodiments, $R^{5a}$ is $G^1$ wherein $G^1$ is optionally substituted phenyl or optionally substituted cyclopropyl.

In certain embodiments, $R^5$ is $N(R^{5d})C(O)$—$C_1$-$C_6$ alkylenyl-$R^{5b}$. In some such embodiments, $R^{5d}$ is H, $C_1$-$C_3$ alkyl, or ($C_1$-$C_6$ alkylenyl)-$G^1$. In some such embodiments, $R^{5d}$ is H. In some such embodiments, $R^{5d}$ is ($C_1$-$C_3$ alkylenyl)-$G^1$ wherein $G^1$ is optionally substituted phenyl or optionally substituted $C_3$-$C_6$ cycloalkyl. In some such embodiments, $R^{5d}$ is —($CH_2$)-$G^1$ wherein $G^1$ is optionally substituted phenyl or optionally substituted $C_3$-$C_6$ cycloalkyl. In some such embodiments, $R^{5d}$ is —($CH_2$)-$G^1$ wherein $G^1$ is optionally substituted phenyl or optionally substituted cyclopropyl. In some such embodiments, $R^{5b}$ is $G^1$, —$OR^{5aa}$, —$S(O)_2R^{5aa}$, —$NR^{5bb}C(O)R^{5dd}$, —$NR^{5bb}S(O)_2R^{5dd}$, —$C(O)R^{5aa}$, or —$C(O)NR^{5bb}R^{5cc}$. In some such embodiments, $R^{5b}$ is —$OR^{5aa}$, —$S(O)_2R^{5aa}$, —$NR^{5bb}C(O)R^{5aa}$, —$NR^{5bb}S(O)_2R^{5dd}$, —$C(O)R^{5aa}$, or —$C(O)NR^{5bb}R^{5cc}$. In some such embodiments wherein $R^{5b}$ is —$OR^{5aa}$, —$S(O)_2R^{5aa}$, —$NR^{5bb}C(O)R^{5dd}$, —$NR^{5bb}S(O)_2R^{5dd}$, —$C(O)R^{5aa}$, or —$C(O)NR^{5bb}R^{5cc}$, $R^{5aa}$, $R^{5cc}$, and $R^{5dd}$ are each independently optionally substituted phenyl or optionally substituted benzyl; $R^{5bb}$ is H or $C_1$-$C_3$ alkyl. In some such embodiments, $R^{5b}$ is $G^1$. In some such embodiments wherein $R^{5b}$ is $G^1$, $G^1$ is phenyl, naphthyl, $C_3$-$C_6$ cycloalkyl, heterocycle, or heteroaryl, each of which is optionally substituted. In some such embodiments $R^{5b}$ is $G^1$, wherein $G^1$ is phenyl, cyclopropyl, cyclohexyl, bicyclo[2.2.1]heptyl, furanyl, oxazolyl, thiazolyl, pyrazolyl, imidazolyl, 1,2,4-triazolyl, pyridinyl, pyrimidinyl, naphthyl, pyrazinyl, benzoxazolyl, quinolinyl, 3,4-dihydro-2H-chromen-6-yl, 6,7-dihydro-5H-pyrrolo[1,2-a]imidazol-2-yl, tetrahydropyranyl, and 1,4-dioxanyl; each of which is optionally substituted. In some such embodiments $R^{5b}$ is $G^1$, wherein $G^1$ is optionally substituted phenyl or optionally substituted $C_5$-$C_6$ heteroaryl.

In certain embodiments, $R^5$ is $N(R^{5d})SO_2$—$C_1$-$C_6$ alkylenyl-$R^{5c}$. In some such embodiments, $R^{5d}$ is H or —$(C_1$-$C_6$ alkylenyl)-$G^1$.

In certain embodiments, $R^5$ is $N(R^{5d})C(O)N(R^{5d})$-$G^1$. In some such embodiments, $R^{5d}$ is H. In some such embodiments, $G^1$ is optionally substituted phenyl.

In certain embodiments of formula (I), $R^6$ is H, $C_1$-$C_6$ alkyl, halogen, $C_1$-$C_6$ haloalkyl, or —CN.

In certain embodiments, $R^6$ is H, $C_1$-$C_3$ alkyl, halogen, $C_1$-$C_3$ haloalkyl, or —CN.

In certain embodiments, $R^6$ is H.

In certain embodiments of formula (I), $Y^2$ is -L-$G^2$; wherein L is O or $N(R^x)$, $R^x$ is H or $C_1$-$C_6$ alkyl; and $G^2$ is aryl, heteroaryl, heterocycle, cycloalkyl, or cycloalkenyl, each of which is optionally substituted with 1, 2, 3, 4, or 5 $R^{2g}$ groups.

In certain embodiments L is O.

In certain embodiments, L is $N(R^x)$ wherein $R^x$ is H or $C_1$-$C_6$ alkyl. In some such embodiments, $R^x$ is H.

In certain embodiments of formula (I), $G^2$ is phenyl, $C_3$-$C_6$ cycloalkyl, or $C_4$-$C_6$ heterocycle; each of which is optionally substituted with 1, 2, 3, 4, or 5 $R^{2g}$ groups. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In certain embodiments of formula (I), $G^2$ is phenyl or $C_3$-$C_6$ cycloalkyl; each of which is optionally substituted with 1, 2, 3, 4, or 5 $R^{2g}$ groups. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In certain embodiments, $G^2$ is phenyl or cyclopropyl; each of which is optionally substituted with 1, 2, or 3 $R^{2g}$ groups. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In certain embodiments, $G^2$ is phenyl that is substituted with 1, 2, or 3 $R^{2g}$ groups. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In certain embodiments, $G^2$ is cyclopropyl which is optionally substituted with 1, 2, or 3 $R^{2g}$ groups. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

Various embodiments of substituents $Y^1$, $Y^2$, $R^1$, $R^2$, $R^3$, $A^1$, $A^2$, $A^3$, and $A^4$ have been discussed above. These substituents embodiments can be combined to form various embodiments of compounds of formula (I). All embodiments of compounds of formula (I), formed by combining the substituent embodiments discussed above are within the scope of Applicant's invention, and some illustrative embodiments of the compounds of formula (I) are provided below.

In one embodiment, the invention is directed to compounds of formula (I), wherein L is O, and $G^2$ is phenyl, $C_3$-$C_6$ cycloalkyl, or $C_4$-$C_6$ heterocycle; each of which is optionally substituted with 1, 2, 3, 4, or 5 $R^{2g}$ groups. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In one embodiment, the invention is directed to compounds of formula (I), wherein $A^2$ is $CR^5$, $A^1$, $A^3$, and $A^4$ are $CR^6$; and $R^5$ is $N(R^{5d})$—$C_1$-$C_6$ alkylenyl-$R^{5a}$, $N(R^{5d})C(O)$—$C_1$-$C_6$ alkylenyl-$R^{5b}$, $N(R^{5d})SO_2$—$C_1$-$C_6$ alkylenyl-$R^{5c}$, or $N(R^{5d})C(O)N(R^{5d})$-$G^1$. In some such embodiments, $R^6$ is H.

In one embodiment, the invention is directed to compounds of formula (I), wherein $A^2$ is $CR^5$, and $A^1$ and $A^3$ are $CR^6$, $A^4$ is N, and $R^5$ is $N(R^{5d})$—$C_1$-$C_6$ alkylenyl-$R^{5a}$, $N(R^{5d})C(O)$—$C_1$-$C_6$ alkylenyl-$R^{5b}$, $N(R^{5d})SO_2$—$C_1$-$C_6$ alkylenyl-$R^{5c}$, or $N(R^{5d})C(O)N(R^{5d})$-$G^1$. In some such embodiments, $R^6$ is H.

In one embodiment, the invention is directed to compounds of formula (I), wherein $R^1$ is methyl, $Y^1$ is $CR^4$, and $R^3$ is —O—$C_1$-$C_3$ alkyl. In some such embodiments, $R^4$ is H.

In one embodiment, the invention is directed to compounds of formula (I), wherein $R^1$ is methyl, $Y^1$ is $CR^4$, $R^3$ is —O—$C_1$-$C_3$ alkyl, $A^2$ is $CR^5$, and $A^1$, $A^3$, and $A^4$ are $CR^6$. In some such embodiments, $R^4$ is H. In some such embodiments, $R^6$ is H.

In one embodiment, the invention is directed to compounds of formula (I), wherein $R^1$ is methyl, $Y^1$ is $CR^4$, $R^3$ is —O—$C_1$-$C_3$ alkyl, $A^2$ is $CR^5$, $A^1$, $A^3$, and $A^4$ are $CR^6$, L is O, and $G^2$ is phenyl or $C_3$-$C_6$ cycloalkyl; each of which is optionally substituted with 1, 2, 3, 4, or 5 $R^{2g}$ groups. In some such embodiments, $R^4$ is H. In some such embodiments, $R^6$ is H. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In one embodiment, the invention is directed to compounds of formula (I), wherein $R^1$ is methyl, $Y^1$ is $CR^4$, $R^3$ is —O—$C_1$-$C_3$ alkyl, $A^2$ is $CR^5$, $A^1$, $A^3$, and $A^4$ are $CR^6$, L is O, $G^2$ is phenyl or $C_3$-$C_6$ cycloalkyl; each of which is optionally substituted with 1, 2, 3, 4, or 5 $R^{2g}$ groups; and $R^5$ is $N(R^{5d})$—$C_1$-$C_6$ alkylenyl-$R^{5a}$, $N(R^{5d})C(O)$—$C_1$-$C_6$ alkylenyl-$R^{5b}$, $N(R^{5d})SO_2$—$C_1$-$C_6$ alkylenyl-$R^{5c}$, or $N(R^{5d})C(O)N(R^{5d})$-$G^1$. In some such embodiments, $R^4$ is H. In some such embodiments, $R^6$ is H. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In one embodiment, the invention is directed to compounds of formula (I), wherein $R^1$ is methyl, $Y^1$ is $CR^4$, $R^3$ is —O—$C_1$-$C_3$ alkyl, $A^2$ is $CR^5$, $A^1$, $A^3$, and $A^4$ are $CR^6$, L is O, $G^2$ is phenyl which is optionally substituted with 1, 2, or 3 $R^{2g}$ groups; $R^5$ is $N(R^{5d})$—$C_1$-$C_6$ alkylenyl-$R^{5a}$, $N(R^{5d})$C(O)—$C_1$-$C_6$ alkylenyl-$R^{5b}$, $N(R^{5d})SO_2$—$C_1$-$C_6$ alkylenyl-$R^{5c}$, or $N(R^{5d})C(O)N(R^{5d})$-$G^1$; and $R^4$ is H. In some such embodiments, $R^6$ is H. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In one embodiment, the invention is directed to compounds of formula (I), wherein $R^1$ is methyl, $Y^1$ is $CR^4$, $R^3$ is —O—$C_1$-$C_3$ alkyl, $A^2$ is $CR^5$, $A^1$, $A^3$, and $A^4$ are $CR^6$, L is O, $G^2$ is phenyl which is optionally substituted with 1, 2, or 3 $R^{2g}$ groups; $R^5$ is $N(R^{5d})$—$C_1$-$C_6$ alkylenyl-$R^{5a}$; and $R^4$ is H. In some such embodiments, $R^6$ is H. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In one embodiment, the invention is directed to compounds of formula (I), wherein $R^1$ is methyl, $Y^1$ is $CR^4$, $R^3$ is —O—$C_1$-$C_3$ alkyl, $A^2$ is $CR^5$, $A^1$, $A^3$, and $A^4$ are $CR^6$, L is O, $G^2$ is phenyl which is optionally substituted with 1, 2, or 3 $R^{2g}$ groups; $R^5$ is $N(R^{5d})$—$C_1$-$C_6$ alkylenyl-$R^{5a}$; $R^{5d}$ is H or $SO_2R^{5aa}$; $R^{5a}$ is $G^1$; and $R^4$ is H. In some such embodiments, $R^6$ is H. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In one embodiment, the invention is directed to compounds of formula (I), wherein $R^1$ is methyl, $Y^1$ is $CR^4$, $R^3$ is —O—$C_1$-$C_3$ alkyl, $A^2$ is $CR^5$, $A^1$, $A^3$, and $A^4$ are $CR^6$, L is O, $G^2$ is phenyl which is optionally substituted with 1, 2, or 3 $R^{2g}$ groups; $R^5$ is $N(R^{5d})$—$C_1$-$C_6$ alkylenyl-$R^{5a}$; $R^{5d}$ is $SO_2R^{5aa}$; $R^{5aa}$ is $C_1$-$C_3$ alkyl or —($C_1$-$C_3$ alkylenyl)-$G^1$; $R^{5a}$ is $G^1$ wherein $G^1$ is phenyl, naphthyl, $C_3$-$C_6$ cycloalkyl, heteroaryl, or heterocycle; each of which is optionally substituted; and $R^4$ is H. In some such embodiments, $R^6$ is H. In some such embodiments, $R^{2g}$ is $C_1$-$C_3$ alkyl, halogen, $C_1$-$C_3$ haloalkyl, —CN, or —$OR^{z1}$ wherein $R^{1z}$ is H, $C_1$-$C_3$ alkyl, or $C_1$-$C_3$ haloalkyl. In some such embodiments, $R^{2g}$ is halogen. In some such embodiments, $R^{2g}$ is F.

In one embodiment, the invention is directed to compounds of formula (I), wherein $R^1$ is methyl, $Y^1$ is $CR^4$, $R^3$ is —O—$C_1$-$C_3$ alkyl, $A^2$ is $CR^5$, $A^1$, $A^3$, and $A^4$ are $CR^6$, L is O, $G^2$ is phenyl which is optionally substituted with 1, 2, or 3 $R^{2g}$ groups; $R^5$ is $N(R^{5d})$—$C_1$-$C_6$ alkylenyl-$R^{5a}$; $R^{5d}$ is $SO_2R^{5aa}$; $R^{5aa}$ is —($C_1$-$C_3$ alkylenyl)-$G^1$ wherein $G^1$ is optionally substituted phenyl; $R^{5a}$ is $G^1$ wherein $G^1$ is optionally substituted phenyl or optionally substituted cyclopropyl; and $R^4$ is H. In some such embodiments, $R^6$ is H. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In one embodiment, the invention is directed to compounds of formula (I), wherein $R^1$ is methyl, $Y^1$ is $CR^4$, $R^3$ is —O—$C_1$-$C_3$ alkyl, $A^2$ is $CR^5$, $A^1$, $A^3$, and $A^4$ are $CR^6$, L is O, $G^2$ is phenyl which is optionally substituted with 1, 2, or 3 $R^{2g}$ groups; $R^5$ is $N(R^{5d})$C(O)—$C_1$-$C_6$ alkylenyl-$R^{5b}$; and $R^4$ is H. In some such embodiments, $R^6$ is H. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In one embodiment, the invention is directed to compounds of formula (I), wherein $R^1$ is methyl, $Y^1$ is $CR^4$, $R^3$ is —O—$C_1$-$C_3$ alkyl, $A^2$ is $CR^5$, $A^1$, $A^3$, and $A^4$ are $CR^6$, L is O, $G^2$ is phenyl which is optionally substituted with 1, 2, or 3 $R^{2g}$ groups; $R^5$ is $N(R^{5d})$C(O)—$C_1$-$C_6$ alkylenyl-$R^{5b}$; $R^{5d}$ is H, $C_1$-$C_3$ alkyl, or —($C_1$-$C_6$ alkylenyl)-$G^1$; $R^{5b}$ is $G^1$, —$OR^{5aa}$, —$S(O)_2R^{5aa}$, —$NR^{5bb}C(O)R^{5dd}$, —$NR^{5bb}S(O)_2R^{5dd}$, —$C(O)R^{5aa}$, or —$C(O)NR^{5bb}R^{5cc}$; $R^{5aa}$, $R^{5cc}$, and $R^{5dd}$ are each independently optionally substituted phenyl or optionally substituted benzyl; $R^{5bb}$ is H or $C_1$-$C_3$ alkyl; and $R^4$ is H. In some such embodiments, $R^6$ is H. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In one embodiment, the invention is directed to compounds of formula (I), wherein $R^1$ is methyl, $Y^1$ is $CR^4$, $R^3$ is —O—$C_1$-$C_3$ alkyl, $A^2$ is $CR^5$, $A^1$, $A^3$, and $A^4$ are $CR^6$, L is O, $G^2$ is phenyl which is optionally substituted with 1, 2, or 3 $R^{2g}$ groups; $R^5$ is $N(R^{5d})$C(O)—$C_1$-$C_6$ alkylenyl-$R^{5b}$; $R^{5d}$ is H; $R^{5b}$ is $G^1$ wherein $G^1$ is phenyl, naphthyl, $C_3$-$C_6$ cycloalkyl, heterocycle, or heteroaryl, each of which is optionally substituted; and $R^4$ is H. In some such embodiments, $R^6$ is H. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In one embodiment, the invention is directed to compounds of formula (I), wherein $R^1$ is methyl, $Y^1$ is $CR^4$, $R^3$ is O—$C_1$-$C_3$ alkyl, $A^2$ is $CR^5$, $A^1$, $A^3$, and $A^4$ are $CR^6$, L is O, $G^2$ is phenyl which is optionally substituted with 1, 2, or 3 $R^{2g}$ groups; $R^5$ is $N(R^{5d})$C(O)—$C_1$-$C_6$ alkylenyl-$R^{5b}$; $R^{5d}$ is H; $R^{5b}$ is $G^1$ wherein $G^1$ is optionally substituted phenyl or optionally substituted $C_5$-$C_6$ heteroaryl; and $R^4$ is H. In some such embodiments, $R^6$ is H. In some such embodiments, $R^{2g}$ is $C_1$-$C_3$ alkyl, halogen, $C_1$-$C_3$ haloalkyl, —CN, or —$OR^{z1}$ where $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

In one embodiment, the invention is directed to compounds of formula (I), wherein $R^1$ is methyl, $Y^1$ is $CR^4$, $R^3$ is O—$C_1$-$C_3$ alkyl, $A^2$ is $CR^5$, $A^1$, $A^3$, and $A^4$ are $CR^6$, L is O, $G^2$ is phenyl which is optionally substituted with 1, 2, or 3 $R^{2g}$ groups; $R^5$ is $N(R^{5d})C(O)N(R^{5d})$-$G^1$; and $R^4$ is H. In some such embodiments, $R^6$ is H. In some such embodiments, $R^{2g}$ is $C_1$-$C_3$ alkyl, halogen, $C_1$-$C_3$ haloalkyl, —CN, or —$OR^{z1}$ wherein $R^{z1}$ is H, $C_1$-$C_3$ alkyl, or $C_1$-$C_3$ haloalkyl. In some such embodiments, $R^{2g}$ is halogen. In some such embodiments, $R^{2g}$ is F.

Compounds of formula (I) may contain one or more asymmetrically substituted atoms. Compounds of formula (I) may also exist as individual stereoisomers (including enantiomers and diastereomers) and mixtures thereof. Individual stereoisomers of compounds of formula (I) may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii)

separation of the mixture of enantiomers or diastereomers on chiral chromatographic columns.

Compounds of formula (I) may also include the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or heterocycle are designated as being of cis or trans configuration.

Within the present invention it is to be understood that compounds disclosed herein may exhibit the phenomenon of tautomerism and all tautomeric isomers are included in the scope of the invention.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Exemplary compounds of formula (I) include, but are not limited to:

2-(2-chloro-5-fluorophenyl)-N-[4-(2,4-difluorophenoxy)-3-(4-ethoxy-1-methyl-6-oxo-1,6-dihydropyridin-3-yl)phenyl]acetamide;

N-[4-(2,4-difluorophenoxy)-3-(4-ethoxy-1-methyl-6-oxo-1,6-dihydropyridin-3-yl)phenyl]-2-(3,4-dihydro-2H-chromen-6-yl)acetamide;

2-(4-chloro-2-fluorophenyl)-N-[4-(2,4-difluorophenoxy)-3-(4-ethoxy-1-methyl-6-oxo-1,6-dihydropyridin-3-yl)phenyl]acetamide;

N-[4-(2,4-difluorophenoxy)-3-(4-ethoxy-1-methyl-6-oxo-1,6-dihydropyridin-3-yl)phenyl]-2-(1-methyl-1H-pyrazol-4-yl)acetamide;

N-[4-(2,4-difluorophenoxy)-3-(4-ethoxy-1-methyl-6-oxo-1,6-dihydropyridin-3-yl)phenyl]-2-(6-methylpyridin-3-yl)acetamide;

N-[4-(2,4-difluorophenoxy)-3-(4-ethoxy-1-methyl-6-oxo-1,6-dihydropyridin-3-yl)phenyl]-2-(1,5-dimethyl-1H-pyrazol-3-yl)acetamide;

N-[4-(2,4-difluorophenoxy)-3-(4-ethoxy-1-methyl-6-oxo-1,6-dihydropyridin-3-yl)phenyl]-2-(2-methyl-1,3-thiazol-5-yl)acetamide;

N-[4-(2,4-difluorophenoxy)-3-(4-ethoxy-1-methyl-6-oxo-1,6-dihydropyridin-3-yl)phenyl]-2-[3-(2-fluorophenyl)-1H-pyrazol-1-yl]acetamide;

5-[2-(2,4-difluorophenoxy)-5-{[3-(1H-pyrazol-1-yl)propyl]amino}phenyl]-4-ethoxy-1-methylpyridin-2(1H)-one;

5-{2-(2,4-difluorophenoxy)-5-[(6,7-dihydro-5H-pyrrolo[1,2-a]imidazol-2-ylmethyl)amino]phenyl}-4-ethoxy-1-methylpyridin-2(1H)-one;

5-[2-(2,4-difluorophenoxy)-5-{[(6-methylpyridin-2-yl)methyl]amino}phenyl]-4-ethoxy-1-methylpyridin-2(1H)-one;

5-[2-(2,4-difluorophenoxy)-5-{[(3-methylpyridin-2-yl)methyl]amino}phenyl]-4-ethoxy-1-methylpyridin-2(1H)-one;

5-[2-(2,4-difluorophenoxy)-5-{[(1-methyl-1H-pyrazol-5-yl)methyl]amino}phenyl]-4-ethoxy-1-methylpyridin-2(1H)-one;

methyl 4-{[4-(2,4-difluorophenoxy)-3-(4-ethoxy-1-methyl-6-oxo-1,6-dihydropyridin-3-yl)phenyl]amino}butanoate;

1-[4-(2,4-difluorophenoxy)-3-(4-ethoxy-1-methyl-6-oxo-1,6-dihydropyridin-3-yl)phenyl]-3-(3-phenoxyphenyl)urea;

1-[4-(2,4-difluorophenoxy)-3-(4-ethoxy-1-methyl-6-oxo-1,6-dihydropyridin-3-yl)phenyl]-3-(2,4-dimethylphenyl)urea;

1-[4-(2,4-difluorophenoxy)-3-(4-ethoxy-1-methyl-6-oxo-1,6-dihydropyridin-3-yl)phenyl]-3-(3,5-dimethylphenyl)urea;

1-[4-(2,4-difluorophenoxy)-3-(4-ethoxy-1-methyl-6-oxo-1,6-dihydropyridin-3-yl)phenyl]-3-[4-(trifluoromethoxy)phenyl]urea;

1-[4-(2,4-difluorophenoxy)-3-(4-ethoxy-1-methyl-6-oxo-1,6-dihydropyridin-3-yl)phenyl]-3-(2,5-dimethylphenyl)urea;

1-[4-(2,4-difluorophenoxy)-3-(4-ethoxy-1-methyl-6-oxo-1,6-dihydropyridin-3-yl)phenyl]-3-(4-fluorophenyl)urea;

1-(3-chlorophenyl)-3-[4-(2,4-difluorophenoxy)-3-(4-ethoxy-1-methyl-6-oxo-1,6-dihydropyridin-3-yl)phenyl]urea;

1-[4-(2,4-difluorophenoxy)-3-(4-ethoxy-1-methyl-6-oxo-1,6-dihydropyridin-3-yl)phenyl]-3-(3-methoxyphenyl)urea;

5-{2-(2,4-difluorophenoxy)-5-[(1,3-oxazol-5-ylmethyl)amino]phenyl}-4-ethoxy-1-methylpyridin-2(1H)-one;

5-[2-(2,4-difluorophenoxy)-5-{[(1-methyl-1H-imidazol-5-yl)methyl]amino}phenyl]-4-ethoxy-1-methylpyridin-2(1H)-one;

5-[2-(2,4-difluorophenoxy)-5-{[(1-ethyl-1H-pyrazol-3-yl)methyl]amino}phenyl]-4-ethoxy-1-methylpyridin-2(1H)-one;

N-[4-(2,4-difluorophenoxy)-3-(4-ethoxy-1-methyl-6-oxo-1,6-dihydropyridin-3-yl)phenyl]-5-oxo-5-phenylpentanamide;

N-[4-(2,4-difluorophenoxy)-3-(4-ethoxy-1-methyl-6-oxo-1,6-dihydropyridin-3-yl)phenyl]-3-(phenylsulfonyl)propanamide;

N-[4-(2,4-difluorophenoxy)-3-(4-ethoxy-1-methyl-6-oxo-1,6-dihydropyridin-3-yl)phenyl]-2-(3-phenoxyphenyl)acetamide;

N-[4-(2,4-difluorophenoxy)-3-(4-ethoxy-1-methyl-6-oxo-1,6-dihydropyridin-3-yl)phenyl]-2-[4-(methylsulfonyl)phenyl]acetamide;

N-[4-(2,4-difluorophenoxy)-3-(4-ethoxy-1-methyl-6-oxo-1,6-dihydropyridin-3-yl)phenyl]-3-phenoxypropanamide;

N-[4-(2,4-difluorophenoxy)-3-(4-ethoxy-1-methyl-6-oxo-1,6-dihydropyridin-3-yl)phenyl]-2-(naphthalen-1-yl)acetamide;

N-[4-(2,4-difluorophenoxy)-3-(4-ethoxy-1-methyl-6-oxo-1,6-dihydropyridin-3-yl)phenyl]-2-{[(4-methylphenyl)sulfonyl]amino}acetamide;

N-[4-(2,4-difluorophenoxy)-3-(4-ethoxy-1-methyl-6-oxo-1,6-dihydropyridin-3-yl)phenyl]-2-(4-methylphenoxy)acetamide;

N-[4-(2,4-difluorophenoxy)-3-(4-ethoxy-1-methyl-6-oxo-1,6-dihydropyridin-3-yl)phenyl]-3-(2,3,4-trimethoxyphenyl)propanamide;

2-(benzyloxy)-N-[4-(2,4-difluorophenoxy)-3-(4-ethoxy-1-methyl-6-oxo-1,6-dihydropyridin-3-yl)phenyl]acetamide;

2-(1,2-benzoxazol-3-yl)-N-[4-(2,4-difluorophenoxy)-3-(4-ethoxy-1-methyl-6-oxo-1,6-dihydropyridin-3-yl)phenyl]acetamide;

N-[4-(2,4-difluorophenoxy)-3-(4-ethoxy-1-methyl-6-oxo-1,6-dihydropyridin-3-yl)phenyl]-2-(4-phenoxyphenyl)acetamide;

N-[4-(2,4-difluorophenoxy)-3-(4-ethoxy-1-methyl-6-oxo-1,6-dihydropyridin-3-yl)phenyl]-4-phenylbutanamide;

N-[4-(2,4-difluorophenoxy)-3-(4-ethoxy-1-methyl-6-oxo-1,6-dihydropyridin-3-yl)phenyl]-2-(naphthalen-2-yl)acetamide;
N-[4-(2,4-difluorophenoxy)-3-(4-ethoxy-1-methyl-6-oxo-1,6-dihydropyridin-3-yl)phenyl]-N'-phenylpentanediamide;
N-[4-(2,4-difluorophenoxy)-3-(4-ethoxy-1-methyl-6-oxo-1,6-dihydropyridin-3-yl)phenyl]-3-phenylpropanamide;
2-(biphenyl-4-yl)-N-[4-(2,4-difluorophenoxy)-3-(4-ethoxy-1-methyl-6-oxo-1,6-dihydropyridin-3-yl)phenyl]acetamide;
N-[4-(2,4-difluorophenoxy)-3-(4-ethoxy-1-methyl-6-oxo-1,6-dihydropyridin-3-yl)phenyl]-4-oxo-4-phenylbutanamide;
N-[4-(2,4-difluorophenoxy)-3-(4-ethoxy-1-methyl-6-oxo-1,6-dihydropyridin-3-yl)phenyl]-4-phenoxybutanamide;
2-[4-(benzyloxy)phenyl]-N-[4-(2,4-difluorophenoxy)-3-(4-ethoxy-1-methyl-6-oxo-1,6-dihydropyridin-3-yl)phenyl]acetamide;
N-[4-(2,4-difluorophenoxy)-3-(4-ethoxy-1-methyl-6-oxo-1,6-dihydropyridin-3-yl)phenyl]-2-(2-methoxyphenyl)acetamide;
N-(2-{[4-(2,4-difluorophenoxy)-3-(4-ethoxy-1-methyl-6-oxo-1,6-dihydropyridin-3-yl)phenyl]amino}-2-oxoethyl)benzamide;
2-cyclohexyl-N-[4-(2,4-difluorophenoxy)-3-(4-ethoxy-1-methyl-6-oxo-1,6-dihydropyridin-3-yl)phenyl]acetamide;
2-[(1S,4R)-bicyclo[2.2.1]hept-2-yl]-N-[4-(2,4-difluorophenoxy)-3-(4-ethoxy-1-methyl-6-oxo-1,6-dihydropyridin-3-yl)phenyl]acetamide;
5-[5-{[2-(benzyloxy)-3-methoxybenzyl]amino}-2-(2,4-difluorophenoxy)phenyl]-4-ethoxy-1-methylpyridin-2(1H)-one;
5-[5-{[4-(benzyloxy)benzyl]amino}-2-(2,4-difluorophenoxy)phenyl]-4-ethoxy-1-methylpyridin-2(1H)-one;
5-{5-[(4-tert-butylbenzyl)amino]-2-(2,4-difluorophenoxy)phenyl}-4-ethoxy-1-methylpyridin-2(1H)-one;
5-{5-[(2,6-difluorobenzyl)amino]-2-(2,4-difluorophenoxy)phenyl}-4-ethoxy-1-methylpyridin-2(1H)-one;
5-[2-(2,4-difluorophenoxy)-5-{[3-(4-methoxyphenoxy)benzyl]amino}phenyl]-4-ethoxy-1-methylpyridin-2(1H)-one;
5-[5-({[5-(2-chlorophenyl)furan-2-yl]methyl}amino)-2-(2,4-difluorophenoxy)phenyl]-4-ethoxy-1-methylpyridin-2(1H)-one;
4-({[4-(2,4-difluorophenoxy)-3-(4-ethoxy-1-methyl-6-oxo-1,6-dihydropyridin-3-yl)phenyl]amino}methyl)benzonitrile;
2-({[4-(2,4-difluorophenoxy)-3-(4-ethoxy-1-methyl-6-oxo-1,6-dihydropyridin-3-yl)phenyl]amino}methyl)benzonitrile;
5-{2-(2,4-difluorophenoxy)-5-[(quinolin-4-ylmethyl)amino]phenyl}-4-ethoxy-1-methylpyridin-2(1H)-one;
5-[5-{[(5-chloro-3-methyl-1-phenyl-1H-pyrazol-4-yl)methyl]amino}-2-(2,4-difluorophenoxy)phenyl]-4-ethoxy-1-methylpyridin-2(1H)-one;
5-{2-(2,4-difluorophenoxy)-5-[({5-[2-(trifluoromethyl)phenyl]furan-2-yl}methyl)amino]phenyl}-4-ethoxy-1-methylpyridin-2(1H)-one;
5-{5-[(4-butoxybenzyl)amino]-2-(2,4-difluorophenoxy)phenyl}-4-ethoxy-1-methylpyridin-2(1H)-one;
5-{2-(2,4-difluorophenoxy)-5-[(4-phenoxybenzyl)amino]phenyl}-4-ethoxy-1-methylpyridin-2(1H)-one;
3-({[4-(2,4-difluorophenoxy)-3-(4-ethoxy-1-methyl-6-oxo-1,6-dihydropyridin-3-yl)phenyl]amino}methyl)benzonitrile;
5-{2-(2,4-difluorophenoxy)-5-[(4-fluorobenzyl)amino]phenyl}-4-ethoxy-1-methylpyridin-2(1H)-one;
5-{5-[(cyclopropylmethyl)amino]-2-(2,4-difluorophenoxy)phenyl}-4-ethoxy-1-methylpyridin-2(1H)-one;
1-(2-chloro-5-fluorophenyl)-N-(cyclopropylmethyl)-N-[4-(2,4-difluorophenoxy)-3-(4-ethoxy-1-methyl-6-oxo-1,6-dihydropyridin-3-yl)phenyl]methanesulfonamide;
2-(2-chloro-5-fluorophenyl)-N-(cyclopropylmethyl)-N-[4-(2,4-difluorophenoxy)-3-(4-ethoxy-1-methyl-6-oxo-1,6-dihydropyridin-3-yl)phenyl]acetamide;
N-[4-(benzyloxy)benzyl]-2-(2-chloro-5-fluorophenyl)-N-[4-(2,4-difluorophenoxy)-3-(4-ethoxy-1-methyl-6-oxo-1,6-dihydropyridin-3-yl)phenyl]acetamide;
2-(2-chloro-5-fluorophenyl)-N-[4-(2,4-difluorophenoxy)-3-(4-ethoxy-1-methyl-6-oxo-1,6-dihydropyridin-3-yl)phenyl]-N-(4-fluorobenzyl)acetamide;
2-(2-chloro-5-fluorophenyl)-N-[4-(2,4-difluorophenoxy)-3-(4-ethoxy-1-methyl-6-oxo-1,6-dihydropyridin-3-yl)phenyl]propanamide;
2-(2-chloro-5-fluorophenyl)-N-[4-(2,4-difluorophenoxy)-3-(4-ethoxy-1-methyl-6-oxo-1,6-dihydropyridin-3-yl)phenyl]-N-methylacetamide;
N-(cyclopropylmethyl)-N-[4-(2,4-difluorophenoxy)-3-(4-ethoxy-1-methyl-6-oxo-1,6-dihydropyridin-3-yl)phenyl]ethanesulfonamide;
N-benzyl-N-[4-(2,4-difluorophenoxy)-3-(4-ethoxy-1-methyl-6-oxo-1,6-dihydropyridin-3-yl)phenyl]ethanesulfonamide;
N-(2-chlorobenzyl)-N-[4-(2,4-difluorophenoxy)-3-(4-ethoxy-1-methyl-6-oxo-1,6-dihydropyridin-3-yl)phenyl]ethanesulfonamide;
N-[4-(2,4-difluorophenoxy)-3-(4-ethoxy-1-methyl-6-oxo-1,6-dihydropyridin-3-yl)phenyl]-N-(2-phenylethyl)ethanesulfonamide;
N-(cyclopropylmethyl)-N-[4-(2,4-difluorophenoxy)-3-(4-ethoxy-1-methyl-6-oxo-1,6-dihydropyridin-3-yl)phenyl]-1-phenylmethanesulfonamide;
N-benzyl-N-[4-(2,4-difluorophenoxy)-3-(4-ethoxy-1-methyl-6-oxo-1,6-dihydropyridin-3-yl)phenyl]-1-phenylmethanesulfonamide;
N-(2-chlorobenzyl)-N-[4-(2,4-difluorophenoxy)-3-(4-ethoxy-1-methyl-6-oxo-1,6-dihydropyridin-3-yl)phenyl]-1-phenylmethanesulfonamide;
N-[4-(2,4-difluorophenoxy)-3-(4-ethoxy-1-methyl-6-oxo-1,6-dihydropyridin-3-yl)phenyl]-1-phenyl-N-(2-phenylethyl)methanesulfonamide;
N-[2-(2-chlorophenyl)ethyl]-N-[4-(2,4-difluorophenoxy)-3-(4-ethoxy-1-methyl-6-oxo-1,6-dihydropyridin-3-yl)phenyl]ethanesulfonamide;
N-[4-(2,4-difluorophenoxy)-3-(4-ethoxy-1-methyl-6-oxo-1,6-dihydropyridin-3-yl)phenyl]-2-(3-phenyl-1H-pyrazol-1-yl)acetamide;
2-(5-chloro-2-fluorophenyl)-N-[4-(2,4-difluorophenoxy)-3-(4-ethoxy-1-methyl-6-oxo-1,6-dihydropyridin-3-yl)phenyl]acetamide;
N-[4-(2,4-difluorophenoxy)-3-(4-ethoxy-1-methyl-6-oxo-1,6-dihydropyridin-3-yl)phenyl]-2-(2-methyl-1,3-thiazol-4-yl)acetamide;
N-[4-(2,4-difluorophenoxy)-3-(4-ethoxy-1-methyl-6-oxo-1,6-dihydropyridin-3-yl)phenyl]-2-(1H-pyrazol-1-yl)acetamide;
N-[4-(2,4-difluorophenoxy)-3-(4-ethoxy-1-methyl-6-oxo-1,6-dihydropyridin-3-yl)phenyl]-2-(pyrimidin-5-yl)acetamide;
N-[4-(2,4-difluorophenoxy)-3-(4-ethoxy-1-methyl-6-oxo-1,6-dihydropyridin-3-yl)phenyl]-2-(3,5-dimethyl-1H-pyrazol-1-yl)acetamide;

N-[4-(2,4-difluorophenoxy)-3-(4-ethoxy-1-methyl-6-oxo-1,6-dihydropyridin-3-yl)phenyl]-2-(1H-1,2,4-triazol-1-yl)acetamide;

N-[4-(2,4-difluorophenoxy)-3-(4-ethoxy-1-methyl-6-oxo-1,6-dihydropyridin-3-yl)phenyl]-2-(pyrazin-2-yl)acetamide;

N-[2-(2-chlorophenyl)ethyl]-N-[4-(2,4-difluorophenoxy)-3-(4-ethoxy-1-methyl-6-oxo-1,6-dihydropyridin-3-yl)phenyl]-1-phenylmethanesulfonamide;

N-[4-(2,4-difluorophenoxy)-3-(4-ethoxy-1-methyl-6-oxo-1,6-dihydropyridin-3-yl)phenyl]-1-phenyl-N-(1,3-thiazol-2-ylmethyl)methanesulfonamide;

N-[4-(2,4-difluorophenoxy)-3-(4-ethoxy-1-methyl-6-oxo-1,6-dihydropyridin-3-yl)phenyl]-N-(pyridin-3-ylmethyl)ethanesulfonamide;

N-[4-(2,4-difluorophenoxy)-3-(4-ethoxy-1-methyl-6-oxo-1,6-dihydropyridin-3-yl)phenyl]-1-phenyl-N-(pyridin-3-ylmethyl)methanesulfonamide;

N-[4-(2,4-difluorophenoxy)-3-(4-ethoxy-1-methyl-6-oxo-1,6-dihydropyridin-3-yl)phenyl]-N-(pyrimidin-5-ylmethyl)ethanesulfonamide;

N-[4-(2,4-difluorophenoxy)-3-(4-ethoxy-1-methyl-6-oxo-1,6-dihydropyridin-3-yl)phenyl]-1-phenyl-N-(pyrimidin-5-ylmethyl)methanesulfonamide;

N-[4-(2,4-difluorophenoxy)-3-(4-ethoxy-1-methyl-6-oxo-1,6-dihydropyridin-3-yl)phenyl]-N-(pyrazin-2-ylmethyl)ethanesulfonamide;

N-[4-(2,4-difluorophenoxy)-3-(4-ethoxy-1-methyl-6-oxo-1,6-dihydropyridin-3-yl)phenyl]-1-phenyl-N-(pyrazin-2-ylmethyl)methanesulfonamide;

N-[4-(2,4-difluorophenoxy)-3-(4-ethoxy-1-methyl-6-oxo-1,6-dihydropyridin-3-yl)phenyl]-N-[(1-methyl-1H-pyrazol-4-yl)methyl]ethanesulfonamide;

N-[4-(2,4-difluorophenoxy)-3-(4-ethoxy-1-methyl-6-oxo-1,6-dihydropyridin-3-yl)phenyl]-N-[(1-methyl-1H-pyrazol-4-yl)methyl]-1-phenylmethanesulfonamide;

N-[4-(2,4-difluorophenoxy)-3-(4-ethoxy-1-methyl-6-oxo-1,6-dihydropyridin-3-yl)phenyl]-N-(1,3-thiazol-2-ylmethyl)ethanesulfonamide;

N-[4-(2,4-difluorophenoxy)-3-(4-ethoxy-1-methyl-6-oxo-1,6-dihydropyridin-3-yl)phenyl]-N-[(1-methyl-1H-imidazol-4-yl)methyl]ethanesulfonamide;

N-[4-(2,4-difluorophenoxy)-3-(4-ethoxy-1-methyl-6-oxo-1,6-dihydropyridin-3-yl)phenyl]-N-[(1-methyl-1H-imidazol-4-yl)methyl]-1-phenylmethanesulfonamide;

N-[4-(2,4-difluorophenoxy)-3-(4-ethoxy-1-methyl-6-oxo-1,6-dihydropyridin-3-yl)phenyl]-N-[(2S)-1,4-dioxan-2-ylmethyl]ethanesulfonamide;

N-[4-(2,4-difluorophenoxy)-3-(4-ethoxy-1-methyl-6-oxo-1,6-dihydropyridin-3-yl)phenyl]-N-(tetrahydro-2H-pyran-4-ylmethyl)ethanesulfonamide; and N-[4-(2,4-difluorophenoxy)-3-(4-ethoxy-1-methyl-6-oxo-1,6-dihydropyridin-3-yl)phenyl]-N-[2-(tetrahydro-2H-pyran-4-yl)ethyl]ethanesulfonamide.

A further embodiment include compounds of formula (I) or pharmaceutically acceptable salt thereof, wherein the compounds are selected from the group consisting of 2-(2-chloro-5-fluorophenyl)-N-[4-(2,4-difluorophenoxy)-3-(4-ethoxy-1-methyl-6-oxo-1,6-dihydropyridin-3-yl)phenyl]acetamide;

N-[4-(2,4-difluorophenoxy)-3-(4-ethoxy-1-methyl-6-oxo-1,6-dihydropyridin-3-yl)phenyl]-2-(2-methyl-1,3-thiazol-5-yl)acetamide;

N-(cyclopropylmethyl)-N-[4-(2,4-difluorophenoxy)-3-(4-ethoxy-1-methyl-6-oxo-1,6-dihydropyridin-3-yl)phenyl]ethanesulfonamide;

N-benzyl-N-[4-(2,4-difluorophenoxy)-3-(4-ethoxy-1-methyl-6-oxo-1,6-dihydropyridin-3-yl)phenyl]ethanesulfonamide;

N-(cyclopropylmethyl)-N-[4-(2,4-difluorophenoxy)-3-(4-ethoxy-1-methyl-6-oxo-1,6-dihydropyridin-3-yl)phenyl]-1-phenylmethanesulfonamide;

N-benzyl-N-[4-(2,4-difluorophenoxy)-3-(4-ethoxy-1-methyl-6-oxo-1,6-dihydropyridin-3-yl)phenyl]-1-phenylmethanesulfonamide;

N-(2-chlorobenzyl)-N-[4-(2,4-difluorophenoxy)-3-(4-ethoxy-1-methyl-6-oxo-1,6-dihydropyridin-3-yl)phenyl]-1-phenylmethanesulfonamide;

N-[4-(2,4-difluorophenoxy)-3-(4-ethoxy-1-methyl-6-oxo-1,6-dihydropyridin-3-yl)phenyl]-1-phenyl-N-(2-phenylethyl)methanesulfonamide;

N-[4-(2,4-difluorophenoxy)-3-(4-ethoxy-1-methyl-6-oxo-1,6-dihydropyridin-3-yl)phenyl]-2-(3-phenyl-1H-pyrazol-1-yl)acetamide; and N-[4-(2,4-difluorophenoxy)-3-(4-ethoxy-1-methyl-6-oxo-1,6-dihydropyridin-3-yl)phenyl]-2-(2-methyl-1,3-thiazol-4-yl)acetamide.

Compounds of formula (I) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds described herein, including compounds of general formula (I) and specific examples, can be prepared by methodologies known in the art, for example, through the reaction schemes depicted in schemes 1-7. The variables $A^1$, $A^2$, $A^3$, $A^4$, $R^1$, $R^2$, $R^3$, $R^4$, $R^6$, $G^1$, $G^2$, $Y^1$, $Y^2$ and used in the following schemes have the meanings as set forth in the summary and detailed description sections, unless otherwise noted.

Abbreviations used in the descriptions of the schemes and the specific examples have the following meanings: DIPEA for diisopropylethylamine, DMA for N,N-dimethylacetamide, DME for 1,2-dimethoxyethane, DMF for N,N-dimethylformamide, DMSO for dimethyl sulfoxide, dppf for 1,1'-bis(diphenylphosphino)ferrocene, EDC or EDAC for 1-ethyl-3-[3-(dimethylamino)propyl]-carbodiimide hydrochloride, mesylate for methyl sulfonate; HATU for O-(7-azabenzotriazol-1-yl)-N,N,N',N'-tetramethyluronium hexafluorophosphate; HOBT for 1-hydroxybenzotriazole hydrate, HPLC for High Performance Liquid chromatography, Prep HPLC for Preparative High Performance Liquid chromatography, MeOH for methanol, TFA for trifluoroacetic acid, THF for tetrahydrofuran, and tosylate for p-toluene sulfonate.

Compounds of general formula (I) may be prepared using the general procedure as outlined in Scheme 1. Conversion of (1), wherein Z is Cl, Br, I, or triflate to compounds of general formula (I) may be achieved by treatment with boronic acids of formula (2) or derivatives thereof (e.g., pinacol ester) under Suzuki coupling conditions (N. Miyama and A. Suzuki, Chem. Rev. 1995, 95:2457-2483, J. Organomet. Chem. 1999, 576:147-148). For example, the coupling reaction may be conducted in the presence of a palladium catalyst and a base, and optionally in the presence of a ligand, and in a suitable solvent at elevated temperature (about 80° C. to about 150° C.). The reaction may be facilitated by microwave irradiation. Examples of the palladium catalyst include, but are not limited to, tetrakis (triphenylphosphine)palladium(O), tris(dibenzylideneacetone)dipalladium(O), bis(triphenylphosphine)palladium(II) dichloride, and palladium(II)acetate. Examples of suitable bases that may be employed include, but not limited to, carbonates, acetates, or phosphates of sodium, potassium, and cesium, and cesium fluoride. Examples of suitable ligands include, but are not limited to, 1,3,5,7-tetramethyl-6-phenyl-2,4,8-trioxa-6-phosphaadamantane, 2-dicyclohexylphosphino-2',4',6'-triisopropylbiphenyl (X-phos), and 1,1'-bis(diphenylphosphanyl) ferrocene. Non-limiting examples of suitable solvent include methanol, ethanol, dimethoxyethane, N,N-dimethylformamide, dimethylsulfoxide, dioxane, tetrahydrofuran, and water, or a mixture thereof.

Alternatively, compounds of formula (I) may be synthesized by reaction of boronic acids (4) or derivatives thereof (e.g., pinacol ester) under Suzuki coupling conditions as described above with compounds of formula (5) wherein Z is Br, Cl, I, or triflate.

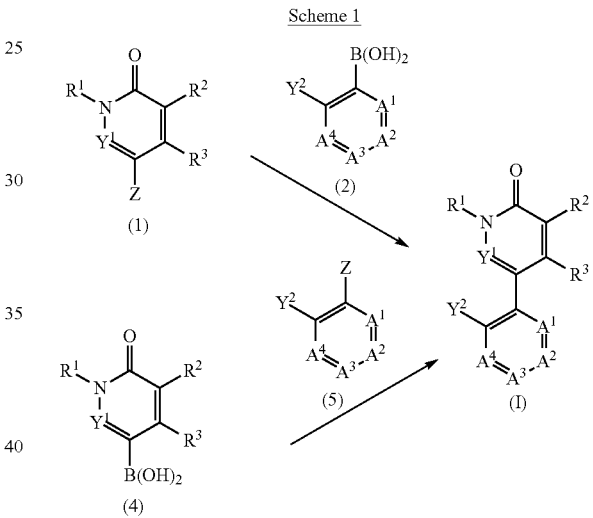

Scheme 1

Intermediates (1) wherein $Y^1$ is $CR^4$, Z is Br, Cl, or I, and $R^3$ is —O—$C_1$-$C_6$ alkyl may be prepared as outlined in Scheme 2.

Generally, heteroaryl amines of formula (6) wherein $R^{101}$ is Br, Cl, or I may be converted to alcohols of formula (7) by treatment with sodium nitrite and an acid such as, for example sulfuric acid, in a solvent such as water, and at a temperature from about 0° C. to about 25° C.

Reaction of compounds of formula (7) with a $C_1$-$C_3$ alkyl halide, in the presence of a base such as carbonate of cesium, sodium, or potassium and in a solvent such as, but not limited to, dimethylformamide, tetrahydrofuran, or dimethylsulfoxide, provides intermediates of formula (8). The reaction may be conducted at temperature such as, but not limited to, about 25° C. to about 60° C.

Displacement of the chlorine atom of formula (8) with alcohols of formula $C_1$-$C_6$ alkyl-OH provides compounds of formula (1a). Displacement of the chlorine atom may be accomplished in a solvent such as, but not limited to, methanol or ethanol, and in the presence of a base such as, but not limited to, sodium ethoxide or sodium hydride, and at a temperature from about 40° C. to about 80° C.

Scheme 2

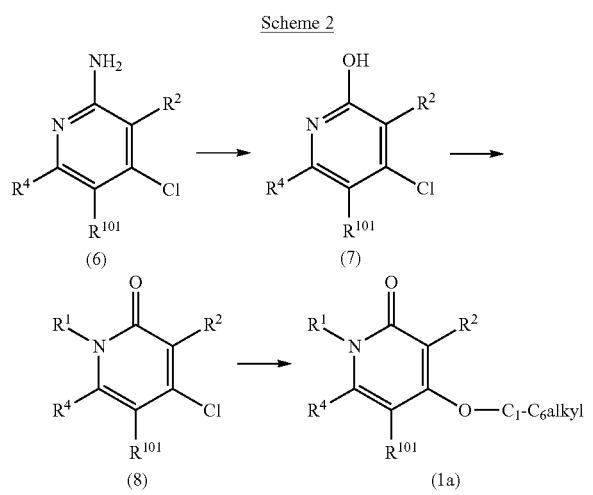

Boronic acids of formula (2) wherein $Y^2$ is —O-$G^2$, $A^1$, $A^3$, and $A^4$ are $CR^6$, and $A^2$ is C—$NH_2$ may be prepared as illustrated in Scheme 3.

Displacement of the fluorine atom of compounds (9) with alcohols of formula $G^2OH$ provides compounds of formula (10). The displacement reaction may be accomplished in a solvent such as, but not limited to, dimethylsulfoxide, dimethylformamide, dioxane, or tetrahydrofuran, and in the presence of a base such as, but not limited to, carbonate of cesium, sodium, or potassium, or sodium hydride, and at a temperature of about 40° C. to about 120° C.

Reduction of compounds (10) to anilines of formula (11) may be achieved with iron powder in the presence of ammonium chloride in a solvent such as, but not limited to, tetrahydrofuran, ethanol, or water, or a mixture thereof, and at a temperature from about 80° C. to about 120° C. Alternatively the reduction may be carried out with tin chloride in hydrochloric acid at a temperature from about 80° C. to about 120° C. Transformation of (10) to (11) may also be conducted in the presence of a catalyst such as platinum oxide or palladium on charcoal, in a solvent such as ethanol or methanol and under hydrogen pressure.

Treatment of the compounds of formula (11) with 4,4,4', 4',5,5,5',5'-octamethyl-2,2'-bi(1,3,2-dioxaborolane) using Suzuki coupling reaction conditions as discussed in Scheme 1 generally affords compounds of formula (2a).

Scheme 3

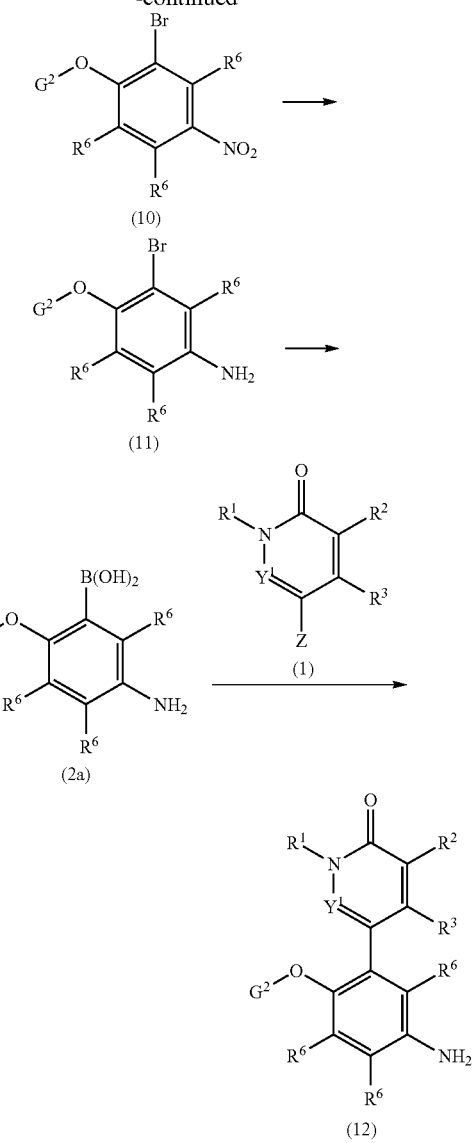

Transformation of anilines of formula (12) is generally illustrated in Scheme 4.

Tertiary sulfonamides of structure (15) wherein $R^{102}$ is $C_1$-$C_6$ alkylenyl-$G^1$ may be formed by treatment of secondary anilines (14) with sulfonyl chlorides of formula $R^{5aa}SO_2Cl$, in the presence of a base such as triethylamine or diisopropylethylamine and in a solvent such as dichloromethane or tetrahydrofuran, at a temperature from about 0° C. to about 40° C. Alternatively, sulfonamides of formula (13) may be alkylated by treatment of an alkyl halide of formula $R^{102}X$ where X is chloro, bromo, iodo, tosylate or mesylate in the presence of a base such as sodium hydride or potassium carbonate in a solvent such as DMF or methanol to provide tertiary sulfonamides of structure (15). The reaction may be conducted at a temperature from about 40° C. to about 180° C., optionally facilitated by microwave irradiation.

Scheme 4

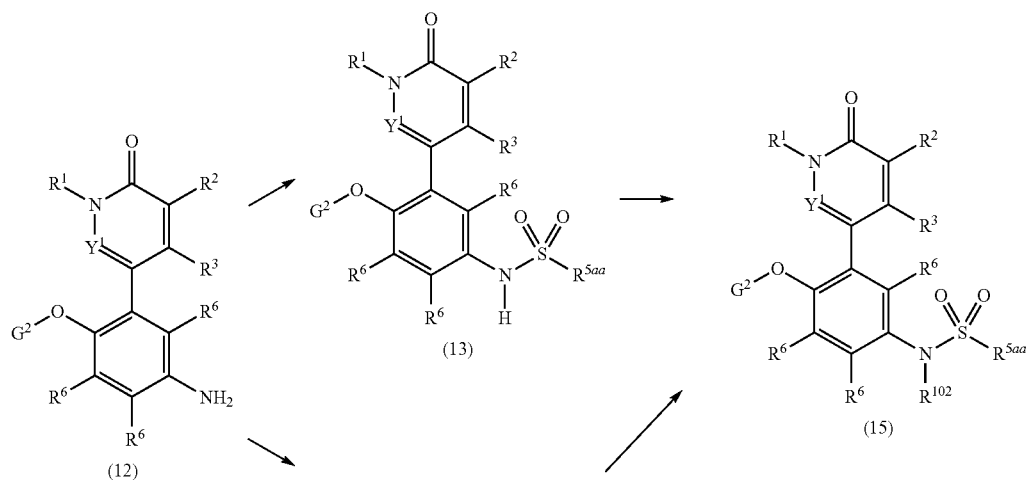

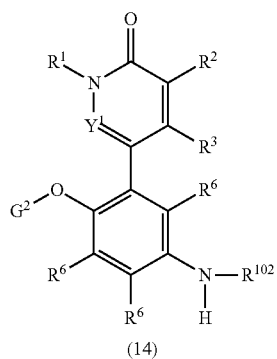

As shown in Scheme 5, tertiary amides (18) wherein $R^{104}$ is $C_1$-$C_6$ alkyl or ($C_1$-$C_6$ alkylenyl)-$G^1$ and $R^{103}$ is —($C_1$-$C_6$ alkylenyl)-$G^1$ may be formed by treatment of secondary anilines (17) with carboxylic acids of formula $R^{103}$COOH in the presence of a coupling agent such as HATU or EDAC and a base such as diisopropylethylaminde or triethylamine, and in a solvent such as dimethylacetamide, tetrahydrofuran, dioxane, or dimethylformamide, at a temperature from about 0° C. to about 100° C. Transformation of secondary anilines (17) to amides (18) may also be accomplished by treatment of (17) with acid chlorides of formula $R^{103}$COCl in the presence of a base such as, for example triethylamine, in a solvent such as, for example, dichloromethane, and at about room temperature. Alternatively, amides of formula (16) may be alkylated by treatment of an alkyl halide of formula $R^{104}$X where X is chloro, bromo, iodo, tosylate or mesylate in the presence of a base such as sodium hydride or sodium hydroxide in a solvent such as DMF or dichloromethane to provide tertiary amides of structure (18).

Scheme 5

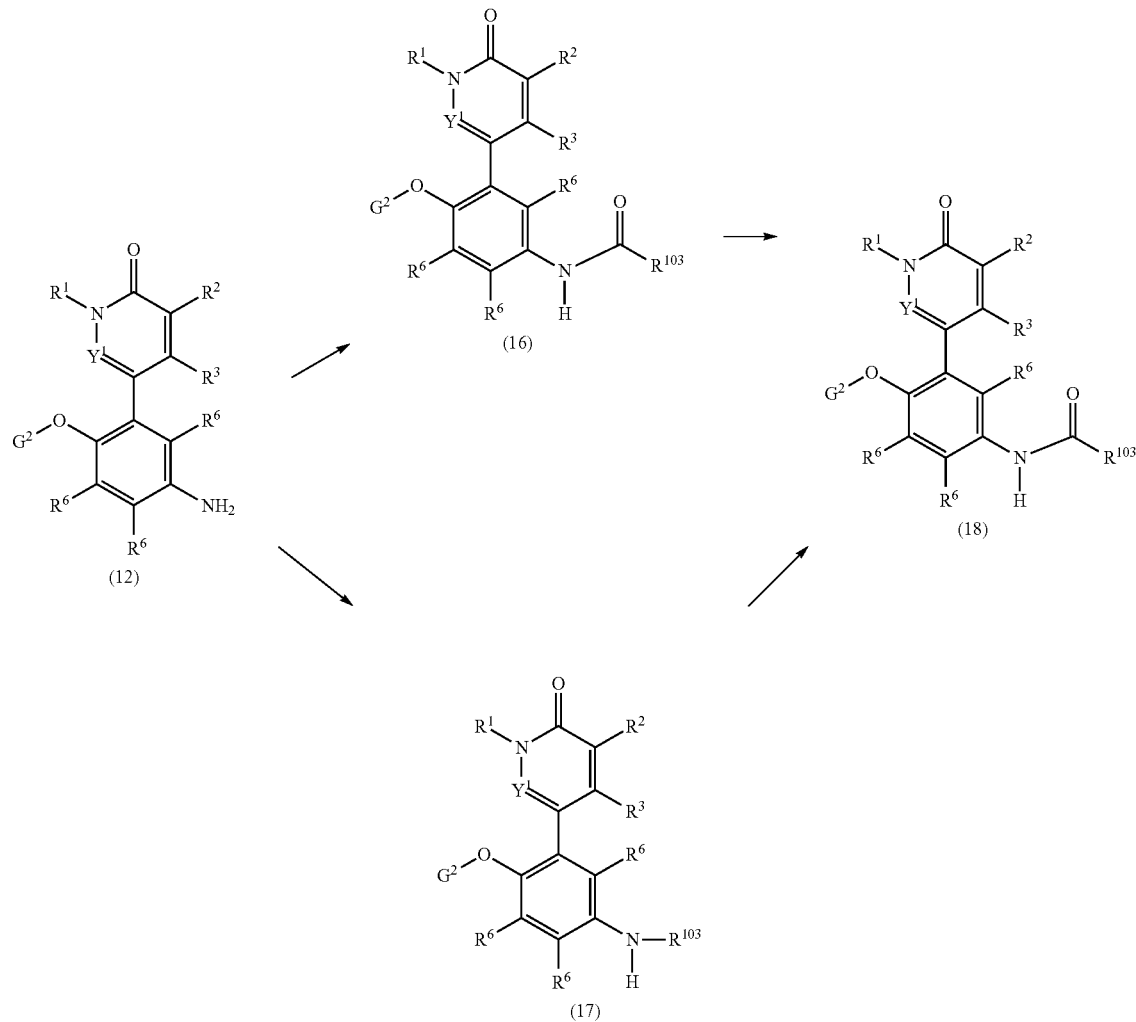

Treatment of aniline (12) with isocyanates of formula G¹NCO in the presence of a base such as pyridine, and in a solvent such as tetrahydrofuran, dioxane, or dimethylacetamide, at a temperature from about 0° C. to about 100° C. provides ureas of formula (19).

Scheme 6

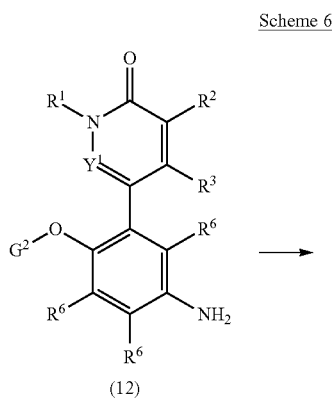

-continued

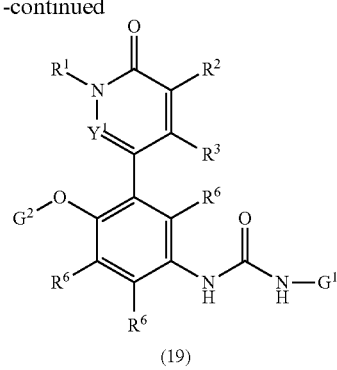

Treatment of anilines (12) with aldehydes of formula G¹CHO under reductive amination conditions such as, but not limited to, sodium cyanoborohydride and acetic acid in a solvent such as, but not limited to, dimethylacetamide or dichloromethane provides secondary anilines of formula (20).

Amides (16) may be prepared by reaction of amines (12) with acids of formula $R^{103}$COOH or acid chlorides of formula R¹⁰³COCl, employing reaction conditions as discussed in Scheme 5 for the transformation of (17) to (18).

Scheme 7

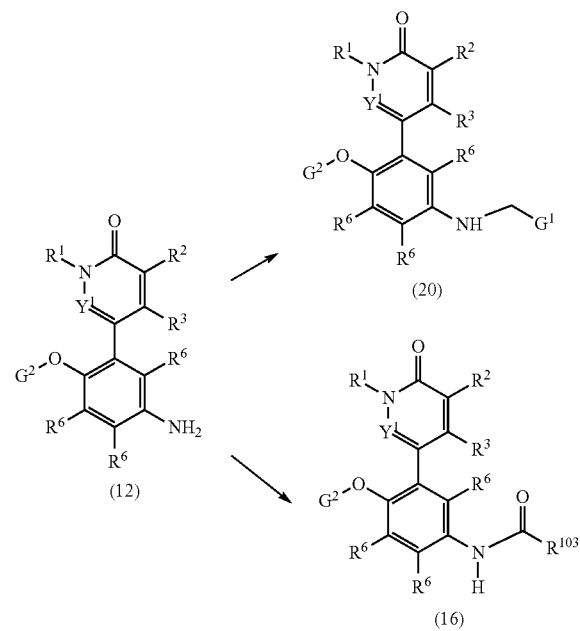

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be further processed in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis (3$^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Pharmaceutical Compositions

This invention also provides for pharmaceutical compositions comprising a therapeutically effective amount of a compound of formula (I), or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or or in combination with a second therapeutic agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula (I). In certain embodiments, the compound of formula (I) may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 μg/kg to 100 mg/kg for a typical subject.

For administration, compounds of the formula (I) may be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula (I) may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

Methods of Use

The compounds of formula (I), or pharmaceutically acceptable salts thereof, and pharmaceutical compositions comprising a compound of formula (I), or a pharmaceutically acceptable salt thereof, can be administered to a subject suffering from a bromodomain-mediated disorder or condition. The term "administering" refers to the method of contacting a compound with a subject. Thus, the compounds of formula (I) may be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of formula (I) may be administered transdermally, topically, via implantation, transdermally, topically, and via implantation. In certain embodiments, the compounds of the formula (I) may be delivered orally. The compounds can also be delivered rectally, bucally, intravaginally, ocularly, andially, or by insufflation. Bromodomain-mediated disorders and conditions can be treated prophylactically, acutely, and chronically using compounds of formula (I), depending on the nature of the disorder or condition. Typically, the host or subject in each of these methods is human, although other mammals can also benefit from the administration of a compound of formula (I).

A "bromodomain-mediated disorder or condition" is characterized by the participation of one or more bromodomains (e.g., BRD4) in the inception, manifestation of one or more symptoms or disease markers, severity, or progression of a disorder or condition. Accordingly, compounds of formula (I) may be used to treat cancer, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

Further, compounds of formula (I) may be used to treat inflammatory diseases, inflammatory conditions, and autoimmune diseases, including, but not limited to: Addison's disease, acute gout, ankylosing spondylitis, asthma, atherosclerosis, Behcet's disease, bullous skin diseases, cardiac myopathy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Compounds of formula (I), or pharmaceutically acceptable salts thereof, may be used to treat AIDS.

The compounds of formula (I) may be co-administered to a subject. The term "co-administered" means the administration of two or more different therapeutic agents or treatments (e.g., radiation treatment) that are administered to a subject by combination in the same pharmaceutical composition or separate pharmaceutical compositions. Thus co-administration involves administration at the same time of a single pharmaceutical composition comprising two or more therapeutic agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPB), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, J. of Immunology 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include ABT-199, AT-101 ((−) gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl) benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 tri-functional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS 1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn- KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The compounds of the invention can also be co-administered with a therapeutically effective amount of one or more agents to treat an inflammatory disease or condition, or autoimmune disease, where examples of the agents include, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (etanercept) and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. In certain embodiments, combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of formula (I) of the invention may be co-administered include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of formula (I) may be combined include the following: TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™) inhibitors and PDE4 inhibitors. A compound of formula (I) may be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of formula (I) may be co-administered include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of formula (I) may be combined with antibodies to cell surface molecules such as CD2, CD3, CD4, CD8, CD19, CD20, CD25, CD28, CD30, CD40, CD45, CD69, CD80, CD86, CD90 or their ligands. A compound of formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

A compound of formula (I) may also be co-administered with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of formula (I) may be co-administered include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (HUMIRA®), CA2 (infliximab), CDP 571, TNFR-Ig constructs, (p75TNFRIgG (ENBREL®) and p55TNFRIgG (LENERCEPT®)).

Non-limiting examples of therapeutic agents for asthma with which a compound of formula (I) may be co-administered include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of formula (I) may be co-administered include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for psoriasis with which a compound of formula (I) may be co-administered include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of formula (I) may be co-administered include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), and efalizumab.

Preferred examples of therapeutic agents for SLE (Lupus) with which a compound of formula (I) may be co-administered include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of formula (I) may be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™).

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, lamivudine, nevirapine, stavudine zalcitabine, and zidovudine. Examples of protease inhibitors include, but are not limited to, amprenavir, indinavir, lopinavir, nelfinavir, ritonavir, and saquinavir.

The following Examples may be used for illustrative purposes and should not be deemed to narrow the scope of the invention.

EXAMPLES

Example 1

2-(2-chloro-5-fluorophenyl)-N-[4-(2,4-difluorophenoxy)-3-(4-ethoxy-1-methyl-6-oxo-1,6-dihydropyridin-3-yl)phenyl]acetamide Example 1A 5-bromo-4-chloropyridin-2-ol 5-Bromo-4-chloropyridin-2-amine (2.01 g, 9.69 mmol) was dissolved in 75% (v/v) sulfuric acid (40.2 mL, 566 mmol) and then chilled in an ice bath. A solution of sodium nitrite (2.21 g, 32.0 mmol) in water (20.1 mL, 1116 mmol) was added drop-wise and the reaction mixture was then stirred for 3 hours. The mixture was concentrated under reduced pressure and aqueous ammonia (15 mL) was added drop-wise. The resulting white precipitate was collected via vacuum filtration and the filter cake washed with cold water (100 mL) then dried in a vacuum oven for 24 hours to give 1.94 g (95%) of the title compound.

Example 1B 5-bromo-4-chloro-1-methylpyridin-2(1H)-one

A flask fitted with a stir bar was charged with Example 1A (27.45 g, 132 mmol), cesium carbonate (51.53 g, 158 mmol) and DMF (325 mL). Methyl iodide (10 mL, 160 mmol) was added drop-wise to the suspension and the mixture stirred at ambient temperature for 1 hour. The mixture was poured into a separatory funnel containing 1:1 saturated aqueous sodium chloride:water (1000 mL) and extracted with ethyl acetate (1000 mL). The organics were washed with saturated aqueous sodium chloride, dried (anhydrous magnesium sulfate), filtered, concentrated, and then triturated with 100 mL of 10% ethyl acetate/heptane. The solids were collected and vacuum dried to provide the title compound.

Example 1C 5-bromo-4-ethoxy-1-methylpyridin-2(1H)-one

A flask with stir bar was charged with Example 1B (3.29 g, 14.79 mmol) in ethanol (80 mL). Sodium ethoxide (21 wt %, 9.65 g, 29.8 mmol) was added and the solution was heated at 80° C. for 70 minutes. The solution was cooled, reduced in volume by rotary evaporation, and then shaken in a separatory funnel with ethyl acetate (200 mL) and saturated aqueous sodium chloride (200 mL) sequentially. The organics were dried over anhydrous sodium sulfate. After filtration and solvent removal the residues were chromatographed on a 40 g silica cartridge eluting with 0-100% ethyl acetate/heptane to provide the title compound.

Example 1D 2-bromo-1-(2,4-difluorophenoxy)-4-nitrobenzene

2-Bromo-1-fluoro-4-nitrobenzene (15 g, 68.2 mmol), 2,4-difluorophenol (7.82 mL, 82 mmol), and cesium carbonate (26.7 g, 82 mmol) were combined in DMSO (75 mL), heated at 110° C. for 1 hour, and then cooled. To the cooled reaction mixture was added water (1000 mL) and saturated aqueous sodium chloride (1000 mL). The mixture was extracted with ethyl acetate (3×200 mL). The combined organics were washed with saturated aqueous sodium chloride, dried (anhydrous magnesium sulfate), filtered, and concentrated under reduced pressure to give a crude solid which was used in the next step without additional purification.

Example 1E 3-bromo-4-(2,4-difluorophenoxy)aniline

A mixture of Example 1D (22.5 g, 68.2 mmol), iron powder (19.0 g, 341 mmol), and ammonium chloride (7.30 g, 136 mmol) in tetrahydrofuran (117 mL), ethanol (117 mL), and water (39 mL) was refluxed at 100° C. for 2 hours. The mixture was cooled just below reflux, and filtered through Celite. The filter cake was washed with warm methanol (3×50 mL). The solution was concentrated under reduced pressure, neutralized to a pH of about 8 with saturated NaHCO₃ (150 mL), and extracted with ethyl acetate (3×100 mL). The combined organics were washed with saturated aqueous sodium chloride, dried (anhydrous magnesium sulfate), filtered, concentrated, and purified by flash chromatography (silica gel, 0-15% ethyl acetate/hexane gradient) to provide the title compound.

Example 1F 4-(2,4-difluorophenoxy)-3-(4,4,5,5-tetramethyl-1,3,2-dioxaborolan-2-yl)aniline Example 1E (14.3 g, 47.7 mmol), 4,4,4',4',5,5,5',5'-octamethyl-2,2'-bi(1,3,2-dioxaborolane) (24 g, 95 mmol), potassium acetate (10.3 g, 105 mmol), 1,3,5,7-tetramethyl-6-phenyl-2,4,8-trioxa-6-phosphaadamantane (1.39 g, 4.77 mmol), and tris(dibenzylideneacetone)dipalladium(O) (1.31 g, 1.43 mmol) were degassed under argon for 30 minutes. Dioxane (200 mL), degassed with argon for 30 minutes, was then added by cannula transfer. The reaction mixture was heated at 80° C. for 22 hours. The cooled mixture was vacuum filtered through Celite, rinsed with ethyl acetate (100 mL), and washed with saturated aqueous sodium chloride (150 mL) and water (150 mL) sequentially. The aqueous phase was extracted with ethyl acetate (3×150 mL). The combined organics were washed with saturated aqueous sodium chloride, dried (anhydrous magnesium sulfate), gravity filtered, and then concentrated under reduced pressure. Purification by flash chromatography (silica gel, 0-25% ethyl acetate/hexane gradient) afforded the title compound.

Example 1G

5-[5-amino-2-(2,4-difluorophenoxy)phenyl]-4-ethoxy-1-methylpyridin-2(1H)-one

A 100 mL microwave reaction vessel fitted with a stir bar was charged with Example 1C (1.49 g, 6.42 mmol), Example 1F (3.11 g, 8.96 mmol), cesium fluoride (2.99 g, 19.68 mmol), palladium tetrakistriphenylphosphine (0.273 g, 0.236 mmol) in DME (17.00 mL)/methanol (8.5 mL), and sealed. The mixture was heated at 90° C. for 45 minutes in a Ethos Microsynth multimode microwave reactor (Milestone Inc.), and then cooled to ambient temperature. The reaction mixture was shaken in a separatory funnel with 300 mL each of saturated aqueous sodium chloride and ethyl acetate. The organics were washed with saturated aqueous sodium chloride and dried over sodium sulfate. After filtration and solvent removal, the residues were adsorbed on a on a 220 g silica cartridge, and eluted with 0-2-10% methanol/dichloromethane to provide the title compound.

Example 1H 2-(2-chloro-5-fluorophenyl)-N-[4-(2,4-difluorophenoxy)-3-(4-ethoxy-1-methyl-6-oxo-1,6-dihydropyridin-3-yl)phenyl]acetamide A solution of Example 1G and DIPEA (0.182 M and 0.52 M in DMA, respectively, 221 µL, 0.40 mmol Example 1G (1.0 equivalent) and 1.21 mmol DIPEA (3.0 equivalents)), HATU (0.182 M in DMA, 221 µL, 0.40 mmol, 1 equivalent) and 2-(2-chloro-5-fluorophenyl)acetic acid (0.40 M in DMA, 151 µL, 0.60 mmol, 1.5 equivalents) were mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 µL min$^{-1}$ (10 minute residence time). Upon exiting the reactor, the solution was loaded directly into an injection loop and purified by preparative HPLC on a Phenomenex Luna C8(2) 5 µm 100 Å AXIA column (50 mm×21.2 mm), eluting with a gradient of acetonitrile (A) and 0.1% trifluoroacetic acid in water (B) at a flow rate of 30 mL/min (0-0.5 min 5% A, 0.5-6.5 min linear gradient 5-100% A, 6.5-8.5 min 100% A, 8.5-9.0 min linear gradient 100-5% A, 9.0-10 min 5% A) to provide the title compound. $^1$H NMR (400 MHz, DMSO-d$_6$/D$_2$O) δ 10.37 (s, 1H), 7.59-7.46 (m, 4H), 7.37-7.27 (m, 2H), 7.18 (td, J=8.5, 3.1 Hz, 1H), 7.14-6.93 (m, 2H), 6.90 (d, J=8.7 Hz, 1H), 5.82 (s, 1H), 3.92 (q, J=7.0 Hz, 2H), 3.85 (s, 2H), 3.36 (s, 3H), 1.14 (t, J=7.0 Hz, 3H). MS (APCI+) m/z 543.0 (M+H)$^+$.

Example 2

N-[4-(2,4-difluorophenoxy)-3-(4-ethoxy-1-methyl-6-oxo-1,6-dihydropyridin-3-yl)phenyl]-2-(3,4-dihydro-2H-chromen-6-yl)acetamide Example 2 was prepared according to the procedure used for the preparation of Example 1H, substituting 2-(chroman-6-yl)acetic acid for 2-(2-chloro-5-fluorophenyl)acetic acid. $^1$H NMR (400 MHz, DMSO-d$_6$/D$_2$O) δ 10.23 (s, 1H), 7.58-7.49 (m, 3H), 7.32 (ddd, J=11.2, 8.6, 2.7 Hz, 1H), 7.06-6.84 (m, 5H), 6.70-6.64 (m, 1H), 5.82 (s, 1H), 4.13-4.06 (m, 2H), 3.92 (q, J=7.0 Hz, 2H), 3.48 (s, 2H), 3.36 (s, 3H), 2.71 (t, J=6.4 Hz, 2H), 1.99-1.85 (m, 2H), 1.13 (t, J=6.9 Hz, 3H). MS (APCI+) m/z 549.0 (M+H)$^+$.

Example 3

2-(4-chloro-2-fluorophenyl)-N-[4-(2,4-difluorophenoxy)-3-(4-ethoxy-1-methyl-6-oxo-1,6-dihydropyridin-3-yl)phenyl]acetamide Example 3 was prepared according to the procedure used for the preparation of Example 1H, substituting 2-(5-chloro-2-fluorophenyl)acetic acid for 2-(2-chloro-5-fluorophenyl)acetic acid. $^1$H NMR (400 MHz, DMSO-d$_6$/D$_2$O) δ 10.35 (s, 1H), 7.59-7.49 (m, 2H), 7.46-7.35 (m, 1H), 7.37-7.24 (m, 1H), 7.12-6.93 (m, 1H), 6.89 (d, J=8.6 Hz, 1H), 5.82 (s, 1H), 3.92 (q, J=7.0 Hz, 1H), 3.36 (s, 2H), 1.15 (s, 1H), 1.13 (d, J=6.9 Hz, 2H). MS (APCI+) m/z 543.0 (M+H)$^+$.

Example 4

N-[4-(2,4-difluorophenoxy)-3-(4-ethoxy-1-methyl-6-oxo-1,6-dihydropyridin-3-yl)phenyl]-2-(1-methyl-1H-pyrazol-4-yl)acetamide Example 4 was prepared according to the procedure used for the preparation of Example 1H, substituting 2-(1-methyl-1H-pyrazol-4-yl)acetic acid for 2-(2-chloro-5-fluorophenyl)acetic acid to provide the title compound as a trifluoroacetate salt. $^1$H NMR (400 MHz, DMSO-d$_6$/D$_2$O) δ 7.59 (s, 1H), 7.58-7.49 (m, 3H), 7.38-7.27 (m, 2H), 7.10-6.92 (m, 2H), 6.89 (d, J=8.5 Hz, 1H), 5.82 (s, 1H), 3.98-3.88 (m, 2H), 3.45 (s, 2H), 3.37 (s, 3H), 1.13 (t, J=6.9 Hz, 3H). MS (APCI+) m/z 495.0 (M+H)$^+$.

Example 5

N-[4-(2,4-difluorophenoxy)-3-(4-ethoxy-1-methyl-6-oxo-1,6-dihydropyridin-3-yl)phenyl]-2-(6-methylpyridin-3-yl)acetamide Example 5 was prepared according to the procedure used for the preparation of Example 1H, substituting 2-(6-methylpyridin-3-yl)acetic acid for 2-(2-chloro-5-fluorophenyl)acetic acid to provide the title compound as a trifluoroacetate salt. $^1$H NMR (400 MHz, DMSO-d$_6$/D$_2$O) δ 8.70 (d, J=2.0 Hz, 1H), 8.41 (dd, J=8.2, 2.0 Hz, 1H), 7.90 (d, J=8.2 Hz, 1H), 7.58-7.49 (m, 3H), 7.33 (ddd, J=11.2, 8.6, 2.7 Hz, 1H), 7.15-6.93 (m, 2H), 6.90 (d, J=8.6 Hz, 1H), 5.83 (s, 1H), 3.98-3.85 (m, 4H), 3.37 (s, 3H), 2.72 (s, 3H), 1.13 (t, J=6.9 Hz, 3H). MS (APCI+) m/z 506.0 (M+H)$^+$.

Example 6

N-[4-(2,4-difluorophenoxy)-3-(4-ethoxy-1-methyl-6-oxo-1,6-dihydropyridin-3-yl)phenyl]-2-(1,5-dimethyl-1H-pyrazol-3-yl)acetamide Example 6 was prepared according to the procedure used for the preparation of Example 1H, substituting 2-(1,5-dimethyl-1H-pyrazol-3-yl)acetic acid for 2-(2-chloro-5-fluorophenyl)acetic acid to provide the title compound as a trifluoroacetate salt. $^1$H NMR (400 MHz, DMSO-d$_6$/D$_2$O) δ 7.59-7.49 (m, 3H), 7.32 (ddd, J=11.2, 8.6, 2.7 Hz, 1H), 7.06-6.92 (m, 2H), 6.89 (d, J=8.6 Hz, 1H), 5.99 (s, 1H), 5.83 (s, 1H), 3.92 (q, J=7.0 Hz, 2H), 3.51 (s, 2H), 3.37 (s, 3H), 2.21 (s, 3H), 1.14 (t, J=6.9 Hz, 3H). MS (APCI+) m/z 509.0 (M+H)$^+$.

Example 7

N-[4-(2,4-difluorophenoxy)-3-(4-ethoxy-1-methyl-6-oxo-1,6-dihydropyridin-3-yl)phenyl]-2-(2-methyl-1,3-thiazol-5-yl)acetamide Example 7 was prepared according to the procedure used for the preparation of Example 1H, substituting 2-(2-methyl-1,3-thiazol-5-yl)acetic acid for 2-(2-chloro-5-fluorophenyl)acetic acid to provide the title compound. $^1$H NMR (400 MHz, DMSO-d$_6$/D$_2$O) δ 7.60-7.48 (m, 4H), 7.33 (ddd, J=11.2, 8.6, 2.7 Hz, 1H), 7.10-6.93 (m, 2H), 6.90 (d, J=8.7 Hz, 1H), 5.83 (s, 1H), 3.93 (q, J=7.0 Hz, 4H), 3.90-3.87 (m, 2H), 3.37 (s, 3H), 1.14 (t, J=6.9 Hz, 3H). MS (APCI+) m/z 512.0 (M+H)$^+$.

Example 8

N-[4-(2,4-difluorophenoxy)-3-(4-ethoxy-1-methyl-6-oxo-1,6-dihydropyridin-3-yl)phenyl]-2-[3-(2-fluorophenyl)-1H-pyrazol-1-yl]acetamide Example 8 was prepared according to the procedure used for the preparation of Example 1H, substituting 2-[3-(2-fluorophenyl)-1H-pyrazol-1-yl]acetic acid for 2-(2-chloro-5-fluorophenyl)acetic acid to provide the title compound as a trifluoroacetate salt. $^1$H NMR (400 MHz, DMSO-d$_6$/D$_2$O) δ 7.93-7.85 (m, 2H), 7.60-7.51 (m, 3H), 7.42-7.26 (m, 3H), 7.25 (d, J=7.5 Hz, 1H), 7.07-6.88 (m, 3H), 6.69 (dd, J=3.8, 2.3 Hz, 1H), 5.82 (s, 1H), 5.09 (s, 2H), 3.92 (q, J=7.0 Hz, 2H), 3.36 (s, 3H), 1.13 (t, J=6.9 Hz, 3H). MS (APCI+) m/z 575.0 (M+H)$^+$.

Example 9

5-[2-(2,4-difluorophenoxy)-5-{[3-(1H-pyrazol-1-yl)propyl]amino}phenyl]-4-ethoxy-1-methylpyridin-2(1H)-one A stock solution of Example 1G (0.167 M in methanol, 392 μL, 0.065 mmol, 1.0 equivalent), acetic acid (4 M in methanol, 162 μL, 0.65 mmol, 10 equivalents), NaBH$_3$CN (0.6 M in methanol, 162 μL, 0.097 mmol, 1.5 equivalents) and 3-(1H-pyrazol-1-yl)propanal (0.40 M in DMA, 195 μL, 0.078 mmol, 1.2 equivalents) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 2.32 mL internal volume) set at 100° C., and passed through the reactor at 232 μL min$^{-1}$ (10 minute residence time). Upon exiting the reactor, the reaction was loaded directly into an injection loop and purified by preparative HPLC on a Phenomenex Luna C8(2) 5 um 100 Å AXIA column (50 mm×21.2 mm) eluting with a gradient of acetonitrile (A) and 0.1% trifluoroacetic acid in water (B) at a flow rate of 30 mL/min (0-0.5 min 5% A, 0.5-6.5 min linear gradient 5-100% A, 6.5-8.5 min 100% A, 8.5-9.0 min linear gradient 100-5% A, 9.0-10 min 5% A) to provide the title compound as the trifluoroacetate salt. $^1$H NMR (400 MHz, DMSO-d$_6$/D$_2$O) δ 7.64 (d, J=2.2 Hz, 1H), 7.41 (d, J=1.8 Hz, 1H), 7.36 (s, 1H), 7.11 (ddd, J=11.3, 8.6, 2.8 Hz, 1H), 6.91-6.76 (m, 3H), 6.60 (dd, J=8.7, 2.9 Hz, 1H), 6.51 (d, J=2.8 Hz, 1H), 6.22 (t, J=2.0 Hz, 1H), 5.74 (s, 1H), 4.21 (t, J=6.8 Hz, 2H), 3.90 (q, J=6.9 Hz, 2H), 3.03 (t, J=6.9 Hz, 2H), 2.07 (p, J=6.9 Hz, 2H), 1.15 (t, J=6.9 Hz, 3H). MS (APCI+) m/z 481.1 (M+H)$^+$.

Example 10

5-{2-(2,4-difluorophenoxy)-5-[(6,7-dihydro-5H-pyrrolo[1,2-a]imidazol-2-ylmethyl)amino]phenyl}-4-ethoxy-1-methylpyridin-2(1H)-one The trifluoroacetate salt of Example 10 was prepared according to the procedure used for the preparation of Example 9, substituting 6,7-dihydro-5H-pyrrolo[1,2-a]imidazole-2-carbaldehyde for 3-(1H-pyrazol-1-yl)propanal. $^1$H NMR (400 MHz, DMSO-d$_6$/D$_2$O) δ 7.41 (s, 1H), 7.35 (s, 1H), 7.13 (ddd, J=11.3, 8.6, 2.8 Hz, 1H), 6.93-6.77 (m, 3H), 6.71-6.58 (m, 2H), 5.75 (s, 1H), 4.30 (bs, 2H), 4.17 (t, J=7.2 Hz, 2H), 3.91 (q, J=6.9 Hz, 2H), 3.15-3.07 (m, 2H), 2.73-2.62 (m, 2H), 1.14 (t, J=6.9 Hz, 3H). MS (APCI+) m/z 493.1 (M+H)$^+$.

Example 11

5-[2-(2,4-difluorophenoxy)-5-{[(6-methylpyridin-2-yl)methyl]amino}phenyl]-4-ethoxy-1-methylpyridin-2(1H)-one The trifluoroacetate salt of Example 11 was prepared according to the procedure used for the preparation of Example 9, substituting 6-methylpicolinaldehyde for 3-(1H-pyrazol-1-yl)propanal. $^1$H NMR (400 MHz, DMSO-d$_6$/D$_2$O) δ 8.00 (t, J=7.7 Hz, 1H), 7.50 (d, J=7.8 Hz, 1H), 7.44 (d, J=7.8 Hz, 1H), 7.34 (s, 1H), 7.19-7.06 (m, 1H), 6.94-6.75 (m, 3H), 6.65 (dd, J=8.6, 2.9 Hz, 1H), 6.60 (d, J=2.9 Hz, 1H), 5.74 (s, 1H), 4.47 (s, 1H), 3.97-3.84 (m, 2H), 1.20-1.12 (m, 2H), 1.11 (d, J=6.9 Hz, 2H). MS (APCI+) m/z 478.1 (M+H)$^+$.

Example 12

5-[2-(2,4-difluorophenoxy)-5-{[(3-methylpyridin-2-yl)methyl]amino}phenyl]-4-ethoxy-1-methylpyridin-2(1H)-one The trifluoroacetate salt of Example 12 was prepared according to the procedure used for the preparation of Example 9, substituting 3-methylpicolinaldehyde for 3-(1H-pyrazol-1-yl)propanal. $^1$H NMR (400 MHz, DMSO-d$_6$/D$_2$O) δ 8.67-8.41 (m, 1H), 7.99-7.92 (m, 1H), 7.61-7.46 (m, 1H), 7.41-7.33 (m, 1H), 7.17-7.07 (m, 1H), 6.95-6.61 (m, 7H), 5.75 (s, 1H), 4.61-4.41 (m, 2H), 3.90 (q, J=7.0 Hz, 2H), 1.14 (t, J=6.9 Hz, 3H). MS (APCI+) m/z 478.1 (M+H)$^+$.

Example 13

5-[2-(2,4-difluorophenoxy)-5-{[(1-methyl-1H-pyrazol-5-yl)methyl]amino}phenyl]-4-ethoxy-1-methyl-pyridin-2(1H)-one The trifluoroacetate salt of Example 13 was prepared according to the procedure used for the preparation of Example 9, substituting 1-methyl-1H-pyrazole-5-carbaldehyde for 3-(1H-pyrazol-1-yl)propanal. $^1$H NMR (400 MHz, DMSO-d$_6$/D$_2$O) δ 7.35 (s, 1H), 7.29 (d, J=1.8 Hz, 1H), 7.11 (ddd, J=11.3, 8.6, 2.8 Hz, 1H), 6.92-6.73 (m, 2H), 6.69 (dd, J=8.7, 2.9 Hz, 1H), 6.62 (d, J=2.8 Hz, 1H), 6.19 (d, J=1.8 Hz, 1H), 5.74 (s, 1H), 4.29 (s, 1H), 3.90 (q, J=6.9 Hz, 1H), 3.80 (s, 2H), 1.16 (s, 1H), 1.14 (d, J=6.9 Hz, 2H). MS (APCI+) m/z 467.1 (M+H)$^+$.

Example 14 methyl 4-{[4-(2,4-difluorophenoxy)-3-(4-ethoxy-1-methyl-6-oxo-1,6-dihydropyridin-3-yl)phenyl]amino}butanoate The trifluoroacetate salt of Example 14 was prepared according to the procedure used for the preparation of Example 9, substituting methyl 4-oxobutanoate for 3-(1H-pyrazol-1-yl)propanal. $^1$H NMR (400 MHz, DMSO-d$_6$/D$_2$O) δ 7.36 (s, 1H), 7.11 (ddd, J=11.3, 8.6, 2.8 Hz, 1H), 6.91-6.77 (m, 3H), 6.62 (dd, J=8.7, 2.9 Hz, 1H), 6.53 (d, J=2.8 Hz, 1H), 5.74 (s, 1H), 3.91 (q, J=6.9 Hz, 2H), 3.60 (s, 3H), 3.06 (t, J=6.9 Hz, 2H), 2.40 (t, J=7.3 Hz, 2H), 1.83 (p, J=7.1 Hz, 2H), 1.16 (t, J=6.9 Hz, 3H). MS (APCI+) m/z 473.1 (M+H)$^+$.

Example 15

1-[4-(2,4-difluorophenoxy)-3-(4-ethoxy-1-methyl-6-oxo-1,6-dihydropyridin-3-yl)phenyl]-3-(3-phenoxyphenyl)urea A stock solution of Example 1G (0.73 M in pyridine, 458 μL, 0.033 mmol, 1.0 equivalent) and 1-isocyanato-3-phenoxybenzene (0.40 M in DMA, 108 μL, 0.043 mmol, 1.3 equivalents) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 2.32 mL internal volume) set at 100° C., and passed through the reactor at 232 μL min$^{-1}$ (10 minute residence time). Upon exiting the reactor, the reaction was loaded directly into an injection loop and purified by preparative HPLC on a Phenomenex Luna C8(2) 5 um 100 Å AXIA column (50 mm×21.2 mm). A gradient of acetonitrile (A) and 0.1% trifluoroacetic acid in water (B) was used, at a flow rate of 30 mL/min (0-0.5 min 5% A, 0.5-6.5 min linear gradient 30-70% A, 6.5-7.0 min linear gradient 70-100% A, 7.0-8.5 min 100% A, 8.5-9.0 min linear gradient 100-5% A, 9.0-10 min 5% A) to yield the title compound. $^1$H NMR (400 MHz, DMSO-d$_6$/D$_2$O) δ 7.56 (s, 1H), 7.45-7.37 (m, 3H), 7.39-7.22 (m, 4H), 7.20-7.12 (m, 1H), 7.11 (ddd, J=8.0, 2.0, 1.0 Hz, 1H), 7.05-6.92 (m, 4H), 6.89 (d, J=8.7 Hz, 1H), 6.63 (ddd, J=8.1, 2.4, 0.9 Hz, 1H), 5.82 (s, 1H), 3.92 (q, J=6.9 Hz, 2H), 3.36 (s, 3H), 1.13 (t, J=6.9 Hz, 3H). MS (APCI+) m/z 583.7 (M+H)$^+$.

Example 16

1-[4-(2,4-difluorophenoxy)-3-(4-ethoxy-1-methyl-6-oxo-1,6-dihydropyridin-3-yl)phenyl]-3-(2,4-dimethylphenyl)urea Example 16 was prepared according to the procedure used for the preparation of Example 15, substituting 1-isocyanato-2,4-dimethylbenzene 1-isocyanato-3-phenoxybenzene. $^1$H NMR (400 MHz, DMSO-d$_6$/D$_2$O) δ 7.60-7.53 (m, 2H), 7.45 (d, J=2.7 Hz, 1H), 7.41-7.27 (m, 2H), 7.10-6.91 (m, 5H), 6.90 (d, J=8.7 Hz, 1H), 5.82 (s, 1H), 3.92 (q, J=7.0 Hz, 2H), 3.37 (s, 3H), 2.25-2.18 (m, 8H), 1.14 (t, J=6.9 Hz, 3H). MS (APCI+) m/z 519.8 (M+H)$^+$.

Example 17

1-[4-(2,4-difluorophenoxy)-3-(4-ethoxy-1-methyl-6-oxo-1,6-dihydropyridin-3-yl)phenyl]-3-(3,5-dimethylphenyl)urea Example 17 was prepared according to the procedure used for the preparation of Example 15, substituting 1-isocyanato-3,5-dimethylbenzene for 1-isocyanato-3-phenoxybenzene. $^1$H NMR (400 MHz, DMSO-d$_6$/D$_2$O) δ 7.57 (s, 1H), 7.45 (d, J=2.7 Hz, 1H), 7.41-7.27 (m, 2H), 7.09-6.94 (m, 4H), 6.89 (d, J=8.8 Hz, 1H), 6.64 (s, 1H), 5.82 (s, 1H), 3.97-3.88 (m, 2H), 3.37 (s, 3H), 2.23 (s, 6H), 1.14 (t, J=6.9 Hz, 3H). MS (APCI+) m/z 519.8 (M+H)$^+$.

Example 18

1-[4-(2,4-difluorophenoxy)-3-(4-ethoxy-1-methyl-6-oxo-1,6-dihydropyridin-3-yl)phenyl]-3-[4-(trifluoromethoxy)phenyl]urea Example 18 was prepared according to the procedure used for the preparation of Example 15, substituting 1-isocyanato-4-(trifluoromethoxy)benzene for 1-isocyanato-3-phenoxybenzene. $^1$H NMR (400 MHz, DMSO-d$_6$/D$_2$O) δ 7.60-7.52 (m, 3H), 7.46-7.36 (m, 2H), 7.36-7.26 (m, 3H), 7.08-6.87 (m, 3H), 5.82 (s, 1H), 3.93 (q, J=7.0 Hz, 2H), 3.37 (s, 3H), 1.15 (t, J=6.9 Hz, 3H). MS (APCI+) m/z 576.0 (M+H)$^+$.

Example 19

1-[4-(2,4-difluorophenoxy)-3-(4-ethoxy-1-methyl-6-oxo-1,6-dihydropyridin-3-yl)phenyl]-3-(2,5-dimethylphenyl)urea Example 19 was prepared according to the procedure used for the preparation of Example 15, substituting 2-isocyanato-1,4-dimethylbenzene for 1-isocyanato-3-phenoxybenzene. $^1$H NMR (400 MHz, DMSO-d$_6$/D$_2$O) δ 7.62-7.56 (m, 2H), 7.47 (d, J=2.7 Hz, 1H), 7.40-7.26 (m, 2H), 7.10-6.92 (m, 3H), 6.90 (d, J=8.7 Hz, 1H), 6.80 (dd, J=7.5, 1.8 Hz, 1H), 5.82 (s, 1H), 3.93 (q, J=6.9 Hz, 2H), 3.37 (s, 3H), 2.24 (s, 3H), 2.19 (s, 3H), 1.14 (t, J=6.9 Hz, 3H). MS (APCI+) m/z 519.8 (M+H)$^+$.

Example 20

1-[4-(2,4-difluorophenoxy)-3-(4-ethoxy-1-methyl-6-oxo-1,6-dihydropyridin-3-yl)phenyl]-3-(4-fluorophenyl)urea Example 20 was prepared according to the procedure used for the preparation of Example 15, substituting 1-fluoro-4-isocyanatobenzene for 1-isocyanato-3-phenoxybenzene. $^1$H NMR (400 MHz, DMSO-d$_6$/D$_2$O) δ 7.57 (s, 1H), 7.50-7.27 (m, 5H), 7.17-7.08 (m, 2H), 7.06-6.93 (m, 2H), 6.90 (d, J=8.7 Hz, 1H), 5.82 (s, 1H), 3.93 (q, J=6.9 Hz, 2H), 3.37 (s, 3H), 1.14 (t, J=6.9 Hz, 3H). MS (APCI+) m/z 510.1 (M+H)$^+$.

Example 21

1-(3-chlorophenyl)-3-[4-(2,4-difluorophenoxy)-3-(4-ethoxy-1-methyl-6-oxo-1,6-dihydropyridin-3-yl)phenyl]urea Example 21 was prepared according to the procedure used for the preparation of Example 15, substituting 1-chloro-3-isocyanatobenzene for 1-isocyanato-3-phenoxybenzene. $^1$H NMR (400 MHz, DMSO-d$_6$/D$_2$O) δ 7.69 (t, J=2.0 Hz, 1H), 7.58 (s, 1H), 7.45 (d, J=2.7 Hz, 1H), 7.39 (dd, J=8.7, 2.7 Hz, 1H), 7.36-7.24 (m, 3H), 7.06-6.94 (m, 3H), 6.90 (d, J=8.7 Hz, 1H), 5.83 (s, 1H), 3.93 (q, J=6.9 Hz, 2H), 3.37 (s, 3H), 1.15 (t, J=6.9 Hz, 3H). MS (APCI+) m/z 526.1 (M+H)$^+$.

Example 22

1-[4-(2,4-difluorophenoxy)-3-(4-ethoxy-1-methyl-6-oxo-1,6-dihydropyridin-3-yl)phenyl]-3-(3-methoxyphenyl)urea Example 22 was prepared according to the procedure used for the preparation of Example 15, substituting 1-isocyanato-3-methoxybenzene for 1-isocyanato-3-phenoxybenzene. $^1$H NMR (400 MHz, DMSO-d$_6$/D$_2$O) δ 7.58 (s, 1H), 7.44 (d, J=2.7 Hz, 1H), 7.41-7.27 (m, 2H), 7.23-7.15 (m, 2H), 7.06-6.94 (m, 2H), 6.96-6.87 (m, 2H), 6.61-6.54 (m, 1H), 5.82 (s, 1H), 3.93 (q, J=6.9 Hz, 2H), 3.37 (s, 3H), 1.15 (t, J=6.9 Hz, 3H). MS (APCI+) m/z 522.1 (M+H)$^+$.

Example 23

5-{2-(2,4-difluorophenoxy)-5-[(1,3-oxazol-5-ylmethyl)amino]phenyl}-4-ethoxy-1-methylpyridin-2(1H)-one The trifluoroacetate salt of Example 23 was prepared according to the procedure used for the preparation of Example 9, substituting oxazole-5-carbaldehyde for 3-(1H-pyrazol-1-yl)propanal. $^1$H NMR (400 MHz, DMSO-d$_6$/D$_2$O) δ 8.14 (s, 1H), 7.35 (s, 1H), 7.11 (ddd, J=11.3, 8.6, 2.8 Hz, 1H), 7.01 (d, J=-0.9 Hz, 1H), 6.91-6.76 (m, 2H), 6.68 (dd, J=8.6, 2.9 Hz, 1H), 6.60 (d, J=2.9 Hz, 1H), 5.74 (s, 1H), 4.34 (s, 1H), 3.94-3.86 (m, 1H), 1.16 (s, 1H), 1.13 (d, J=6.9 Hz, 2H). MS (APCI+) m/z 454.1 (M+H)$^+$.

Example 24

5-[2-(2,4-difluorophenoxy)-5-{[(1-methyl-1H-imidazol-5-yl)methyl]amino}phenyl]-4-ethoxy-1-methylpyridin-2(1H)-one The trifluoroacetate salt of Example 24 was prepared according to the procedure used for the preparation of Example 9, substituting 1-methyl-1H-imidazole-5-carbaldehyde for 3-(1H-pyrazol-1-yl)propanal. $^1$H NMR (400 MHz, DMSO-d$_6$/D$_2$O) δ 8.86 (s, 1H), 7.47 (s, 1H), 7.36 (s, 1H), 7.12 (ddd, J=11.3, 8.6, 2.8 Hz, 1H), 6.93-6.77 (m, 3H), 6.72 (dd, J=8.7, 2.9 Hz, 1H), 6.65 (d, J=2.9 Hz, 1H), 5.75 (s, 1H), 4.38 (s, 2H), 3.94-3.88 (m, 2H), 3.87 (s, 3H), 1.14 (t, J=6.9 Hz, 3H). MS (APCI+) m/z 467.1 (M+H)$^+$.

Example 25

5-[2-(2,4-difluorophenoxy)-5-{[(1-ethyl-1H-pyrazol-3-yl)methyl]amino}phenyl]-4-ethoxy-1-methylpyridin-2(1H)-one The trifluoroacetate salt of Example 25 was prepared according to the procedure used for the preparation of Example 9, substituting 1-ethyl-1H-pyrazole-3-carbaldehyde for 3-(1H-pyrazol-1-yl)propanal. $^1$H NMR (400 MHz, DMSO-d$_6$/D$_2$O) δ 7.55 (d, J=2.2 Hz, 1H), 7.34 (s, 1H), 7.11 (ddd, J=11.3, 8.6, 2.8 Hz, 1H), 6.91-6.73 (m, 3H), 6.70 (dd, J=8.7, 2.8 Hz, 1H), 6.63 (d, J=2.8 Hz, 1H), 6.17 (d, J=2.2 Hz, 1H), 5.74 (s, 1H), 4.20 (s, 2H), 4.07 (q, J=7.2 Hz, 2H), 3.90 (q, J=6.9 Hz, 2H), 1.35 (t, J=7.2 Hz, 3H), 1.15 (t, J=6.9 Hz, 3H). MS (APCI+) m/z 481.1 (M+H)$^+$.

Example 26

N-[4-(2,4-difluorophenoxy)-3-(4-ethoxy-1-methyl-6-oxo-1,6-dihydropyridin-3-yl)phenyl]-5-oxo-5-phenylpentanamide Example 26 was prepared according to the procedure used for the preparation of Example 1H, substituting 5-oxo-5-phenylpentanoic acid for 2-(2-chloro-5-fluorophenyl)acetic acid. $^1$H NMR (400 MHz, DMSO-d$_6$/D$_2$O) δ 8.00-7.94 (m, 2H), 7.68-7.49 (m, 6H), 7.32 (ddd, J=11.2, 8.6, 2.7 Hz, 1H), 7.08-6.92 (m, 2H), 6.89 (d, J=8.7 Hz, 1H), 5.82 (s, 1H), 3.92 (q, J=7.0 Hz, 2H), 3.37 (s, 3H), 3.10 (t, J=7.1 Hz, 2H), 2.41 (t, J=7.3 Hz, 2H), 1.95 (p, J=7.2 Hz, 2H), 1.13 (t, J=6.9 Hz, 3H). MS (APCI+) m/z 547.0 (M+H)$^+$.

Example 27

N-[4-(2,4-difluorophenoxy)-3-(4-ethoxy-1-methyl-6-oxo-1,6-dihydropyridin-3-yl)phenyl]-3-(phenylsulfonyl)propanamide Example 27 was prepared according to the procedure used for the preparation of Example 1H, substituting 3-(phenylsulfonyl)propanoic acid for 2-(2-chloro-5-fluorophenyl)acetic acid. $^1$H NMR (400 MHz, DMSO-d$_6$/D$_2$O) δ 7.95-7.89 (m, 2H), 7.80-7.72 (m, 1H), 7.71-7.63 (m, 2H), 7.55 (s, 1H), 7.48-7.40 (m, 2H), 7.36-7.27 (m, 1H), 7.06-6.93 (m, 2H), 6.88 (d, J=8.5 Hz, 1H), 5.83 (s, 1H), 3.92 (q, J=6.9 Hz, 2H), 3.61 (t, J=7.2 Hz, 2H), 3.37 (s, 3H), 2.69 (t, J=7.2 Hz, 2H), 1.14 (t, J=6.9 Hz, 3H). MS (APCI+) m/z 568.9 (M+H)$^+$.

Example 28

N-[4-(2,4-difluorophenoxy)-3-(4-ethoxy-1-methyl-6-oxo-1,6-dihydropyridin-3-yl)phenyl]-2-(3-phenoxyphenyl)acetamide Example 28 was prepared according to the procedure used for the preparation of Example 1H, substituting 2-(3-phenoxyphenyl)acetic acid for 2-(2-chloro-5-fluorophenyl)acetic acid. $^1$H NMR (400 MHz, DMSO-d$_6$/D$_2$O) δ 10.30 (s, 1H), 7.58-7.47 (m, 3H), 7.44-7.27 (m, 4H), 7.19-7.08 (m, 2H), 7.10-6.92 (m, 5H), 6.92-6.85 (m, 2H), 5.82 (s, 1H), 3.92 (q, J=7.0 Hz, 2H), 3.62 (bs, 2H), 3.36 (s, 3H), 1.13 (t, J=6.9 Hz, 3H). MS (APCI+) m/z 582.9 (M+H)$^+$.

Example 29

N-[4-(2,4-difluorophenoxy)-3-(4-ethoxy-1-methyl-6-oxo-1,6-dihydropyridin-3-yl)phenyl]-2-[4-(methylsulfonyl)phenyl]acetamide Example 29 was prepared according to the procedure used for the preparation of Example 1H, substituting 4-(methylsulfonyl)phenylacetic acid for 2-(2-chloro-5-fluorophenyl) acetic acid. $^1$H NMR (400 MHz, DMSO-d$_6$/D$_2$O) δ 7.90 (s, 1H), 7.91-7.86 (m, 2H), 7.68-7.50 (m, 5H), 7.32 (ddd, J=11.2, 8.6, 2.7 Hz, 1H), 7.09-6.93 (m, 2H), 6.89 (d, J=8.6 Hz, 1H), 5.82 (s, 1H), 3.92 (q, J=6.9 Hz, 2H), 3.36 (s, 3H), 3.19 (s, 3H), 1.13 (t, J=6.9 Hz, 3H). MS (APCI+) m/z 568.9 (M+H)$^+$.

Example 30

N-[4-(2,4-difluorophenoxy)-3-(4-ethoxy-1-methyl-6-oxo-1,6-dihydropyridin-3-yl)phenyl]-3-phenoxypropanamide Example 30 was prepared according to the procedure used for the preparation of Example 1H, substituting 3-phenoxypropanoic acid for 2-(2-chloro-5-fluorophenyl)acetic acid. $^1$H NMR (400 MHz, DMSO-d$_6$/D$_2$O) δ 7.60 (d, J=2.4 Hz, 1H), 7.58-7.51 (m, 2H), 7.36-7.25 (m, 3H), 7.06-6.86 (m, 6H), 5.82 (s, 1H), 4.26 (t, J=5.8 Hz, 2H), 3.92 (q, J=6.9 Hz, 2H), 3.37 (s, 3H), 2.79 (t, J=5.8 Hz, 2H), 1.14 (t, J=6.9 Hz, 3H). MS (APCI+) m/z 521.0 (M+H)$^+$.

Example 31

N-[4-(2,4-difluorophenoxy)-3-(4-ethoxy-1-methyl-6-oxo-1,6-dihydropyridin-3-yl)phenyl]-2-(naphthalen-1-yl)acetamide Example 31 was prepared according to the procedure used for the preparation of Example 1H, substituting 2-(naphthalen-1-yl)acetic acid for 2-(2-chloro-5-fluorophenyl)acetic acid. $^1$H NMR (400 MHz, DMSO-d$_6$/D$_2$O) δ 8.13 (d, J=7.3 Hz, 1H), 8.00-7.82 (m, 2H), 7.63-7.45 (m, 7H), 7.31 (ddd, J=11.2, 8.6, 2.6 Hz, 1H), 7.06-6.93 (m, 2H), 6.89 (d, J=8.7 Hz, 1H), 5.81 (s, 1H), 4.14 (s, 2H), 3.91 (q, J=6.9 Hz, 2H), 3.35 (s, 3H), 1.12 (t, J=6.9 Hz, 3H). MS (APCI+) m/z 541.0 (M+H)$^+$.

Example 32

N-[4-(2,4-difluorophenoxy)-3-(4-ethoxy-1-methyl-6-oxo-1,6-dihydropyridin-3-yl)phenyl]-2-{[(4-methylphenyl)sulfonyl]amino}acetamide Example 32 was prepared according to the procedure used for the preparation of Example 1H, substituting 2-(4-methylphenylsulfonamido)acetic acid for 2-(2-chloro-5-fluorophenyl)acetic acid. $^1$H NMR (400 MHz, DMSO-d$_6$/D$_2$O) δ 9.97 (s, 1H), 7.74-7.68 (m, 2H), 7.55 (s, 1H), 7.48-7.27 (m, 5H), 7.06-6.93 (m, 2H), 6.91-6.84 (m, 1H), 5.83 (s, 1H), 3.93 (q, J=6.9 Hz, 2H), 3.37 (s, 3H), 2.34 (s, 3H), 1.14 (t, J=6.9 Hz, 3H). MS (APCI+) m/z 583.5 (M+H)$^+$.

Example 33

N-[4-(2,4-difluorophenoxy)-3-(4-ethoxy-1-methyl-6-oxo-1,6-dihydropyridin-3-yl)phenyl]-2-(4-methylphenoxy)acetamide Example 33 was prepared according to the procedure used for the preparation of Example 1H, substituting 2-(p-tolyloxy)acetic acid for 2-(2-chloro-5-fluorophenyl)acetic acid. $^1$H NMR (400 MHz, DMSO-d$_6$/D$_2$O) δ 10.15 (s, 1H), 7.62-7.55 (m, 3H), 7.37-7.28 (m, 1H), 7.15-7.09 (m, 2H), 7.09-6.94 (m, 2H), 6.93-6.87 (m, 3H), 5.83 (s, 1H), 4.64 (s, 2H), 3.93 (q, J=6.9 Hz, 2H), 3.37 (s, 3H), 2.24 (s, 3H), 1.14 (t, J=6.9 Hz, 3H). MS (APCI+) m/z 521.0 (M+H)$^+$.

Example 34

N-[4-(2,4-difluorophenoxy)-3-(4-ethoxy-1-methyl-6-oxo-1,6-dihydropyridin-3-yl)phenyl]-3-(2,3,4-trimethoxyphenyl)propanamide Example 34 was prepared according to the procedure used for the preparation of Example 1H, substituting 3-(2,3,4-trimethoxyphenyl)propanoic acid for 2-(2-chloro-5-fluorophenyl)acetic acid. $^1$H NMR (400 MHz, DMSO-d$_6$/D$_2$O) δ 7.60-7.49 (m, 4H), 7.32 (ddd, J=11.2, 8.6, 2.7 Hz, 1H), 7.08-6.84 (m, 5H), 6.72 (d, J=8.5 Hz, 1H), 5.82 (s, 1H), 3.92 (q, J=7.0 Hz, 3H), 3.37 (s, 4H), 2.82 (t, J=7.6 Hz, 3H), 1.14 (t, J=6.9 Hz, 3H). MS (APCI+) m/z 595.0 (M+H)$^+$.

Example 35

2-(benzyloxy)-N-[4-(2,4-difluorophenoxy)-3-(4-ethoxy-1-methyl-6-oxo-1,6-dihydropyridin-3-yl)phenyl]acetamide Example 35 was prepared according to the procedure used for the preparation of Example 1H, substituting 2-(benzyloxy)acetic acid for 2-(2-chloro-5-fluorophenyl)acetic acid. $^1$H NMR (400 MHz, DMSO-d$_6$/D$_2$O) δ 7.62-7.55 (m, 3H), 7.45-7.28 (m, 6H), 7.07-6.86 (m, 3H), 5.83 (s, 1H), 4.62 (s, 2H), 4.09 (s, 2H), 3.93 (q, J=6.9 Hz, 2H), 3.37 (s, 3H), 1.14 (t, J=6.9 Hz, 3H). MS (APCI+) m/z 521.0 (M+H)$^+$.

Example 36

2-(1,2-benzoxazol-3-yl)-N-[4-(2,4-difluorophenoxy)-3-(4-ethoxy-1-methyl-6-oxo-1,6-dihydropyridin-3-yl)phenyl]acetamide Example 36 was prepared according to the procedure used for the preparation of Example 1H, substituting 2-(benzo[d]isoxazol-3-yl)acetic acid for 2-(2-chloro-5-fluorophenyl) acetic acid to provide the title compound. $^1$H NMR (400 MHz, DMSO-d$_6$/D$_2$O) δ 7.90 (dt, J=7.9, 1.0 Hz, 1H), 7.78-7.71 (m, 1H), 7.68 (ddd, J=8.3, 7.0, 1.3 Hz, 1H), 7.61-7.50 (m, 3H), 7.42 (ddd, J=7.9, 6.9, 1.0 Hz, 1H), 7.37-7.28 (m, 1H), 7.07-6.94 (m, 2H), 6.91 (d, J=8.7 Hz, 1H), 5.82 (s, 1H), 4.16 (s, 2H), 3.92 (q, J=6.9 Hz, 2H), 3.36 (s, 3H), 1.13 (t, J=6.9 Hz, 3H). MS (APCI+) m/z 532.0 (M+H)$^+$.

Example 37

N-[4-(2,4-difluorophenoxy)-3-(4-ethoxy-1-methyl-6-oxo-1,6-dihydropyridin-3-yl)phenyl]-2-(4-phenoxyphenyl)acetamide Example 37 was prepared according to the procedure used for the preparation of Example 1H, substituting 4-phenoxyphenylacetic acid for 2-(2-chloro-5-fluorophenyl)acetic acid. $^1$H NMR (400 MHz, DMSO-$d_6$/$D_2O$) δ 7.60-7.51 (m, 3H), 7.44-7.24 (m, 5H), 7.18-7.10 (m, 1H), 7.06-6.93 (m, 6H), 6.89 (d, J=8.7 Hz, 1H), 5.82 (s, 1H), 3.92 (q, J=7.0 Hz, 2H), 3.62 (bs, 2H), 3.36 (s, 3H), 1.13 (t, J=6.9 Hz, 3H). MS (APCI+) m/z 582.9 (M+H)$^+$.

Example 38

N-[4-(2,4-difluorophenoxy)-3-(4-ethoxy-1-methyl-6-oxo-1,6-dihydropyridin-3-yl)phenyl]-4-phenylbutanamide Example 38 was prepared according to the procedure used for the preparation of Example 1H, substituting 4-phenylbutanoic acid for 2-(2-chloro-5-fluorophenyl)acetic acid. $^1$H NMR (400 MHz, DMSO-$d_6$/$D_2O$) δ 7.60-7.49 (m, 3H), 7.38-7.26 (m, 3H), 7.25-7.16 (m, 3H), 7.06-6.93 (m, 2H), 6.88 (d, J=8.7 Hz, 1H), 5.82 (s, 1H), 3.92 (q, J=6.9 Hz, 2H), 3.37 (s, 3H), 2.62 (t, J=7.6 Hz, 2H), 2.33 (t, J=7.3 Hz, 2H), 1.99-1.76 (m, 2H), 1.14 (t, J=6.9 Hz, 3H). MS (APCI+) m/z 519.0 (M+H)$^+$.

Example 39

N-[4-(2,4-difluorophenoxy)-3-(4-ethoxy-1-methyl-6-oxo-1,6-dihydropyridin-3-yl)phenyl]-2-(naphthalen-2-yl)acetamide Example 39 was prepared according to the procedure used for the preparation of Example 1H, substituting 2-(naphthalen-2-yl)acetic acid for 2-(2-chloro-5-fluorophenyl)acetic acid. $^1$H NMR (400 MHz, DMSO-$d_6$/$D_2O$) δ 7.96-7.85 (m, 3H), 7.85 (s, 1H), 7.63-7.46 (m, 6H), 7.36-7.27 (m, 1H), 7.06-6.92 (m, 2H), 6.89 (d, J=8.5 Hz, 1H), 5.81 (s, 1H), 3.91 (q, J=6.9 Hz, 2H), 3.35 (s, 3H), 1.12 (t, J=6.9 Hz, 3H). MS (APCI+) m/z 541.0 (M+H)$^+$.

Example 40

N-[4-(2,4-difluorophenoxy)-3-(4-ethoxy-1-methyl-6-oxo-1,6-dihydropyridin-3-yl)phenyl]-N'-phenylpentanediamide Example 40 was prepared according to the procedure used for the preparation of Example 1H, substituting 5-oxo-5-(phenylamino)pentanoic acid for 2-(2-chloro-5-fluorophenyl)acetic acid. $^1$H NMR (400 MHz, DMSO-$d_6$/$D_2O$) δ 7.63-7.50 (m, 5H), 7.37-7.26 (m, 3H), 7.12-6.93 (m, 3H), 6.89 (d, J=8.6 Hz, 1H), 5.83 (s, 1H), 3.93 (q, J=7.0 Hz, 2H), 3.37 (s, 3H), 2.39 (dd, J=7.4, 1.9 Hz, 4H), 2.38-2.35 (m, 2H), 1.99-1.85 (m, 2H), 1.14 (t, J=6.9 Hz, 3H). MS (APCI+) m/z 562.0 (M+H)$^+$.

Example 41

N-[4-(2,4-difluorophenoxy)-3-(4-ethoxy-1-methyl-6-oxo-1,6-dihydropyridin-3-yl)phenyl]-3-phenylpropanamide Example 41 was prepared according to the procedure used for the preparation of Example 1H, substituting 3-phenylpropanoic acid for 2-(2-chloro-5-fluorophenyl)acetic acid. $^1$H NMR (400 MHz, DMSO-$d_6$/$D_2O$) δ 10.05 (s, 1H), 7.60-7.48 (m, 3H), 7.40-7.21 (m, 5H), 7.24-7.16 (m, 1H), 7.08-6.93 (m, 2H), 6.88 (d, J=8.6 Hz, 1H), 5.82 (s, 1H), 3.92 (q, J=6.9 Hz, 2H), 3.37 (s, 3H), 2.92 (t, J=7.5 Hz, 2H), 2.63 (t, J=7.5 Hz, 2H), 1.14 (t, J=6.9 Hz, 3H). MS (APCI+) m/z 505.0 (M+H)$^+$.

Example 42

2-(biphenyl-4-yl)-N-[4-(2,4-difluorophenoxy)-3-(4-ethoxy-1-methyl-6-oxo-1,6-dihydropyridin-3-yl)phenyl]acetamide Example 42 was prepared according to the procedure used for the preparation of Example 1H, substituting 2-([1,1'-biphenyl]-4-yl)acetic acid for 2-(2-chloro-5-fluorophenyl)acetic acid. $^1$H NMR (400 MHz, DMSO-$d_6$/$D_2O$) δ 7.69-7.62 (m, 3H), 7.62 (d, J=0.5 Hz, 2H), 7.61-7.50 (m, 3H), 7.51-7.42 (m, 4H), 7.40-7.27 (m, 2H), 7.06-6.86 (m, 3H), 5.82 (s, 1H), 3.92 (q, J=7.0 Hz, 2H), 3.36 (s, 3H), 1.13 (t, J=6.9 Hz, 3H). MS (APCI+) m/z 567.0 (M+H)$^+$.

Example 43

N-[4-(2,4-difluorophenoxy)-3-(4-ethoxy-1-methyl-6-oxo-1,6-dihydropyridin-3-yl)phenyl]-4-oxo-4-phenylbutanamide Example 43 was prepared according to the procedure used for the preparation of Example 1H, substituting 4-oxo-4-phenylbutanoic acid for 2-(2-chloro-5-fluorophenyl)acetic acid. $^1$H NMR (400 MHz, DMSO-$d_6$/$D_2O$) δ 8.03-7.97 (m, 2H), 7.70-7.62 (m, 1H), 7.60-7.44 (m, 5H), 7.36-7.11 (m, 1H), 7.13-6.91 (m, 2H), 6.89 (d, J=8.7 Hz, 1H), 5.81 (s, 1H), 3.92 (q, J=7.0 Hz, 2H), 3.36 (s, 4H), 3.33 (d, J=6.2 Hz, 4H), 2.73 (t, J=6.2 Hz, 2H), 1.13 (t, J=6.9 Hz, 3H). MS (APCI+) m/z 533.0 (M+H)$^+$.

Example 44

N-[4-(2,4-difluorophenoxy)-3-(4-ethoxy-1-methyl-6-oxo-1,6-dihydropyridin-3-yl)phenyl]-4-phenoxybutanamide Example 44 was prepared according to the procedure used for the preparation of Example 1H, substituting 4-phenoxybutanoic acid for 2-(2-chloro-5-fluorophenyl)acetic acid. $^1$H NMR (400 MHz, DMSO-$d_6$/$D_2O$) δ 7.58-7.49 (m, 3H), 7.36-7.24 (m, 3H), 7.06-6.85 (m, 6H), 5.82 (s, 1H), 4.01 (t, J=6.2 Hz, 2H), 3.92 (q, J=6.9 Hz, 2H), 3.37 (s, 3H), 2.09-1.92 (m, 2H), 1.13 (t, J=6.9 Hz, 3H). MS (APCI+) m/z 535.0 (M+H)$^+$.

Example 45

2-[4-(benzyloxy)phenyl]-N-[4-(2,4-difluorophenoxy)-3-(4-ethoxy-1-methyl-6-oxo-1,6-dihydropyridin-3-yl)phenyl]acetamide Example 45 was prepared according to the procedure used for the preparation of Example 1H, substituting 2-(4-(benzyloxy)phenyl)acetic acid for 2-(2-chloro-5-fluorophenyl)acetic acid. $^1$H NMR (400 MHz, DMSO-$d_6$/$D_2O$) δ 7.61-7.49 (m, 3H), 7.50-7.35 (m, 4H), 7.37-7.27 (m, 2H), 7.29-7.22 (m, 2H), 7.06-6.93 (m, 4H), 6.88 (d, J=8.6 Hz, 1H), 5.82 (s, 1H), 5.09 (s, 2H), 3.91 (q, J=6.9 Hz, 2H), 3.54 (bs, 2H), 3.36 (s, 3H), 1.13 (t, J=6.9 Hz, 3H). MS (APCI+) m/z 597.0 (M+H)$^+$.

Example 46

N-[4-(2,4-difluorophenoxy)-3-(4-ethoxy-1-methyl-6-oxo-1,6-dihydropyridin-3-yl)phenyl]-2-(2-methoxyphenyl)acetamide Example 46 was prepared according to the procedure used for the preparation of Example 1H, substituting -2-(2-methoxyphenyl)acetic acid for 2-(2-chloro-5-fluorophenyl)acetic acid. $^1$H NMR (400 MHz, DMSO-$d_6$/D$_2$O) δ 7.59-7.50 (m, 3H), 7.37-7.15 (m, 3H), 7.06-6.85 (m, 5H), 5.82 (s, 1H), 3.92 (q, J=7.0 Hz, 2H), 3.62 (s, 2H), 3.36 (s, 3H), 1.14 (t, J=6.9 Hz, 3H). MS (APCI+) m/z 521.0 (M+H)$^+$.

Example 47

N-(2-{[4-(2,4-difluorophenoxy)-3-(4-ethoxy-1-methyl-6-oxo-1,6-dihydropyridin-3-yl)phenyl]amino}-2-oxoethyl)benzamide Example 47 was prepared according to the procedure used for the preparation of Example 1H, substituting 2-benzamidoacetic acid for 2-(2-chloro-5-fluorophenyl)acetic acid. $^1$H NMR (400 MHz, DMSO-$d_6$/D$_2$O) δ 7.92-7.86 (m, 2H), 7.63-7.47 (m, 6H), 7.37-7.27 (m, 1H), 7.07-6.94 (m, 2H), 6.91 (d, J=8.4 Hz, 1H), 5.83 (s, 1H), 4.06 (s, 2H), 3.92 (q, J=7.0 Hz, 2H), 3.37 (s, 3H), 1.14 (t, J=6.9 Hz, 3H). MS (APCI+) m/z 534.0 (M+H)$^+$.

Example 48

2-cyclohexyl-N-[4-(2,4-difluorophenoxy)-3-(4-ethoxy-1-methyl-6-oxo-1,6-dihydropyridin-3-yl)phenyl]acetamide Example 48 was prepared according to the procedure used for the preparation of Example 1H, substituting 2-cyclohexylacetic acid for 2-(2-chloro-5-fluorophenyl)acetic acid. $^1$H NMR (400 MHz, DMSO-$d_6$/D$_2$O) δ 7.59-7.49 (m, 3H), 7.32 (ddd, J=11.2, 8.6, 2.7 Hz, 1H), 7.06-6.91 (m, 2H), 6.88 (d, J=8.7 Hz, 1H), 5.82 (s, 1H), 3.92 (q, J=7.0 Hz, 2H), 3.37 (s, 3H), 2.18 (d, J=7.0 Hz, 2H), 1.82-1.55 (m, 6H), 1.29-1.06 (m, 6H), 1.06-0.89 (m, 2H). MS (APCI+) m/z 497.1 (M+H)$^+$.

Example 49

2-[(1S,4R)-bicyclo[2.2.1]hept-2-yl]-N-[4-(2,4-difluorophenoxy)-3-(4-ethoxy-1-methyl-6-oxo-1,6-dihydropyridin-3-yl)phenyl]acetamide Example 49 was prepared according to the procedure used for the preparation of Example 1H, substituting 2-((1S,4R)-bicyclo[2.2.1]heptan-2-yl)acetic acid for 2-(2-chloro-5-fluorophenyl)acetic acid. $^1$H NMR (400 MHz, DMSO-$d_6$/D$_2$O) δ 9.99 (s, 1H), 7.60-7.49 (m, 3H), 7.32 (ddd, J=11.2, 8.6, 2.7 Hz, 1H), 7.06-6.93 (m, 2H), 6.88 (d, J=8.7 Hz, 1H), 5.82 (s, 1H), 3.92 (q, J=7.0 Hz, 2H), 3.37 (s, 3H), 2.26 (dd, J=13.9, 8.0 Hz, 1H), 2.22-2.05 (m, 2H), 2.00-1.95 (m, 1H), 1.93-1.84 (m, 1H), 1.54-1.31 (m, 4H), 1.32-1.03 (m, 7H). MS (APCI+) m/z 509.1 (M+H)$^+$.

Example 50

5-[5-{[2-(benzyloxy)-3-methoxybenzyl]amino}-2-(2,4-difluorophenoxy)phenyl]-4-ethoxy-1-methylpyridin-2(1H)-one Example 50 was prepared according to the procedure used for the preparation of Example 9, substituting 2-(benzyloxy)-3-methoxybenzaldehyde for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-$d_6$/D$_2$O) δ 7.45-7.39 (m, 3H), 7.39-7.27 (m, 3H), 7.22 (ddd, J=11.3, 8.6, 2.9 Hz, 1H), 7.09-7.01 (m, 1H), 7.02-6.96 (m, 1H), 6.96-6.88 (m, 2H), 6.83-6.71 (m, 2H), 6.48-6.41 (m, 2H), 5.75 (s, 1H), 5.01 (s, 2H), 4.13 (bs, 2H), 3.85 (s, 4H), 3.88-3.80 (m, 5H), 3.31 (s, 3H), 1.06 (t, J=6.9 Hz, 3H). MS (APCI+) m/z 598.9 (M+H)$^+$.

Example 51

5-[5-{[4-(benzyloxy)benzyl]amino}-2-(2,4-difluorophenoxy)phenyl]-4-ethoxy-1-methylpyridin-2(1H)-one Example 51 was prepared according to the procedure used for the preparation of Example 9, substituting 4-(benzyloxy)benzaldehyde for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-$d_6$/D$_2$O) δ 7.47-7.36 (m, 4H), 7.34 (d, J=7.0 Hz, 1H), 7.33-7.27 (m, 2H), 7.27-7.18 (m, 1H), 7.01-6.88 (m, 2H), 6.84-6.74 (m, 1H), 6.59 (dd, J=8.7, 2.9 Hz, 1H), 6.52 (d, J=2.8 Hz, 1H), 5.75 (s, 1H), 5.08 (s, 1H), 4.17 (bs, 1H), 3.85 (q, J=6.9 Hz, 1H), 3.32 (s, 2H), 1.10 (s, 1H), 1.07 (d, J=6.9 Hz, 3H). MS (APCI+) m/z 568.9 (M+H)$^+$.

Example 52

5-{5-[(4-tert-butylbenzyl)amino]-2-(2,4-difluorophenoxy)phenyl}-4-ethoxy-1-methylpyridin-2(1H)-one Example 52 was prepared according to the procedure used for the preparation of Example 9, substituting 4-(tert-butyl)benzaldehyde for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-$d_6$/D$_2$O) δ 7.45 (s, 1H), 7.39-7.18 (m, 5H), 6.97-6.88 (m, 1H), 6.85-6.75 (m, 2H), 6.60 (dd, J=8.7, 2.9 Hz, 1H), 6.53 (d, J=2.8 Hz, 1H), 5.75 (s, 1H), 4.20 (bs, 2H), 3.85 (q, J=7.0 Hz, 2H), 3.32 (s, 3H), 1.27 (s, 9H), 1.08 (t, J=6.9 Hz, 3H). MS (APCI+) m/z 519.1 (M+H)$^+$.

Example 53

5-{5-[(2,6-difluorobenzyl)amino]-2-(2,4-difluorophenoxy)phenyl}-4-ethoxy-1-methylpyridin-2(1H)-one Example 53 was prepared according to the procedure used for the preparation of Example 9, substituting 2,6-difluorobenzaldehyde for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-$d_6$/D$_2$O) δ 7.49-7.36 (m, 2H), 7.23 (ddd, J=11.3, 8.6, 2.9 Hz, 1H), 7.11 (t, J=7.8 Hz, 2H), 6.98-6.88 (m, 1H), 6.86-6.77 (m, 2H), 6.69 (dd, J=8.7, 2.9 Hz, 1H), 6.61 (d, J=2.8 Hz, 1H), 5.77 (s, 1H), 4.26 (bs, 2H), 3.87 (q, J=7.0 Hz, 2H), 3.33 (s, 3H), 1.10 (t, J=6.9 Hz, 3H). MS (APCI+) m/z 499.0 (M+H)$^+$.

Example 54

5-[2-(2,4-difluorophenoxy)-5-{[3-(4-methoxy phenoxy)benzyl]amino}phenyl]-4-ethoxy-1-methylpyridin-2(1H)-one Example 54 was prepared according to the procedure used for the preparation of Example 9, substituting 3-(4-methoxyphenoxy)benzaldehyde for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-d$_6$/D$_2$O) δ 7.43 (s, 1H), 7.34-7.19 (m, 1H), 7.12-7.06 (m, 1H), 6.97-6.90 (m, 4H), 6.85-6.73 (m, 2H), 6.56 (dd, J=8.7, 2.9 Hz, 1H), 6.50 (d, J=2.8 Hz, 1H), 5.76 (s, 1H), 4.24 (bs, 1H), 3.85 (q, J=7.0 Hz, 1H), 3.32 (s, 3H), 1.07 (t, J=6.9 Hz, 3H). MS (APCI+) m/z 584.9 (M+H)$^+$.

Example 55

5-[5-({[5-(2-chlorophenyl)furan-2-yl]methyl}amino)-2-(2,4-difluorophenoxy)phenyl]-4-ethoxy-1-methylpyridin-2(1H)-one Example 55 was prepared according to the procedure used for the preparation of Example 9, substituting 5-(2-chlorophenyl)furan-2-carbaldehyde for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-d$_6$/D$_2$O) δ 7.80 (dd, J=7.8, 1.7 Hz, 1H), 7.54 (dd, J=7.9, 1.3 Hz, 1H), 7.47 (s, 1H), 7.41 (td, J=7.6, 1.3 Hz, 1H), 7.32 (td, J=7.6, 1.7 Hz, 1H), 7.24 (ddd, J=11.3, 8.6, 2.9 Hz, 1H), 7.08 (d, J=3.4 Hz, 1H), 6.97-6.88 (m, 1H), 6.87-6.78 (m, 2H), 6.73 (dd, J=8.7, 2.9 Hz, 1H), 6.65 (d, J=2.8 Hz, 1H), 6.50 (d, J=3.4 Hz, 1H), 5.76 (s, 1H), 4.34 (bs, 2H), 3.85 (q, J=7.0 Hz, 2H), 3.32 (s, 3H), 1.08 (t, J=6.9 Hz, 3H). MS (APCI+) m/z 562.9 (M+H)$^+$.

Example 56

4-({[4-(2,4-difluorophenoxy)-3-(4-ethoxy-1-methyl-6-oxo-1,6-dihydropyridin-3-yl)phenyl]amino}methyl)benzonitrile Example 56 was prepared according to the procedure used for the preparation of Example 9, substituting 4-formylbenzonitrile for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-d$_6$/D$_2$O) δ 7.82-7.76 (m, 1H), 7.61-7.54 (m, 1H), 7.45 (s, 1H), 7.23 (ddd, J=11.4, 8.6, 2.9 Hz, 1H), 6.97-6.87 (m, 1H), 6.84-6.75 (m, 1H), 6.56 (dd, J=8.7, 2.9 Hz, 1H), 6.50 (d, J=2.8 Hz, 1H), 5.75 (s, 1H), 4.37 (bs, 1H), 3.84 (q, J=6.9 Hz, 1H), 3.32 (s, 2H), 1.06 (t, J=6.9 Hz, 3H). MS (APCI+) m/z 488.0 (M+H)$^+$.

Example 57

2-({[4-(2,4-difluorophenoxy)-3-(4-ethoxy-1-methyl-6-oxo-1,6-dihydropyridin-3-yl)phenyl]amino}methyl)benzonitrile Example 57 was prepared according to the procedure used for the preparation of Example 9, substituting 2-formylbenzonitrile for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-d$_6$/D$_2$O) δ 7.83 (d, J=7.7 Hz, 1H), 7.74-7.66 (m, 1H), 7.61 (d, J=7.8 Hz, 1H), 7.52-7.45 (m, 1H), 7.28-7.19 (m, 1H), 6.97-6.89 (m, 1H), 6.86-6.77 (m, 1H), 6.60 (dd, J=8.6, 2.9 Hz, 1H), 6.56 (d, J=2.9 Hz, 1H), 5.76 (s, 1H), 4.43 (bs, 1H), 3.86 (q, J=7.0 Hz, 1H), 3.33 (s, 2H), 1.08 (t, J=6.9 Hz, 3H). MS (APCI+) m/z 488.0 (M+H)$^+$.

Example 58

5-{2-(2,4-difluorophenoxy)-5-[(quinolin-4-ylmethyl)amino]phenyl}-4-ethoxy-1-methylpyridin-2(1H)-one Example 58 was prepared according to the procedure used for the preparation of Example 9, substituting quinoline-4-carbaldehyde for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-d$_6$/D$_2$O) δ 8.84 (d, J=4.4 Hz, 1H), 8.26 (d, J=8.4 Hz, 1H), 8.07 (d, J=8.5 Hz, 1H), 7.85-7.77 (m, 1H), 7.72-7.64 (m, 1H), 7.54 (d, J=4.5 Hz, 1H), 7.47 (s, 1H), 7.23 (ddd, J=11.4, 8.6, 2.9 Hz, 1H), 6.98-6.88 (m, 1H), 6.86-6.77 (m, 1H), 6.63 (dd, J=8.7, 2.9 Hz, 1H), 6.59 (d, J=2.8 Hz, 1H), 5.73 (s, 1H), 4.81 (bs, 1H), 3.83 (q, J=6.9 Hz, 1H), 3.31 (s, 2H), 1.05 (t, J=6.9 Hz, 3H). MS (APCI+) m/z 514.0 (M+H)$^+$.

Example 59

5-[5-{[(5-chloro-3-methyl-1-phenyl-1H-pyrazol-4-yl)methyl]amino}-2-(2,4-difluorophenoxy)phenyl]-4-ethoxy-1-methylpyridin-2(1H)-one Example 59 was prepared according to the procedure used for the preparation of Example 9, substituting 5-chloro-3-methyl-1-phenyl-1H-pyrazole-4-carbaldehyde for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-d$_6$/D$_2$O) δ 7.60-7.44 (m, 4H), 7.29-7.19 (m, 1H), 6.99-6.90 (m, 1H), 6.89-6.80 (m, 1H), 6.69 (dd, J=8.7, 2.8 Hz, 1H), 6.60 (d, J=2.8 Hz, 1H), 5.77 (s, 2H), 4.06 (bs, 1H), 3.87 (q, J=6.9 Hz, 2H), 3.33 (s, 3H), 2.29 (s, 3H), 1.10 (d, J=6.9 Hz, 3H). MS (APCI+) m/z 577.0 (M+H)$^+$.

Example 60

5-{2-(2,4-difluorophenoxy)-5-[({5-[2-(trifluoromethyl)phenyl]furan-2-yl}methyl)amino]phenyl}-4-ethoxy-1-methylpyridin-2(1H)-one Example 60 was prepared according to the procedure used for the preparation of Example 9, substituting 5-(2-(trifluoromethyl)phenyl)furan-2-carbaldehyde for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-d$_6$/D$_2$O) δ 7.86-7.75 (m, 1H), 7.76-7.68 (m, 1H), 7.61-7.53 (m, 1H), 7.46 (s, 1H), 7.28-7.19 (m, 1H), 6.97-6.88 (m, 1H), 6.87-6.79 (m, 1H), 6.77-6.68 (m, 1H), 6.62 (d, J=2.8 Hz, 1H), 6.48 (d, J=3.4 Hz, 1H), 5.76 (s, 1H), 4.32 (bs, 1H), 3.85 (q, J=7.0 Hz, 1H), 3.32 (s, 2H), 1.10 (s, 1H), 1.07 (d, J=6.9 Hz, 2H). MS (APCI+) m/z 597.0 (M+H)⁺.

Example 61

5-{5-[(4-butoxybenzyl)amino]-2-(2,4-difluorophenoxy)phenyl}-4-ethoxy-1-methylpyridin-2(1H)-one Example 61 was prepared according to the procedure used for the preparation of Example 9, substituting 4-butoxybenzaldehyde for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-$d_6$/D$_2$O) δ 7.45 (s, 1H), 7.32-7.14 (m, 3H), 6.91 (dd, J=20.3, 8.8 Hz, 3H), 6.84-6.70 (m, 2H), 6.59 (dd, J=8.8, 2.8 Hz, 1H), 6.52 (d, J=2.9 Hz, 1H), 5.75 (s, 1H), 4.17 (s, 2H), 3.94 (t, J=6.4 Hz, 2H), 3.85 (q, J=7.0 Hz, 2H), 3.32 (s, 3H), 1.74-1.57 (m, 2H), 1.51-1.32 (m, 2H), 1.08 (t, J=7.0 Hz, 3H), 0.92 (t, J=7.4 Hz, 3H). MS (APCI+) m/z 535.1 (M+H)⁺.

Example 62

5-{2-(2,4-difluorophenoxy)-5-[(4-phenoxybenzyl)amino]phenyl}-4-ethoxy-1-methylpyridin-2(1H)-one Example 62 was prepared according to the procedure used for the preparation of Example 9, substituting 4-phenoxybenzaldehyde for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-$d_6$/D$_2$O) δ 7.48-7.35 (m, 5H), 7.28-7.18 (m, 1H), 7.14 (t, J=7.4 Hz, 1H), 7.02-6.88 (m, 5H), 6.85-6.76 (m, 2H), 6.61 (dd, J=8.7, 2.8 Hz, 1H), 6.54 (d, J=2.8 Hz, 1H), 5.76 (s, 1H), 4.24 (bs, 2H), 3.86 (q, J=6.9 Hz, 2H), 3.33 (s, 3H), 1.09 (t, J=6.9 Hz, 3H). MS (APCI+) m/z 555.0 (M+H)⁺.

Example 63

3-({[4-(2,4-difluorophenoxy)-3-(4-ethoxy-1-methyl-6-oxo-1,6-dihydropyridin-3-yl)phenyl]amino}methyl)benzonitrile Example 63 was prepared according to the procedure used for the preparation of Example 9, substituting 3-formylbenzonitrile for 3-(1H-pyrazol-1-yl)propanal and eluting with a gradient of acetonitrile (A) and 0.1% ammonium acetate in water (B) in place of acetonitrile (A) and 0.1% trifluoroacetic acid in water (B). $^1$H NMR (400 MHz, DMSO-$d_6$/D$_2$O) δ 7.79 (s, 1H), 7.76-7.68 (m, 1H), 7.56 (t, J=7.7 Hz, 1H), 7.45 (s, 1H), 7.23 (ddd, J=11.3, 8.6, 2.8 Hz, 1H), 6.97-6.88 (m, 1H), 6.85-6.75 (m, 1H), 6.58 (dd, J=8.7, 2.9 Hz, 1H), 6.53 (d, J=2.8 Hz, 1H), 5.75 (s, 1H), 4.33 (bs, 1H), 3.85 (q, J=6.9 Hz, 1H), 3.33 (s, 2H), 1.07 (t, J=6.9 Hz, 3H). MS (APCI+) m/z 488.0 (M+H)⁺.

Example 64

5-{2-(2,4-difluorophenoxy)-5-[(4-fluorobenzyl)amino]phenyl}-4-ethoxy-1-methylpyridin-2(1H)-one A flask with stir bar and condenser was charged with Example 1G (0.255 g, 0.685 mmol), 4-fluorobenzaldehyde (150 μL, 1.398 mmol) and acetic acid (0.40 mL, 6.99 mmol) in dichloromethane (7 mL). The solution was heated to 60° C. for 1 hour, and then cooled in an ice bath. Sodium triacetoxyhydroborate (0.293 g, 1.382 mmol) was added in three portions over 30 minutes, and the mixture was allowed to warm to ambient temperature overnight. The reaction mixture was partitioned between dichloromethane and aqueous sodium carbonate and the organics dried over anhydrous sodium sulfate. After filtration and solvent removal, the residues were chromatographed on 12 g silica cartridge eluting with 0-100% ethyl acetate/heptane to provide the title compound. $^1$H NMR (300 MHz, DMSO-$d_6$) δ 7.49 (s, 1H), 7.42 (m, 2H), 7.24 (m, 1H), 7.17 (m, 2H), 6.91 (m, 1H), 6.88 (m, 2H), 6.54 (m, 2H), 6.21 (t, J=6.0 Hz, 1H), 5.71 (s, 1H), 4.24 (d, J=5.9 Hz, 2H), 3.84 (q, J=7.0 Hz, 2H), 2.49 (s, 3H), 1.06 (t, J=7.0 Hz, 3H). MS (ESI) 481.2 (M+H)⁺.

Example 65

5-{5-[(cyclopropylmethyl)amino]-2-(2,4-difluorophenoxy)phenyl}-4-ethoxy-1-methylpyridin-2(1H)-one Example 65 was prepared according to the procedure used for the preparation of Example 64, substituting cyclopropanecarbaldehyde for 4-fluorobenzaldehyde. $^1$H NMR (300 MHz, DMSO-$d_6$) δ 7.49 (s, 1H), 7.23 (m, 1H), 6.93 (m, 1H), 6.79 (m, 2H), 6.60-6.42 (m, 3H), 5.72 (s, 1H), 5.62 (t, J=5.7 Hz, 1H), 3.85 (q, J=7.0 Hz, 2H), 2.88 (t, J=6.1 Hz, 2H), 2.26 (s, 3H), 1.02 (t, J=7.0 Hz, 3H), 0.83 (m, 1H), 0.45 (m, 2H), 0.18 (m, 2H). MS (ESI) 427.2 (M+H)⁺.

Example 66

1-(2-chloro-5-fluorophenyl)-N-(cyclopropylmethyl)-N-[4-(2,4-difluorophenoxy)-3-(4-ethoxy-1-methyl-6-oxo-1,6-dihydropyridin-3-yl)phenyl]methanesulfonamide A vial with stir bar was charged with Example 65 (0.0426 g, 0.100 mmol), 2-chloro-5-fluorophenyl)methanesulfonyl chloride (0.048 g, 0.197 mmol) and triethylamine (50 μL, 0.359 mmol) in dichloromethane (1.0 mL). The mixture was stirred for 40 hours at ambient temperature. The reaction mixture was diluted with 30 mL of dichloromethane, washed with aqueous ammonium chloride, dried over sodium sulfate, filtered, concentrated, and then purified by reverse phase HPLC (C18, CH$_3$CN/water (0.1% TFA), 0-100%) to afford the title compound. $^1$H NMR (300 MHz, DMSO-$d_6$) δ 7.62 (s, 1H), 7.55 (dd, J=8.9, 5.2 Hz, 1H), 7.48-7.22 (m, 5H), 7.16-7.07 (m, 2H), 7.11 (d, J=6.2 Hz, 1H), 6.86 (d, J=8.6 Hz, 1H), 5.68 (s, 1H), 4.68 (s, 2H), 3.95 (q, J=7.0 Hz, 2H), 3.56 (d, J=7 Hz, 2H), 3.38 (s, 3H), 1.15 (t, J=6.9 Hz, 3H), 0.89 (m, 1H), 0.41 (m, 2H), 0.09 (m, 2H). MS (ESI) 633.1 (M+H)⁺.

Example 67

2-(2-chloro-5-fluorophenyl)-N-(cyclopropylmethyl)-N-[4-(2,4-difluorophenoxy)-3-(4-ethoxy-1-methyl-6-oxo-1,6-dihydropyridin-3-yl)phenyl]acetamide A flask with stir bar was charged with Example 65 (0.079 g, 0.185 mmol), 2-(2-chloro-5-fluorophenyl)acetyl chloride (0.094 g, 0.454 mmol) and triethylamine (100 μL, 0.717 mmol) in dichloromethane (1.0 mL). The mixture was stirred overnight at ambient temperature, diluted with 30 mL of dichloromethane, washed with aqueous sodium bicarbonate, dried over anhydrous sodium sulfate, filtered, concentrated, and then purified by reverse phase HPLC (C18, CH$_3$CN/water (0.1% TFA), 0-100%) to afford the title compound. $^1$H NMR (300 MHz, DMSO-d$_6$) δ 7.62 (s, 1H), 7.46-7.27 (m, 5H), 7.25-6.92 (m, 4H), 5.82 (s, 1H), 3.92 (q, J=7.0 Hz, 2H), 3.54 (s, 2H), 3.52 (d, J=9.0 Hz, 2H), 3.37 (s, 3H), 1.11 (t, J=7.0 Hz, 3H), 0.88 (m, 1H), 0.41 (m, 2H), 0.08 (m, 2H). MS (ESI) 597.2 (M+H)$^+$.

Example 68

N-[4-(benzyloxy)benzyl]-2-(2-chloro-5-fluorophenyl)-N-[4-(2,4-difluorophenoxy)-3-(4-ethoxy-1-methyl-6-oxo-1,6-dihydropyridin-3-yl)phenyl]acetamide Example 68 was prepared according to the procedure used for the preparation of Example 67, substituting Example 51 for Example 65. $^1$H NMR (300 MHz, DMSO-d$_6$) δ 7.52 (s, 1H), 7.50-7.00 (m, 15H), 6.97-6.83 (m, 3H), 5.80 (s, 1H), 5.06 (s, 2H), 4.80 (bds, 2H), 3.90 (q, J=7.0 Hz, 2H), 3.54 (s, 2H), 3.35 (s, 3H), 1.09 (t, J=6.9 Hz, 3H). MS (ESI) 739.2 (M+H)$^+$.

Example 69

2-(2-chloro-5-fluorophenyl)-N-[4-(2,4-difluorophenoxy)-3-(4-ethoxy-1-methyl-6-oxo-1,6-dihydropyridin-3-yl)phenyl]-N-(4-fluorobenzyl)acetamide Example 69 was prepared according to the procedure used for the preparation of Example 67, substituting Example 64 for Example 65. $^1$H NMR (300 MHz, DMSO-d$_6$) δ 7.54 (s, 1H), 7.49-7.33 (m, 2H), 7.34-7.01 (m, 10H), 6.88 (d, J=8.6 Hz, 1H), 5.80 (s, 1H), 4.86 (bds, 2H), 3.90 (d, J=7.0 Hz, 2H), 3.36 (s, 3H), 1.08 (t, J=6.9 Hz, 3H). MS (ESI) 651.2 (M+H)$^+$.

Example 70

2-(2-chloro-5-fluorophenyl)-N-[4-(2,4-difluorophenoxy)-3-(4-ethoxy-1-methyl-6-oxo-1,6-dihydropyridin-3-yl)phenyl]propanamide A 4 mL vial with stir bar was charged with sodium hydride, dry 95% (2.9 mg, 0.115 mmol), placed in an ice bath and charged with a solution of Example 1H (0.0527 g, 0.097 mmol) in DMF (1 mL). After stirring 10 min at 0° C., iodomethane (8 μL, 0.128 mmol) was added by syringe. After 1 hour, the mixture was partitioned between 25 mL each of ethyl acetate and aqueous ammonium chloride. The organics were dried over anhydrous sodium sulfate. After filtration and solvent removal, the material was purified by reverse phase HPLC (C18, CH$_3$CN/water (0.1% TFA), 0-100%) to afford the title compound. $^1$H NMR (400 MHz, DMSO-d$_6$) δ 10.26 (s, 1H), 7.60 (d, J=2.6 Hz, 1H), 7.58 (s, 1H), 7.54-7.49 (m, 2H), 7.46-7.25 (m, 2H), 7.22-6.92 (m, 3H), 6.87 (d, J=8.8 Hz, 1H), 5.79 (s, 1H), 4.15 (q, J=7.1 Hz, 1H), 3.93 (d, J=7.0 Hz, 2H), 3.34 (s, 3H), 1.47 (d, J=7.1 Hz, 3H), 1.14 (t, J=6.9 Hz, 3H). MS (ESI) 557.1 (M+H)$^+$.

Example 71

2-(2-chloro-5-fluorophenyl)-N-[4-(2,4-difluorophenoxy)-3-(4-ethoxy-1-methyl-6-oxo-1,6-dihydropyridin-3-yl)phenyl]-N-methylacetamide A 4 mL vial with stir bar was charged with Example 1H (0.0626 g, 0.115 mmol), powdered sodium hydroxide (25.1 mg, 0.628 mmol), tetrabutylammonium bromide (16.3 mg, 0.051 mmol), iodomethane (100 μL, 1.599 mmol) and dichloromethane (1 mL). The mixture was stirred at ambient temperature for 2 hours. The mixture was partitioned between 30 mL each of dichloromethane and 1 M HCl. The organics were dried over sodium sulfate. After filtration and solvent removal, the residues were purified by HPLC (C18, CH$_3$CN/water (0.1% TFA), 0-100%) to afford the title compound. $^1$H NMR (400 MHz, DMSO-d$_6$) δ 7.64 (s, 1H), 7.47-7.33 (m, 4H), 7.26-7.03 (m, 4H), 6.94 (d, J=8.8 Hz, 1H), 5.83 (s, 1H), 3.94 (d, J=7.0 Hz, 2H), 5.59 (s, 2H), 3.38 (s, 3H), 3.20 (s, 3H), 1.47 (d, J=7.1 Hz, 3H), 1.13 (t, J=6.9 Hz, 3H). MS (ESI) 557.1 (M+H$^+$).

Example 72

N-(cyclopropylmethyl)-N-[4-(2,4-difluorophenoxy)-3-(4-ethoxy-1-methyl-6-oxo-1,6-dihydropyridin-3-yl)phenyl]ethanesulfonamide Example 72A N-[4-(2,4-difluorophenoxy)-3-(4-ethoxy-1-methyl-6-oxo-1,6-dihydropyridin-3-yl)phenyl]ethanesulfonamide A flask with stir bar was charged with Example 1G (1.028 g, 2.76 mmol), ethanesulfonyl chloride (0.55 mL, 5.80 mmol) and triethylamine (2.0 mL, 14.35 mmol) in dichloromethane (28 ml). The solution was stirred at ambient temperature for 18 hours. The mixture was stripped down by rotory evaporator, suspended in THF (18 mL), then treated with 1 M sodium hydroxide (9 mL, 9.00 mmol). The mixture was stirred at 60° C. for 20 hours. The mixture was cooled and shaken in a seperatory funnel with 100 mL each of ethyl acetate and brine. The organics were dried over magnesium sulfate. After filtration and solvent removal the crude product was chromatographed on a 40 g silica cartridge eluting with 0-10% methanol/dichloromethane to provide the title compound (1.13 g, 88%).

Example 72B

N-(cyclopropylmethyl)-N-[4-(2,4-difluorophenoxy)-3-(4-ethoxy-1-methyl-6-oxo-1,6-dihydropyridin-3-yl)phenyl]ethanesulfonamide To a solution of Example 72A (50 mg, 0.108 mmol) in DMF (1 mL) was added NaH (7.7 mg, 0.32 mmol) and the mixture was stirred at room temperature for 30 minutes. Then (bromomethyl)cyclopropane (43.6 mg, 0.323 mmol) was added and the mixture was stirred at 50° C. for 18 hours. Water (10 mL) was added and the mixture extracted with ethyl acetate (3×15 mL). The combined organics were washed with brine, dried (MgSO$_4$), filtered, and concentrated. The residue was purified by HPLC (C18, CH$_3$CN/water (0.1% NH$_4$HCO$_3$), 40-60%) to provide the title compound (5 mg, 8.96% yield). $^1$H NMR (400 MHz, CD$_3$OD) δ 7.46 (s, 1H), 7.28 (dd, J=6.9, 2.6 Hz, 2H), 6.92 (dd, J=12.2, 8.4 Hz, 2H), 6.80 (d, J=9.6 Hz, 2H), 5.81 (s, 1H), 3.87 (q, J=7.0 Hz, 2H), 3.43 (d, J=7.1 Hz, 2H), 3.38 (s, 3H), 3.00 (q, J=7.4 Hz, 2H), 1.22 (t, J=7.4 Hz, 3H), 1.14 (t, J=7.0 Hz, 3H), 0.81 (d, J=7.8 Hz, 1H), 0.33 (dd, J=8.0, 1.2 Hz, 2H), 0.01 (d, J=5.9 Hz, 2H). MS (ESI+) m/z 519.2 (M+H)$^+$.

Example 73

N-benzyl-N-[4-(2,4-difluorophenoxy)-3-(4-ethoxy-1-methyl-6-oxo-1,6-dihydropyridin-3-yl)phenyl]ethanesulfonamide Example 73 was prepared according to the procedure used for the preparation of Example 72B, substituting benzyl bromide for (bromomethyl)cyclopropane. $^1$H NMR (400 MHz, CD$_3$CN) δ 7.33-7.23 (m, 6H), 7.22-7.15 (m, 2H), 7.07-6.86 (m, 3H), 6.74 (d, J=8.7 Hz, 1H), 5.74 (s, 1H), 4.85 (s, 2H), 3.93 (q, J=7.0 Hz, 2H), 3.35 (s, 3H), 3.16 (q, J=7.4 Hz, 2H), 1.35 (t, J=7.4 Hz, 3H), 1.18 (t, J=7.0 Hz, 3H). MS (ESI+) m/z 555.2 (M+H)$^+$.

Example 74

N-(2-chlorobenzyl)-N-[4-(2,4-difluorophenoxy)-3-(4-ethoxy-1-methyl-6-oxo-1,6-dihydropyridin-3-yl)phenyl]ethanesulfonamide Example 74 was prepared according to the procedure used for the preparation of Example 72B, substituting 2-chlorobenzyl bromide for (bromomethyl)cyclopropane. $^1$H NMR (400 MHz, CD$_3$OD) δ 7.54-7.48 (m, 1H), 7.44 (s, 1H), 7.31 (dd, J=6.3, 4.1 Hz, 3H), 7.29-7.21 (m, 2H), 7.08-6.78 (m, 4H), 5.91 (s, 1H), 5.04 (s, 2H), 3.97 (q, J=7.0 Hz, 2H), 3.49 (s, 3H), 3.24 (q, J=7.4 Hz, 2H), 1.40 (t, J=7.4 Hz, 3H), 1.23 (t, J=7.0 Hz, 3H). MS (ESI+) m/z 589.2 (M+H)$^+$.

Example 75

N-[4-(2,4-difluorophenoxy)-3-(4-ethoxy-1-methyl-6-oxo-1,6-dihydropyridin-3-yl)phenyl]-N-(2-phenylethyl)ethanesulfonamide To a 10 mL microwave tube were added Example 72A (100 mg, 0.215 mmol), K$_2$CO$_3$ (29.8 mg, 0.215 mmol), (2-bromoethyl)benzene (120 mg, 0.646 mmol) and DMF (1 mL). The mixture was heated at 170° C. for 15 minutes under microwave irradiation. The solid was filtered and the residue was purified by HPLC (C18, CH$_3$CN/water (0.1% NH$_4$HCO$_3$), 40-70%) to give the title compound (102 mg, 0.179 mmol, 83% yield). $^1$H NMR (400 MHz, CD$_3$OD) δ 7.55 (s, 1H), 7.35-7.28 (m, 2H), 7.24 (d, J=7.4 Hz, 2H), 7.21-7.11 (m, 3H), 7.03 (d, J=5.5 Hz, 2H), 6.90 (d, J=8.5 Hz, 2H), 5.94 (s, 1H), 4.05-3.91 (m, 4H), 3.51 (s, 3H), 3.05 (d, J=7.4 Hz, 2H), 2.82 (t, J=7.4 Hz, 2H), 1.32-1.23 (m, 6H). MS (ESI+) m/z 569.2 (M+H)$^+$.

Example 76

N-(cyclopropylmethyl)-N-[4-(2,4-difluorophenoxy)-3-(4-ethoxy-1-methyl-6-oxo-1,6-dihydropyridin-3-yl)phenyl]-1-phenylmethanesulfonamide

Example 76A

N-(4-(2,4-difluorophenoxy)-3-(4-ethoxy-1-methyl-6-oxo-1,6-dihydropyridin-3-yl)phenyl)-1-phenylmethanesulfonamide Example 76A was prepared according to the procedure used for the preparation of Example 72A, substituting phenylmethanesulfonyl chloride for ethanesulfonyl chloride.

Example 76B

N-(cyclopropylmethyl)-N-[4-(2,4-difluorophenoxy)-3-(4-ethoxy-1-methyl-6-oxo-1,6-dihydropyridin-3-yl)phenyl]-1-phenylmethanesulfonamide Example 76B was prepared according to the procedure used for the preparation of Example 75, substituting Example 76A for Example 72A and (bromomethyl)cyclopropane for (2-bromoethyl)benzene, respectively. $^1$H NMR (400 MHz, CD$_3$OD) δ 7.46 (s, 1H), 7.37 (d, J=6.3 Hz, 2H), 7.32-7.16 (m, 4H), 7.03-6.82 (m, 5H), 5.87 (s, 1H), 4.37 (s, 2H), 3.93 (d, J=7.0 Hz, 2H), 3.45 (s, 3H), 3.35 (d, J=7.1 Hz, 2H), 1.19 (t, J=7.0 Hz, 3H), 0.82 (s, 1H), 0.35 (q, J=5.9 Hz, 2H), 0.01 (q, J=4.7 Hz, 2H). MS (ESI+) m/z 581.0 (M+H)$^+$.

Example 77

N-benzyl-N-[4-(2,4-difluorophenoxy)-3-(4-ethoxy-1-methyl-6-oxo-1,6-dihydropyridin-3-yl)phenyl]-1-phenylmethanesulfonamide Example 77 was prepared according to the procedure used for the preparation of Example 75, substituting Example 76A for Example 72A and benzyl bromide for (2-bromoethyl)benzene, respectively. $^1$H NMR (400 MHz, CD$_3$OD) δ 7.46 (d, J=6.3 Hz, 2H), 7.41-7.33 (m, 4H), 7.29-7.19 (m, 5H), 7.12 (dd, J=8.8, 2.7 Hz, 1H), 7.08-6.99 (m, 2H), 6.98-6.84 (m, 2H), 6.74 (d, J=8.7 Hz, 1H), 5.91 (s, 1H), 4.73 (s, 2H), 4.52 (s, 2H), 3.97 (q, J=7.0 Hz, 2H), 3.50 (s, 3H), 1.24 (t, J=7.0 Hz, 3H). MS (ESI+) m/z 617.2 (M+H)$^+$.

Example 78

N-(2-chlorobenzyl)-N-[4-(2,4-difluorophenoxy)-3-(4-ethoxy-1-methyl-6-oxo-1,6-dihydropyridin-3-yl)phenyl]-1-phenylmethanesulfonamide Example 78 was prepared according to the procedure used for the preparation of Example 75, substituting Example 76A for Example 72A and 2-chlorobenzyl bromide for (2-bromoethyl)benzene, respectively. $^1$H NMR (400 MHz, CD$_3$OD) δ 7.53-7.46 (m, 3H), 7.45-7.36 (m, 4H), 7.33 (dd, J=7.2, 2.0 Hz, 1H), 7.30-7.18 (m, 3H), 7.14 (d, J=2.6 Hz, 1H), 7.11-7.02 (m, 1H), 6.97-6.88 (m, 2H), 6.80 (d, J=8.8 Hz, 1H), 5.94 (s, 1H), 4.92 (s, 2H), 4.56 (s, 2H), 3.99 (q, J=7.0 Hz, 2H), 3.52 (s, 3H), 1.26 (t, J=7.0 Hz, 3H). MS (ESI+) m/z 651.2 (M+H)$^+$.

Example 79

N-[4-(2,4-difluorophenoxy)-3-(4-ethoxy-1-methyl-6-oxo-1,6-dihydropyridin-3-yl)phenyl]-1-phenyl-N-(2-phenylethyl)methanesulfonamide Example 79 was prepared according to the procedure used for the preparation of Example 75, substituting Example 76A for Example 72A. $^1$H NMR (400 MHz, CD$_3$OD) δ 7.51 (s, 1H), 7.41-7.28 (m, 5H), 7.26-7.18 (m, 4H), 7.13-6.98 (m, 5H), 6.93 (t, J=8.6 Hz, 1H), 6.85 (d, J=8.7 Hz, 1H), 5.95 (s, 1H), 4.37 (s, 2H), 4.01 (d, J=7.0 Hz, 2H), 3.88-3.77 (m, 2H), 3.52 (s, 3H), 2.80-2.68 (m, 2H), 1.27 (t, J=7.0 Hz, 3H). MS (ESI+) m/z 631.2 (M+H)$^+$.

Example 80

N-[2-(2-chlorophenyl)ethyl]-N-[4-(2,4-difluorophenoxy)-3-(4-ethoxy-1-methyl-6-oxo-1,6-dihydropyridin-3-yl)phenyl]ethanesulfonamide Example 80 was prepared according to the procedure used for the preparation of Example 75, substituting 2-(2-bromoethyl)chlorobenzene for (2-bromoethyl)benzene. $^1$H NMR (400 MHz, CD$_3$OD) δ 7.57 (s, 1H), 7.41-7.27 (m, 4H), 7.27-7.16 (m, 2H), 7.14-6.99 (m, 2H), 6.93 (t, J=6.6 Hz, 2H), 5.97 (s, 1H), 4.06-3.97 (m, 4H), 3.54 (s, 3H), 3.12 (q, J=7.4 Hz, 2H), 3.04-2.96 (m, 2H), 1.36-1.25 (m, 6H). MS (ESI+) m/z 603.1 (M+H)$^+$.

Example 81

N-[4-(2,4-difluorophenoxy)-3-(4-ethoxy-1-methyl-6-oxo-1,6-dihydropyridin-3-yl)phenyl]-2-(3-phenyl-1H-pyrazol-1-yl)acetamide A vial with stir bar was charged with 2-(3-phenyl-1H-pyrazol-1-yl)acetic acid (0.072 g, 0.356 mmol), Example 1G (0.109 g, 0.293 mmol), EDC (0.074 g, 0.386 mmol) and HOBT (0.050 g, 0.327 mmol) in dichloromethane (4 mL). N-methylmorpholine (0.1 mL, 0.910 mmol) was added, and the mixture was stirred at ambient temperature for 72 hours. The mixture was shaken in a seperatory funnel with 30 mL each of dichloromethane and aqueous sodium carbonate. The organics were dried over sodium sulfate, filtered and concentrated. The crude material was purified by HPLC (C18, CH$_3$CN/water (0.1% TFA), 0-100%) to provide the trifluoroacetate salt of the title compound. $^1$H NMR (400 MHz, DMSO-d$_6$) δ 10.42 (s, 1H), 7.80 (m, 3H), 7.63-7.55 (m, 2H), 7.52 (dd, J=8.9, 2.6 Hz, 1H), 7.45-7.34 (m, 3H), 7.29 (t, J=7.4 Hz, 1H), 7.01 (t, J=7.2 Hz, 2H), 6.90 (d, J=8.7 Hz, 1H), 6.75 (d, J=2.2 Hz, 1H), 5.79 (s, 1H), 5.06 (s, 2H), 3.89 (dd, J=15.2, 8.1 Hz, 2H), 3.34 (s, 3H), 1.13 (t, J=6.9 Hz, 3H). MS (ESI) m/z 557.1 (M+H$^+$).

Example 82

2-(5-chloro-2-fluorophenyl)-N-[4-(2,4-difluorophenoxy)-3-(4-ethoxy-1-methyl-6-oxo-1,6-dihydropyridin-3-yl)phenyl]acetamide Example 82 was prepared according to the procedure used for the preparation of Example 81, substituting 2-(5-chloro-2-fluorophenyl)acetic acid for 2-(3-phenyl-1H-pyrazol-1-yl)acetic acid. $^1$H NMR (400 MHz, DMSO-d$_6$) δ 10.29 (s, 1H), 7.61-7.56 (m, 2H), 7.54-7.46 (m, 2H), 7.43-7.32 (m, 2H), 7.25 (t, J=9.1 Hz, 1H), 7.07-6.95 (m, 2H), 6.88 (d, J=8.8 Hz, 1H), 5.79 (s, 1H), 3.91 (q, J=6.9 Hz, 2H), 3.34 (s, 3H), 1.13 (t, J=6.9 Hz, 3H). MS (ESI) m/z 543.1 (M+H$^+$).

Example 83

N-[4-(2,4-difluorophenoxy)-3-(4-ethoxy-1-methyl-6-oxo-1,6-dihydropyridin-3-yl)phenyl]-2-(2-methyl-1,3-thiazol-4-yl)acetamide The trifluoroacetate salt of Example 82 was prepared according to the procedure used for the preparation of Example 81, substituting 2-(2-methyl-1,3-thiazol-4-yl)acetic acid for 2-(3-phenyl-1H-pyrazol-1-yl)acetic acid. $^1$H NMR (400 MHz, DMSO-d$_6$) δ 10.23 (s, 1H), 7.60 (d, J=2.6 Hz, 2H), 7.53 (dd, J=8.8, 2.6 Hz, 1H), 7.36 (ddd, J=11.2, 8.7, 2.7 Hz, 1H), 7.27 (s, 1H), 7.06-6.95 (m, 2H), 6.88 (d, J=8.8 Hz, 1H), 5.79 (s, 1H), 3.91 (q, J=6.9 Hz, 2H), 3.74 (s, 2H), 3.34 (s, 3H), 2.63 (s, 3H), 1.13 (t, J=6.9 Hz, 3H). MS (ESI) m/z 512.1 (M+H$^+$).

Example 84

N-[4-(2,4-difluorophenoxy)-3-(4-ethoxy-1-methyl-6-oxo-1,6-dihydropyridin-3-yl)phenyl]-2-(1H-pyrazol-1-yl)acetamide A solution of Example 1G and DIPEA (0.15 M and 0.43 M in DMA, respectively, 257 µL, 0.04 mmol Example 1G (1.0 equivalent) and 0.12 mmol DIPEA (3.0 equivalents)), HATU (0.2 M in DMA, 257 µL, 0.052 mmol, 1.3 equivalents), and 2-(1H-pyrazol-1-yl)acetic acid (0.40 M in DMA, 121 µL, 0.048 mmol, 1.2 equivalents) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 µL min$^{-1}$ (10 minute residence time). Upon exiting the reactor, the reaction was loaded directly into an injection loop and purified by preparative HPLC on a Phenomenex Luna C8(2) 5 µm 100 Å AXIA column (50 mm×21.2 mm). A gradient of acetonitrile (A) and 0.1% ammonium acetate in water (B) was used, at a flow rate of 30 mL/min (0-0.5 min 5% A, 0.5-6.5 min linear gradient 5-60% A, 6.5-7.0 min linear gradient 60-100% A, 7.0-8.9 min 100% A, 8.9-9.0 min linear gradient 100-5% A, 9.0-10 min 5% A) to yield the title compound (7.33 mg, 39% yield). $^1$H NMR (400 MHz, DMSO-d$_6$/D$_2$O) δ 7.76 (d, J=2.3 Hz, 1H), 7.60-7.45 (m, 4H), 7.37-7.28 (m, 1H), 7.07-6.87 (m, 3H), 6.31 (t, J=2.1 Hz, 1H), 5.82 (s, 1H), 5.00 (s, 2H), 3.93 (q, J=6.9 Hz, 2H), 3.36 (s, 3H), 1.14 (t, J=6.9 Hz, 3H). MS (ESI) m/z 481.1 (M+H$^+$).

Example 85

N-[4-(2,4-difluorophenoxy)-3-(4-ethoxy-1-methyl-6-oxo-1,6-dihydropyridin-3-yl)phenyl]-2-(pyrimidin-5-yl)acetamide Example 85 was prepared according to the procedure used for the preparation of Example 84, substituting 2-(pyrimidin-5-yl)acetic acid for 2-(1H-pyrazol-1-yl)acetic acid. $^1$H NMR (400 MHz, DMSO-d$_6$/D$_2$O) δ 9.09 (s, 1H), 8.76 (s, 2H), 7.58-7.49 (m, 3H), 7.32 (ddd, J=11.2, 8.6, 2.7 Hz, 1H), 7.06-6.93 (m, 2H), 6.90 (d, J=8.7 Hz, 1H), 5.82 (s, 1H), 3.92 (q, J=6.9 Hz, 2H), 3.36 (s, 3H), 1.13 (t, J=6.9 Hz, 3H). MS (ESI) m/z 493.1 (M+H$^+$).

Example 86

N-[4-(2,4-difluorophenoxy)-3-(4-ethoxy-1-methyl-6-oxo-1,6-dihydropyridin-3-yl)phenyl]-2-(3,5-dimethyl-1H-pyrazol-1-yl)acetamide Example 86 was prepared according to the procedure used for the preparation of Example 84, substituting 2-(3,5-dimethyl-1H-pyrazol-1-yl)acetic acid for 2-(1H-pyrazol-1-yl)acetic acid. $^1$H NMR (400 MHz, DMSO-d$_6$/D$_2$O) δ 7.59-7.54 (m, 1H), 7.52 (dd, J=8.7, 2.7 Hz, 1H), 7.37-7.28 (m, 1H), 7.07-6.94 (m, 2H), 6.91 (d, J=8.7 Hz, 1H), 5.86 (s, 1H), 5.82 (s, 1H), 4.82 (s, 2H), 3.92 (q, J=6.9 Hz, 2H), 3.36 (s, 3H), 2.19 (s, 3H), 2.08 (s, 3H), 1.14 (t, J=6.9 Hz, 3H). MS (ESI) m/z 509.1 (M+H$^+$).

Example 87

N-[4-(2,4-difluorophenoxy)-3-(4-ethoxy-1-methyl-6-oxo-1,6-dihydropyridin-3-yl)phenyl]-2-(1H-1,2,4-triazol-1-yl)acetamide Example 87 was prepared according to the procedure used for the preparation of Example 84, substituting 2-(1H-1,2,4-triazol-1-yl)acetic acid for 2-(1H-pyrazol-1-yl)acetic acid. $^1$H NMR (400 MHz, DMSO-d$_6$/D$_2$O) δ 8.56 (s, 1H), 8.02 (s, 1H), 7.60-7.49 (m, 3H), 7.38-7.28 (m, 1H), 7.08-6.95 (m, 2H), 6.91 (d, J=8.6 Hz, 1H), 5.83 (s, 1H), 5.13 (s, 2H), 3.93 (q, J=6.9 Hz, 2H), 3.36 (s, 3H), 1.14 (t, J=6.9 Hz, 3H). MS (ESI) m/z 482.1 (M+H$^+$).

Example 88

N-[4-(2,4-difluorophenoxy)-3-(4-ethoxy-1-methyl-6-oxo-1,6-dihydropyridin-3-yl)phenyl]-2-(pyrazin-2-yl)acetamide Example 88 was prepared according to the procedure used for the preparation of Example 84, substituting 2-(pyrazin-2-yl)acetic acid for 2-(1H-pyrazol-1-yl)acetic acid. $^1$H NMR (400 MHz, DMSO-d$_6$/D$_2$O) δ 8.66 (m, 1H), 8.59 (m, 1H), 8.54 (d, J=2.5 Hz, 1H), 7.59-7.49 (m, 3H), 7.37-7.27 (m, 1H), 7.07-6.93 (m, 2H), 6.90 (d, J=8.7 Hz, 1H), 5.82 (s, 1H), 3.92 (q, J=6.9 Hz, 2H), 3.36 (s, 3H), 1.13 (t, J=6.9 Hz, 3H). MS (ESI) m/z 493.1 (M+H$^+$).

Example 89

N-[2-(2-chlorophenyl)ethyl]-N-[4-(2,4-difluorophenoxy)-3-(4-ethoxy-1-methyl-6-oxo-1,6-dihydropyridin-3-yl)phenyl]-1-phenylmethanesulfonamide Example 89 was prepared according to the procedure used for the preparation of Example 75, substituting Example 76A for Example 72A and 2-(2-bromoethyl)chlorobenzene for (2-bromoethyl)benzene, respectively. 1H NMR (400 MHz, CD$_3$OD) δ 7.52 (s, 1H), 7.43-7.41 (m, 2H), 7.37-7.30 (m, 4H), 7.25-7.18 (m, 4H), 7.12-7.00 (m, 3H), 6.97-6.91 (m, 1H), 6.86 (d, J=8.7 Hz, 1H), 5.96 (s, 1H), 4.43 (s, 2H), 4.02 (q, J=7.0 Hz, 2H), 3.92-3.81 (m, 2H), 3.54 (s, 3H), 2.99-2.88 (m, 2H), 1.28 (t, J=7.0 Hz, 3H). MS (ESI) m/z 665.2 (M+H$^+$).

Example 90

N-[4-(2,4-difluorophenoxy)-3-(4-ethoxy-1-methyl-6-oxo-1,6-dihydropyridin-3-yl)phenyl]-1-phenyl-N-(1,3-thiazol-2-ylmethyl)methanesulfonamide Example 90 was prepared according to the procedure used for the preparation of Example 75, substituting Example 76A for Example 72A and 2-(chloromethyl)-1,3-thiazole for (2-bromoethyl)benzene, respectively. $^1$H NMR (400 MHz, CD$_3$OD) δ 7.69 (d, J=3.3 Hz, 1H), 7.58 (d, J=3.3 Hz, 1H), 7.51 (s, 1H), 7.50-7.45 (m, 1H), 7.42-7.35 (m, 1H), 7.29 (dd, J=8.8, 2.7 Hz, 1H), 7.20 (d, J=2.7 Hz, 1H), 7.13-6.98 (m, 1H), 6.96-6.89 (m, 1H), 6.82 (d, J=8.8 Hz, 1H), 5.95 (s, 1H), 5.11 (s, 1H), 4.60 (s, 1H), 4.01 (q, J=7.0 Hz, 1H), 3.53 (s, 1H), 1.27 (t, J=7.0 Hz, 1H). MS (ESI+) m/z 624.1 (M+H)$^+$.

Example 91

N-[4-(2,4-difluorophenoxy)-3-(4-ethoxy-1-methyl-6-oxo-1,6-dihydropyridin-3-yl)phenyl]-N-(pyridin-3-ylmethyl)ethanesulfonamide Example 91 was prepared according to the procedure used for the preparation of Example 75, substituting 3-(bromomethyl)pyridine for (2-bromoethyl)benzene. $^1$H NMR (400 MHz, CD$_3$OD) δ 8.48-8.33 (m, 2H), 7.83 (d, J=7.9 Hz, 1H), 7.54 (s, 1H), 7.49 (s, 1H), 7.41-7.35 (m, 1H), 7.34-7.24 (m, 2H), 7.04 (s, 1H), 6.96 (d, J=5.5 Hz, 1H), 6.88 (d, J=1.3 Hz, 1H), 6.81 (d, J=8.7 Hz, 1H), 5.91 (s, 1H), 4.95 (s, 2H), 3.96 (q, J=7.0 Hz, 2H), 3.49 (s, 3H), 3.23 (d, J=7.4 Hz, 2H), 1.40 (t, J=7.4 Hz, 3H), 1.22 (t, J=7.0 Hz, 3H). MS (ESI+) m/z 556.2 (M+H)$^+$.

Example 92

N-[4-(2,4-difluorophenoxy)-3-(4-ethoxy-1-methyl-6-oxo-1,6-dihydropyridin-3-yl)phenyl]-1-phenyl-N-(pyridin-3-ylmethyl)methanesulfonamide Example 92 was prepared according to the procedure used for the preparation of Example 75, substituting Example 76A for Example 72A and 3-(bromomethyl)pyridine for (2-bromoethyl)benzene, respectively. $^1$H NMR (400 MHz, CD$_3$OD) δ 8.42 (dd, J=4.9, 1.5 Hz, 1H), 8.33 (d, J=1.6 Hz, 1H), 7.77 (d, J=7.9 Hz, 1H), 7.55-7.47 (m, 2H), 7.46 (s, 1H), 7.43-7.34 (m, 4H), 7.20-7.10 (m, 1H), 7.11-6.99 (m, 2H), 7.01-6.87 (m, 2H), 6.78 (d, J=8.7 Hz, 1H), 5.93 (d, J=5.9 Hz, 1H), 4.82 (s, 2H), 4.58 (s, 2H), 3.99 (q, J=7.0 Hz, 2H), 3.52 (s, 3H), 1.25 (t, J=7.0 Hz, 3H). MS (ESI+) m/z 618.2 (M+H)$^+$.

Example 93

N-[4-(2,4-difluorophenoxy)-3-(4-ethoxy-1-methyl-6-oxo-1,6-dihydropyridin-3-yl)phenyl]-N-(pyrimidin-5-ylmethyl)ethanesulfonamide Example 93 was prepared according to the procedure used for the preparation of Example 75, substituting 5-(bromomethyl)pyrimidine for (2-bromoethyl)benzene. $^1$H NMR (400 MHz, CD$_3$OD) δ 9.07 (s, 1H), 8.72 (s, 2H), 7.55 (s, 1H), 7.43-7.29 (m, 2H), 7.13-6.82 (m, 4H), 5.95 (s, 1H), 5.01 (s, 2H), 4.01 (q, J=7.0 Hz, 2H), 3.52 (s, 3H), 3.31-3.24 (m, 2H), 1.43 (t, J=7.4 Hz, 3H), 1.27 (t, J=7.0 Hz, 3H). MS (ESI+) m/z 557.2 (M+H)$^+$.

Example 94

N-[4-(2,4-difluorophenoxy)-3-(4-ethoxy-1-methyl-6-oxo-1,6-dihydropyridin-3-yl)phenyl]-1-phenyl-N-(pyrimidin-5-ylmethyl)methanesulfonamide Example 94 was prepared according to the procedure used for the preparation of Example 75, substituting Example 76A for Example 72A and 5-(bromomethyl)pyrimidine for (2-bromoethyl)benzene, respectively. $^1$H NMR (400 MHz, CD$_3$OD) δ 9.05 (s, 1H), 8.63 (s, 2H), 7.55-7.48 (m, 3H), 7.44-7.36 (m, 3H), 7.18 (dd, J=8.8, 2.7 Hz, 1H), 7.14-7.06 (m, 2H), 7.04-6.91 (m, 2H), 6.81 (d, J=8.7 Hz, 1H), 5.95 (s, 1H), 4.85 (s, 2H), 4.61 (s, 2H), 4.01 (q, J=7.0 Hz, 2H), 3.53 (s, 3H), 1.27 (t, J=7.0 Hz, 3H). MS (ESI+) m/z 619.1 (M+H)⁺.

Example 95

N-[4-(2,4-difluorophenoxy)-3-(4-ethoxy-1-methyl-6-oxo-1,6-dihydropyridin-3-yl)phenyl]-N-(pyrazin-2-ylmethyl)ethanesulfonamide Example 95 was prepared according to the procedure used for the preparation of Example 75, substituting 2-(chloromethyl)pyrazine for (2-bromoethyl)benzene. $^1$H NMR (400 MHz, CD$_3$OD) δ 8.69 (d, J=1.3 Hz, 1H), 8.59-8.55 (m, 1H), 8.51 (d, J=2.5 Hz, 1H), 7.54 (s, 1H), 7.44-7.36 (m, 2H), 7.12-6.97 (m, 2H), 6.94-6.88 (m, 1H), 6.85 (d, J=8.7 Hz, 1H), 5.95 (s, 1H), 5.12 (s, 2H), 4.00 (q, J=7.0 Hz, 2H), 3.52 (s, 3H), 3.31-3.26 (m, 2H), 1.42 (t, J=7.4 Hz, 3H), 1.26 (t, J=7.0 Hz, 3H). MS (ESI+) m/z 557.1 (M+H)⁺.

Example 96

N-[4-(2,4-difluorophenoxy)-3-(4-ethoxy-1-methyl-6-oxo-1,6-dihydropyridin-3-yl)phenyl]-1-phenyl-N-(pyrazin-2-ylmethyl)methanesulfonamide Example 96 was prepared according to the procedure used for the preparation of Example 75, substituting Example 76A for Example 72A and 2-(chloromethyl)pyrazine for (2-bromoethyl)benzene, respectively. $^1$H NMR (400 MHz, CD$_3$OD) δ 8.61 (d, J=1.3 Hz, 1H), 8.56-8.51 (m, 1H), 8.47 (d, J=2.6 Hz, 1H), 7.50-7.43 (m, 3H), 7.39-7.31 (m, 3H), 7.24 (dd, J=8.8, 2.7 Hz, 1H), 7.16 (d, J=2.7 Hz, 1H), 7.05 (s, 1H), 7.00-6.93 (m, 1H), 6.89 (d, J=1.3 Hz, 1H), 6.77 (d, J=8.8 Hz, 1H), 5.92 (s, 1H), 4.97 (s, 2H), 4.60 (s, 2H), 3.98 (q, J=7.0 Hz, 2H), 3.50 (s, 3H), 1.23 (t, J=7.0 Hz, 3H). MS (ESI+) m/z 619.2 (M+H)⁺.

Example 97

N-[4-(2,4-difluorophenoxy)-3-(4-ethoxy-1-methyl-6-oxo-1,6-dihydropyridin-3-yl)phenyl]-N-[(1-methyl-1H-pyrazol-4-yl)methyl]ethanesulfonamide Example 97 was prepared according to the procedure used for the preparation of Example 75, substituting 4-(chloromethyl)-1-methylpyrazole for (2-bromoethyl)benzene. $^1$H NMR (400 MHz, CD$_3$OD) δ 7.53 (s, 1H), 7.48 (s, 1H), 7.29-7.25 (m, 3H), 7.13-6.97 (m, 2H), 6.97-6.83 (m, 2H), 5.94 (s, 1H), 4.77 (s, 2H), 4.01 (q, J=7.0 Hz, 2H), 3.82 (s, 3H), 3.52 (s, 3H), 3.18 (q, J=7.4 Hz, 2H), 1.39 (t, J=7.4 Hz, 3H), 1.27 (t, J=7.0 Hz, 3H). MS (ESI+) m/z 559.2 (M+H)⁺.

Example 98

N-[4-(2,4-difluorophenoxy)-3-(4-ethoxy-1-methyl-6-oxo-1,6-dihydropyridin-3-yl)phenyl]-N-[(1-methyl-1H-pyrazol-4-yl)methyl]-1-phenylmethanesulfonamide Example 98 was prepared according to the procedure used for the preparation of Example 75, substituting Example 76A for Example 72A and 4-(chloromethyl)-1-methylpyrazole for (2-bromoethyl)benzene, respectively. $^1$H NMR (400 MHz, CD$_3$OD) δ 7.49-7.43 (m, 3H), 7.41-7.33 (m, 4H), 7.21 (s, 1H), 7.12-6.97 (m, 4H), 6.92 (dd, J=2.7, 1.4 Hz, 1H), 6.80 (d, J=8.7 Hz, 1H), 5.94 (s, 1H), 4.62 (s, 2H), 4.49 (s, 2H), 4.01 (q, J=7.0 Hz, 2H), 3.80 (s, 3H), 3.52 (s, 3H), 1.27 (t, J=7.0 Hz, 3H). MS (ESI+) m/z 621.2 (M+H)⁺.

Example 99

N-[4-(2,4-difluorophenoxy)-3-(4-ethoxy-1-methyl-6-oxo-1,6-dihydropyridin-3-yl)phenyl]-N-(1,3-thiazol-2-ylmethyl)ethanesulfonamide Example 99 was prepared according to the procedure used for the preparation of Example 75, substituting 2-(chloromethyl)thiazole for (2-bromoethyl)benzene. $^1$H NMR (400 MHz, CD$_3$OD) δ 7.70 (d, J=3.3 Hz, 1H), 7.59 (d, J=3.3 Hz, 1H), 7.56 (s, 1H), 7.47-7.39 (m, 2H), 7.14-6.98 (m, 2H), 6.97-6.84 (m, 2H), 5.95 (s, 1H), 5.26 (s, 2H), 4.01 (q, J=7.0 Hz, 2H), 3.53 (s, 3H), 3.28 (q, J=7.4 Hz, 2H), 1.41 (t, J=7.4 Hz, 3H), 1.27 (t, J=7.0 Hz, 3H). MS (ESI+) m/z 562.2 (M+H)⁺.

Example 100

N-[4-(2,4-difluorophenoxy)-3-(4-ethoxy-1-methyl-6-oxo-1,6-dihydropyridin-3-yl)phenyl]-N-[(1-methyl-1H-imidazol-4-yl)methyl]ethanesulfonamide Example 100 was prepared according to the procedure used for the preparation of Example 75, substituting 4-(chloromethyl)-1-methylimidazole for (2-bromoethyl)benzene. 1H NMR (400 MHz, CD$_3$OD) δ 7.53 (s, 1H), 7.48 (s, 1H), 7.34-7.25 (m, 2H), 6.99 (d, J=5.5 Hz, 2H), 6.95 (s, 1H), 6.89 (t, J=9.4 Hz, 1H), 6.81 (d, J=8.7 Hz, 1H), 5.92 (s, 1H), 4.76 (s, 2H), 3.99 (q, J=7.0 Hz, 2H), 3.64 (s, 3H), 3.50 (s, 3H), 3.16 (q, J=7.4 Hz, 2H), 1.35 (t, J=7.4 Hz, 3H), 1.25 (t, J=7.0 Hz, 3H). MS (ESI+) m/z 559.2 (M+H)⁺.

Example 101

N-[4-(2,4-difluorophenoxy)-3-(4-ethoxy-1-methyl-6-oxo-1,6-dihydropyridin-3-yl)phenyl]-N-[(1-methyl-1H-imidazol-4-yl)methyl]-1-phenylmethanesulfonamide Example 101 was prepared according to the procedure used for the preparation of Example 75, substituting Example 76A for Example 72A and 4-(chloromethyl)-1-methylimidazole for (2-bromoethyl)benzene, respectively. $^1$H NMR (400 MHz, CD$_3$OD) δ 7.50-7.46 (m, 2H), 7.44-7.39 (m, 2H), 7.37-7.30 (m, 3H), 7.17-7.13 (m, 1H), 7.10-6.95 (m, 3H), 6.93-6.86 (m, 2H), 6.75 (d, J=8.7 Hz, 1H), 5.92 (s, 1H), 4.67 (s, 2H), 4.47 (s, 2H), 3.99 (q, J=7.0 Hz, 2H), 3.64 (s, 3H), 3.51 (s, 3H), 1.25 (t, J=7.0 Hz, 3H). MS (ESI+) m/z 621.2 (M+H)⁺.

Example 102

N-[4-(2,4-difluorophenoxy)-3-(4-ethoxy-1-methyl-6-oxo-1,6-dihydropyridin-3-yl)phenyl]-N-[(2S)-1,4-dioxan-2-ylmethyl]ethanesulfonamide A stock solution of Example 72A (0.16 M in DMF, 200 μL, 0.03 mmol Example 72A (1.0 equivalent)), K$_2$CO$_3$ (13.4 mg, 0.096 mmol, 3.2 equivalents) and (2S)-4-(1,4-dioxan-2-yl)methyl 4-methylbenzenesulfonate (0.04 M in DMA, 89 μL, 0.036 mmol, 1.2 equivalents), were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 μL min$^{-1}$ (10 minute residence time). Upon exiting the reactor, the reaction was loaded directly into an injection loop and purified by preparative HPLC on a Phenomenex Luna C8(2) 5 μm 100 Å AXIA column (50 mm×21.2 mm). A gradient of acetonitrile (A) and 0.1% ammonium acetate in water (B) was used, at a flow rate of 30 mL/min (0-0.5 min 5% A, 0.5-6.5 min linear gradient 5-60% A, 6.5-7.0 min linear gradient 60-100% A, 7.0-8.9 min 100% A, 8.9-9.0 min linear gradient 100-5% A, 9.0-10 min 5% A) to yield the title compound (6.39 mg, 32% yield). $^1$H NMR (400 MHz, DMSO-d$_6$/D$_2$O) δ 7.56 (m, 1H), 7.44-7.38 (m, 2H), 7.29 (m, 1H), 7.15-7.03 (m, 2H), 6.96 (m, 1H), 5.87 (s, 1H), 4.02 (q, J=7.0 Hz, 2H), 3.80 (m, 1H), 3.77-3.72 (m, 2H), 3.70-3.62 (m, 2H), 3.61-3.49 (m, 4H), 3.44 (s, 3H), 3.20 (m, 2H), 1.31 (t, J=7.4 Hz, 3H), 1.24 (t, J=7.0 Hz, 3H). MS (ESI+) m/z 565.1 (M+H)$^+$.

Example 103

N-[4-(2,4-difluorophenoxy)-3-(4-ethoxy-1-methyl-6-oxo-1,6-dihydropyridin-3-yl)phenyl]-N-(tetrahydro-2H-pyran-4-ylmethyl)ethanesulfonamide Example 103 was prepared according to the procedure used for the preparation of Example 102, substituting 4-(bromomethyl)tetrahydro-2H-pyran for (2S)-4-(1,4-dioxan-2-yl)methyl 4-methylbenzenesulfonate. $^1$H NMR (400 MHz, DMSO-d$_6$/D$_2$O) δ 7.51 (s, 1H), 7.38-7.32 (m, 2H), 7.27-7.19 (m, 1H), 7.04 (m, 2H), 6.91 (d, J=9.2 Hz, 1H), 5.82 (s, 1H), 3.96 (q, J=7.0 Hz, 2H), 3.80 (d, J=11.7 Hz, 2H), 3.56 (d, J=6.6 Hz, 2H), 3.38 (s, 3H), 3.26-3.16 (m, 3H), 3.10 (q, J=7.3 Hz, 2H), 1.59 (m, 4H), 1.24 (t, J=9.0, 7.4 Hz, 3H), 1.18 (t, J=7.0 Hz, 3H). MS (ESI+) m/z 563.1 (M+H)$^+$.

Example 104

N-[4-(2,4-difluorophenoxy)-3-(4-ethoxy-1-methyl-6-oxo-1,6-dihydropyridin-3-yl)phenyl]-N-[2-(tetrahydro-2H-pyran-4-yl)ethyl]ethanesulfonamide Example 104 was prepared according to the procedure used for the preparation of Example 102, substituting 4-(2-bromoethyl)tetrahydro-2H-pyran for (2S)-4-(1,4-dioxan-2-yl)methyl 4-methylbenzenesulfonate. $^1$H NMR (400 MHz, DMSO-d$_6$/D$_2$O) δ 7.64 (m, 1H), 7.45-7.27 (m, 3H), 7.21-7.02 (m, 2H), 6.92-6.81 (m, 1H), 5.88 (s, 1H), 3.96 (q, J=7.0 Hz, 2H), 3.83-3.74 (m, 2H), 3.69-3.64 (m, 2H), 3.40 (s, 3H), 3.29-3.19 (m, 2H), 3.14 (q, J=7.4 Hz, 2H), 1.61-1.45 (m, 3H), 1.39-1.27 (m, 2H), 1.27-1.21 (t, J=7.4 Hz, 3H), 1.17 (t, J=7.0 Hz, 3H), 1.13-1.05 (m, 2H). MS (ESI+) m/z 577.1 (M+H)$^+$.

Biological Examples (1) Bromodomain Domain Binding Assay

A time-resolved fluorescence resonance energy transfer (TR-FRET) assay was used to determine the affinities of compounds of the Examples listed in Table 1 for each bromodomain of BRD4. His-tagged first (BD1: amino acids K57-E168) and second (BD2: amino acids E352-E168) bromodomains of BRD4 were expressed and purified. An Alexa647-labeled BET-inhibitor was used as the fluorescent probe in the assay.

Synthesis of Alexa647-labeled bromodomain inhibitor compound 2-((6S,Z)-4-(4-chlorophenyl)-2,3,9-trimethyl-6H-thieno[3,2-f][1,2,4]triazolo[4,3-a][1,4]diazepin-6-yl)acetic Acid Methyl 2-((6S,Z)-4-(4-chlorophenyl)-2,3,9-trimethyl-6H-thieno[3,2-f][1,2,4]triazolo[4,3-a][1,4]diazepin-6-yl)acetate (see e.g., WO 2006129623) (100.95 mg, 0.243 mmol) was suspended in 1 mL methanol to which was added a freshly prepared solution of lithium hydroxide monohydrate (0.973 mL, 0.5 M, 0.487 mmol) and shaken at ambient temperature for 3 hours. The methanol was evaporated and the pH adjusted with aqueous hydrochloric acid (1 M, 0.5 mL, 0.5 mmol) and extracted four times with ethyl acetate. The combined ethyl acetate layers were dried over magnesium sulfate and evaporated to afford 2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 87.0%); ESI-MS m/z=401.1 [(M+H)$^+$] which was used directly in the next reaction.

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis (2,2,2-trifluoroacetate)

2-((6S,Z)-4-(4-chlorophenyl)-2,3,9-trimethyl-6H-thieno[3,2-f][1,2,4]triazolo[4,3-a][1,4]diazepin-6-yl)acetic acid) (85.3 mg, 0.213 mmol) was combined with 2,2'-(ethane-1,2-diylbis(oxy))diethanamine (Sigma-Aldrich, 0.315 mg, 2.13 mmol) were combined in 5 mL anhydrous dimethylformamide. (1H-benzo[d][1,2,3]triazol-1-yloxy)tripyrrolidin-1-ylphosphonium hexafluorophosphate(V) (PyBOB, CSBio, Menlo Park Calif.; 332 mg, 0.638 mmol) was added and the reaction shaken at ambient temperature for 16 hours. The reaction was diluted to 6 mL with dimethylsulfoxide: water (9:1, v:v) and purified in two injections with time collection Waters Deltapak C18 200×25 mm column eluted with a gradient of 0.1% trifluoroacetic acid (v/v) in water and acetonitrile. The fractions containing the two purified products were lyophilized to afford N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (134.4 mg, 82.3%); ESI-MS m/z=531.1 [(M+H)$^+$]; 529.1 [(M−H)$^-$].

N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl) acetamide, 2,2,2-trifluoroacetate N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (5.4 mg, 0.0071 mmol) was combined with Alexa Fluor® 647 carboxylic acid, succinimidyl ester (Life Technologies, Grand Island, N.Y.; 3 mg, 0.0024 mmol) in 1 mL anhydrous dimethylsulfoxide containing diisopropylethylamine (1% v/v) and shaken at ambient temperature for 16 hours. The reaction was diluted to 3 mL with dimethylsulfoxide:water (9:1, v:v) and purified in one injection with time collection Waters Deltapak C18 200×25 mm column eluted with a gradient of 0.1% trifluoroacetic acid (v/v) in water and acetonitrile. The fractions containing the purified product were lyophilized to afford N-(2-(2-(2-amido-(Alexa647)-ethoxy)ethoxy)ethyl)-2-((4S,Z)-4-(4-chlorophenyl)-2,3,9-trimethyl-6H-thieno[3,2-f][1,2,4]triazolo[4,3-a]

[1,4]diazepin-6-yl)acetamide, 2,2,2-trifluoroacetate (1.8 mg); MALDI-MS m/z=1371.1, 1373.1 [(M+H)+] as a dark blue powder.

Assay:

Compound dilution series were prepared in DMSO via an approximately 3-fold serial dilution from one of the following:

Assay method A: 2.5 mM-797 nM
Assay method B: 0.47 mM to 7.8 nM
Assay method C: 0.047 mM to 0.78 nM or 5-fold serial dilution from Assay method A Compound dilutions were added directly into white, low-volume assay plates (Perkin Elmer Proxiplate 384 Plus #6008280) using a Labcyte Echo in conjunction with Labcyte Access and Thermo Multidrop CombinL robotics. Compounds were then suspended in eight microliters (μL) of assay buffer (20 mM Sodium Phosphate, pH 6.0, 50 mM NaCl, 1 mM Ethylenediaminetetraacetic acid disodium salt dihydrate, 0.01% Triton X-100, 1 mM DL-Dithiothreitol) containing His-tagged bromodomain, Europium-conjugated anti-His antibody (Invitrogen PV5596) and Alexa-647-conjugated probe.

The final concentration of 1× assay mixture for assay methods A, B and C contains 2% DMSO, 8 nM His-tagged bromodomain, 1 nM Europium-conjugated anti-His-tag antibody and 100 nM or 30 nM probe (for BDI or BDII, respectively) and compound concentration in the range of: 49.02 μM-15.63 nM for method A 9.19 μM-150 pM for method B, and 0.92 μM-15 pM for method C.

After a one-hour equilibration at room temperature, TR-FRET ratios were determined using an Envision multilabel plate reader (Ex 340, Em 495/520).

TR-FRET data were normalized to the means of 24 no-compound controls ("high") and 8 controls containing 1 μM un-labeled probe ("low"). Percent inhibition was plotted as a function of compound concentration and the data were fit with the 4 parameter logistic equation to obtain $IC_{50}$s. Inhibition constants ($K_i$) were calculated from the $IC_{50}$s, probe $K_d$ and probe concentration. Typical Z' values were between 0.65 and 0.75. The minimum significant ratio was determined to evaluate assay reproducibility (Eastwood et al., (2006) J Biomol Screen, 11: 253-261). The MSR was determined to be 2.03 for BDI and 1.93 for BDII, and a moving MSR (last six run MSR overtime) for both BDI and BDII was typically <3. The $K_i$ values are reported in Table 1.

(2) MX-1 Cell Line Proliferation Assay

The impact of compounds of the Examples on cancer cell proliferation was determined using the breast cancer cell line MX-1 (ATCC) in a 3-day proliferation assay. MX-1 cells were maintained in RPMI supplemented with 10% FBS at 37 C.° and an atmosphere of 5% $CO_2$. For compound testing, MX-1 cells were plated in 96-well black bottom plates at a density of 5000 cells/well in 90 μL, of culture media and incubated at 37° overnight to allow cell adhesion and spreading. Compound dilution series were prepared in DMSO via a 3-fold serial dilution from 3 mM to 0.1 μM. The DMSO dilution series were then diluted 1:100 in phosphate buffered saline, and 10 μL of the resulted solution were added to the appropriate wells of the MX-1 cell plate. The final compound concentrations in the wells were 3, 1, 0.3, 0.1, 0.03, 0.01, 0.003, 0.001, 0.0003, 0.0001, and 0.00003 μM. After the addition of compounds, the cells were incubated for 72 more hours and the amounts of viable cells were determined using the Cell Titer Glo assay kit (Promega) according to manufacturer suggested protocol.

Luminescence readings from the Cell Titer Glo assay were normalized to the DMSO treated cells and analyzed using the GraphPad Prism software with sigmoidal curve fitting to obtain $EC_{50}$s. The minimum significant ratio (MSR) was determined to evaluate assay reproducibility (Eastwood et al., (2006) J Biomol Screen, 11: 253-261). The overall MSR was determined to be 2.1 and a moving MSR (last six run MSR overtime) has been <2. The $EC_{50}$ values are reported in Table 1 for the indicated compounds.

TABLE 1

| Compounds of Example # | TR-FRET assay protocol | TR-FRET Binding Ki: BRD4 (BDI_K57-E168) (μM) | TR-FRET Binding Ki: BRD4 (BDII_E352-M457) (μM) | Cellular proliferation: $EC_{50}$ (μM) |
|---|---|---|---|---|
| 1 | B | 0.331 | 0.0246 | 0.114 |
| 2 | B | 0.271 | 0.0944 | 0.279 |
| 3 | B | 0.339 | 0.0777 | 0.433 |
| 4 | B | 0.244 | 0.0913 | 0.425 |
| 5 | C | 0.212 | 0.0655 | 0.681 |
| 6 | B | 0.28 | 0.128 | 0.356 |
| 7 | B | 0.288 | 0.0809 | 0.187 |
| 8 | B | >2.38 | 0.0977 | >3.0 |
| 9 | A | 0.991 | 0.0632 | 0.746 |
| 10 | B | 0.608 | 0.25 | 1.89 |
| 11 | A | 0.605 | 0.275 | 0.884 |
| 12 | B | 0.32 | 0.292 | 1.02 |
| 13 | B | 0.375 | 0.135 | 1.48 |
| 14 | B | 0.248 | 0.0616 | 0.111 |
| 15 | B | 0.255 | 0.683 | ND |
| 16 | B | 0.504 | 0.0282 | >3.0 |
| 17 | B | 0.725 | 2.4 | ND |
| 18 | B | >2.38 | >4.08 | ND |
| 19 | B | 0.575 | 0.189 | 0.557 |
| 20 | B | 0.716 | 0.573 | ND |
| 21 | B | 1.28 | 1.91 | ND |
| 22 | B | 1.03 | >4.08 | ND |
| 23 | A | 0.637 | 0.443 | >3.0 |
| 24 | A | 0.731 | 0.304 | 0.832 |
| 25 | A | 1.18 | 0.304 | 1.54 |
| 26 | B | 0.115 | 0.0714 | ND |
| 27 | B | 0.242 | 0.0365 | 0.73 |
| 28 | B | >2.38 | 0.0541 | 0.605 |
| 29 | B | 0.131 | 0.0507 | 0.433 |
| 30 | B | 0.188 | 0.0389 | >3.0 |
| 31 | B | 0.14 | 0.0579 | ND |
| 32 | B | 0.248 | 0.185 | ND |
| 33 | B | 0.0718 | 0.0369 | 0.464 |
| 34 | B | 0.156 | 0.108 | ND |
| 35 | B | 0.0843 | 0.00936 | 0.375 |
| 36 | B | 0.137 | 0.0662 | 0.476 |
| 37 | B | 1.69 | 0.0694 | 1.44 |
| 38 | C | 0.124 | 0.0748 | 0.779 |
| 39 | B | 0.329 | 0.0388 | 0.595 |
| 40 | B | 0.284 | 0.0542 | ND |
| 41 | B | 0.0685 | 0.0108 | 0.398 |
| 42 | B | 0.911 | 0.0756 | 0.678 |
| 43 | B | 0.224 | 0.11 | ND |
| 44 | B | 0.304 | 0.155 | ND |
| 45 | B | 2.32 | 0.112 | 0.981 |
| 46 | B | 0.0895 | 0.0477 | 0.449 |
| 47 | B | 0.226 | 0.0567 | ND |
| 48 | B | 0.111 | 0.0468 | ND |
| 49 | B | 0.116 | 0.0754 | ND |
| 50 | B | 0.991 | 0.355 | ND |
| 51 | B | >2.38 | 0.176 | ND |
| 52 | B | >2.38 | 0.722 | ND |
| 53 | B | 0.324 | 0.339 | ND |
| 54 | B | >2.38 | 1.81 | ND |
| 55 | B | >2.38 | 0.575 | ND |
| 56 | B | 0.247 | 0.0601 | ND |
| 57 | B | 0.15 | 0.18 | 0.712 |
| 58 | C | 0.302 | 0.127 | ND |
| 59 | B | 0.767 | 0.193 | ND |
| 60 | B | >2.38 | 0.904 | ND |
| 61 | B | 2.19 | 0.489 | ND |
| 62 | B | >2.38 | 0.24 | ND |

TABLE 1-continued

| Compounds of Example # | TR-FRET assay protocol | TR-FRET Binding Ki: BRD4 (BDI_K57-E168) (µM) | TR-FRET Binding Ki: BRD4 (BDII_E352-M457) (µM) | Cellular proliferation: EC$_{50}$ (µM) |
|---|---|---|---|---|
| 63 | B | 0.352 | 0.293 | ND |
| 64 | C | >0.238 | 0.0618 | 0.508 |
| 65 | C | 0.193 | 0.0967 | ND |
| 66 | C | 0.594 | 0.0384 | >1.0 |
| 67 | C | >0.238 | 0.128 | >1.0 |
| 68 | C | >0.238 | >0.408 | ND |
| 69 | C | >0.238 | >0.408 | ND |
| 70 | C | 0.224 | 0.0864 | >1.0 |
| 71 | C | 0.182 | 0.0813 | >1.0 |
| 72 | C | 0.0609 | 0.00228 | 0.233 |
| 73 | C | 0.0941 | 0.00966 | >1.0 |
| 74 | C | 0.191 | 0.0135 | 0.464 |
| 75 | C | 0.324 | 0.0478 | 0.614 |
| 76 | C | 1.04 | 0.0131 | >1.0 |
| 77 | C | >0.238 | 0.114 | >1.0 |
| 78 | C | >0.238 | 0.0713 | >1.0 |
| 79 | C | 0.915 | 0.288 | >1.0 |
| 80 | C | >0.238 | 0.0561 | >1.0 |
| 81 | C | >0.238 | 0.0219 | >1.0 |
| 82 | C | 0.136 | 0.063 | >1.0 |
| 83 | C | 0.139 | 0.0365 | 0.304 |
| 84 | C | >0.238 | 0.0675 | ND |
| 85 | C | 0.171 | 0.131 | ND |
| 86 | C | >0.238 | 0.0226 | ND |
| 87 | C | >0.238 | 0.171 | ND |
| 88 | C | 0.184 | 0.115 | ND |
| 89 | C | >0.238 | 0.202 | ND |
| 90 | C | >0.238 | 0.0444 | >1.0 |
| 91 | C | 0.116 | 0.0176 | 0.505 |
| 92 | C | 0.554 | 0.0924 | >1.0 |
| 93 | C | >0.238 | 0.0563 | >1.0 |
| 94 | C | >0.238 | 0.266 | ND |
| 95 | C | 0.194 | 0.0289 | >1.0 |
| 96 | C | >0.238 | 0.085 | >1.0 |
| 97 | C | 0.122 | 0.0173 | 0.55 |
| 98 | C | >0.238 | 0.0794 | >1.0 |
| 99 | C | 0.11 | 0.00458 | 0.555 |
| 100 | C | 0.358 | 0.0346 | >1.0 |
| 101 | C | >0.238 | 0.0928 | >1.0 |
| 102 | C | 0.139 | 0.0237 | 0.71 |
| 103 | C | 0.233 | 0.0117 | 0.677 |
| 104 | C | 0.185 | 0.0239 | ND |

ND = Not Determined

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

The invention claimed is:

1. A method for treating a cancer comprising prostate cancer or acute myelocytic leukemia in a subject comprising administering a therapeutically effective amount of a compound of formula (I) or a pharmaceutically acceptable salt thereof, to a subject in need thereof

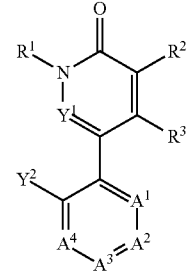

(I)

wherein
$R^1$ is $C_1$-$C_3$ alkyl or $C_1$-$C_3$ haloalkyl;
$R^2$ is H;
$R^3$ is —O—$C_1$-$C_6$ alkyl, —OCD$_2$CH$_3$, or —OCD$_2$CD$_3$;
$Y^1$ is N or $CR^4$, wherein $R^4$ is H, $C_1$-$C_3$ alkyl, or $C_1$-$C_3$ haloalkyl;
$A^2$ is $CR^5$, and $A^1$, $A^3$, and $A^4$ are $CR^6$; or
$A^2$ is $CR^5$, $A^1$ and $A^3$ are $CR^6$, and $A^4$ is N;
$R^5$ is —N($R^{5d}$)—$C_1$-$C_6$ alkylenyl-$R^{5a}$, —N($R^{5d}$)C(O)—$C_1$-$C_6$ alkylenyl-$R^{5b}$, —N($R^{5d}$)SO$_2$—$C_1$-$C_6$ alkylenyl-$R^{5c}$, —N($R^{5d}$)C(O)N($R^{5d}$)-$G^1$, —N($R^{5d}$)C(O)N($R^{5d}$)—$C_1$-$C_6$ alkylenyl-$R^{5a}$, —N($R^{5d}$)SO$_2$N($R^{5d}$)—$C_1$-$C_6$ alkylenyl-$R^{5a}$, —C(O)N($R^{5d}$)—$C_1$-$C_6$ alkylenyl-$R^{5a}$, or —SO$_2$N($R^{5d}$)—$C_1$-$C_6$ alkylenyl-$R^{5a}$, wherein
$R^5$, at each occurrence, is independently $G^1$, —OR$^{5aa}$, —OC(O)R$^{5dd}$, —SR$^{5aa}$, —S(O)R$^{5aa}$, —SO$_2$R$^{5aa}$, —SO$_2$NR$^{5bb}$R$^{5cc}$, —NR$^{5bb}$R$^{5cc}$, —NR$^{5bb}$C(O)R$^{5dd}$, —NR$^{5bb}$SO$_2$R$^{5dd}$, —NR$^{5bb}$C(O)OR$^{5dd}$, —NR$^{5bb}$C(O)NR$^{5bb}$R$^{5cc}$, —NR$^{5bb}$SO$_2$NR$^{5bb}$R$^{5cc}$, —C(O)R$^{5aa}$, —C(O)OR$^{5aa}$, or —C(O)NR$^{5bb}$R$^{5cc}$,
$R^{5b}$ is $G^1$, —OR$^{5aa}$, —OC(O)R$^{5dd}$, —SR$^{5aa}$, —S(O)R$^{5aa}$, —SO$_2$R$^{5aa}$, —SO$_2$NR$^{5bb}$R$^{5cc}$, —N(R$^{5bb}$)(G$^1$), —NR$^{5bb}$—(C$_1$-C$_6$ alkylenyl)-$G^1$, —NR$^{5bb}$C(O)R$^{5dd}$, —NR$^{5bb}$SO$_2$R$^{5dd}$, —NR$^{5bb}$C(O)OG$^1$, —NR$^{5bb}$C(O)O—(C$_1$-C$_6$ alkylenyl)-$G^1$, —NR$^{5bb}$C(O)NR$^{5bb}$R$^{5cc}$, —NR$^{5bb}$SO$_2$NR$^{5bb}$R$^{5cc}$, —C(O)R$^{5aa}$, —C(O)OR$^{5aa}$, or —C(O)NR$^{5bb}$R$^{5cc}$,
$R^{5c}$ is —OR$^{5aa}$, —OC(O)R$^{5dd}$, —SR$^{5aa}$, —S(O)R$^{5aa}$, —SO$_2$R$^{5aa}$, —SO$_2$NR$^{5bb}$R$^{5cc}$, —NR$^{5bb}$R$^{5cc}$, —NR$^{5bb}$C(O)R$^{5dd}$, —NR$^{5bb}$SO$_2$R$^{5dd}$, —NR$^{5bb}$C(O)OR$^{5dd}$, —NR$^{5bb}$C(O)NR$^{5bb}$R$^{5cc}$, —NR$^{5bb}$SO$_2$NR$^{5bb}$R$^{5cc}$, —C(O)R$^{5aa}$, —C(O)OG$^1$, —C(O)O—(C$_1$-C$_6$ alkylenyl)-$G^1$, or —C(O)NR$^{5bb}$R$^{5cc}$,
$R^{5d}$, at each occurrence, is independently H, $C_1$-$C_6$ alkyl, $C_2$-$C_6$ alkenyl, $C_2$-$C_6$ alkynyl, $C_1$-$C_6$ haloalkyl, $G^1$, —OR$^{5aa}$, —OC(O)R$^{5dd}$, —SR$^{5aa}$, —S(O)R$^{5aa}$, —SO$_2$R$^{5aa}$, —SO$_2$NR$^{5bb}$R$^{5cc}$, —NR$^{5bb}$R$^{5cc}$, —NR$^{5bb}$C(O)R$^{5dd}$, —NR$^{5bb}$SO$_2$R$^{5dd}$, —NR$^{5bb}$C(O)OR$^{5dd}$, —NR$^{5bb}$C(O)NR$^{5bb}$R$^{5cc}$, —NR$^{5bb}$SO$_2$NR$^{5bb}$R$^{5cc}$, —C(O)R$^{5aa}$, —C(O)OR$^{5aa}$, —C(O)NR$^{5bb}$R$^{5cc}$, —(C$_1$-C$_6$ alkylenyl)-$G^1$, —(C$_1$-C$_6$ alkylenyl)-OR$^{5aa}$, —(C$_1$-C$_6$ alkylenyl)-OC(O)R$^{5dd}$, —(C$_1$-C$_6$ alkylenyl)-SR$^{5aa}$, —(C$_1$-C$_6$ alkylenyl)-S(O)R$^{5aa}$, —(C$_1$-C$_6$ alkylenyl)-SO$_2$R$^{5aa}$, —(C$_1$-C$_6$ alkylenyl)-SO$_2$NR$^{5bb}$R$^{5cc}$, —(C$_1$-C$_6$ alkylenyl)-NR$^{5bb}$R$^{5cc}$, —(C$_1$-C$_6$ alkylenyl)-NR$^{5bb}$C(O)R$^{5dd}$, —(C$_1$-C$_6$ alkylenyl)-NR$^{5bb}$SO$_2$R$^{5dd}$, —(C$_1$-C$_6$ alkylenyl)-NR$^{5bb}$C(O)OR$^{5dd}$, —(C$_1$-C$_6$ alkylenyl)-NR$^{5bb}$C(O)NR$^{5bb}$R$^{5cc}$, —(C$_1$-C$_6$ alkylenyl)-NR$^{5bb}$SO$_2$NR$^{5bb}$R$^{5cc}$, —(C$_1$-C$_6$ alkylenyl)-C(O)

$R^{5aa}$, —($C_1$-$C_6$ alkylenyl)-C(O)O$R^{5aa}$, or —($C_1$-$C_6$ alkylenyl)-C(O)N$R^{5bb}R^{5cc}$;

$R^6$ is H, $C_1$-$C_6$ alkyl, halogen, $C_1$-$C_6$ haloalkyl, or —CN;

$R^{5aa}$, $R^{5bb}$, and $R^{5cc}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^1$, or —($C_1$-$C_6$ alkylenyl)-$G^1$;

$R^{5dd}$, at each occurrence, is independently $C_1$-$C_6$ alkyl, $C_2$-$C_6$ alkenyl, $C_2$-$C_6$ alkynyl, $C_1$-$C_6$ haloalkyl, $G^1$, or —($C_1$-$C_6$ alkylenyl)-$G^1$;

$G^1$, at each occurrence, is independently aryl, heteroaryl, heterocycle, cycloalkyl, or cycloalkenyl, each of which is optionally substituted with 1, 2, 3, 4, or 5 $R^{1g}$ groups, $Y^2$ is -L-$G^2$; wherein
L is O or N($R^x$) wherein $R^x$ is H or $C_1$-$C_6$ alkyl;
$G^2$ is aryl, heteroaryl, heterocycle, cycloalkyl, or cycloalkenyl, each of which is optionally substituted with 1, 2, 3, 4, or 5 $R^{2g}$ groups;

$R^{1g}$ and $R^{2g}$, at each occurrence, are each independently oxo, $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{z1}$, —OC(O)$R^{z2}$, —OC(O)N$R^{z3}R^{z4}$, —$SR^{z1}$, —S(O)$_2R^{z1}$, —S(O)$_2$N$R^{z3}R^{z4}$, —C(O)$R^{z1}$, —C(O)O$R^{z1}$, —C(O)N$R^{z3}R^{z4}$, —N$R^{z3}R^{z4}$, —N($R^{z3}$)C(O)$R^{z2}$, —N($R^{z3}$)S(O)$_2R^{z2}$, —N($R^{z3}$)C(O)O($R^{z2}$), —N($R^{z3}$)C(O)N$R^{z3}R^{z4}$, —N($R^{z3}$)S(O)$_2$N$R^{z3}R^{z4}$, $G^3$, —($C_1$-$C_6$ alkylenyl)-CN, —($C_1$-$C_6$ alkylenyl)-O$R^{z1}$, —($C_1$-$C_6$ alkylenyl)-OC(O)$R^{z2}$, —($C_1$-$C_6$ alkylenyl)-OC(O)N$R^{z3}R^{z4}$, —($C_1$-$C_6$ alkylenyl)-S(O)$R^{z1}$, —($C_1$-$C_6$ alkylenyl)-S(O)$_2$N$R^{z3}R^{z4}$, —($C_1$-$C_6$ alkylenyl)-C(O)$R^{z1}$, —($C_1$-$C_6$ alkylenyl)-C(O)O$R^{z1}$, —($C_1$-$C_6$ alkylenyl)-C(O)N$R^{z3}R^{z4}$, —($C_1$-$C_6$ alkylenyl)-N$R^{z3}R^{z4}$, —($C_1$-$C_6$ alkylenyl)-N($R^{z3}$)C(O)$R^{z2}$, —($C_1$-$C_6$ alkylenyl)-N($R^{z3}$)S(O)$_2R^{z2}$, —($C_1$-$C_6$ alkylenyl)-N($R^{z3}$)C(O)O($R^{z2}$), —($C_1$-$C_6$ alkylenyl)-N($R^{z3}$)C(O)N$R^{z3}R^{z4}$, —($C_1$-$C_6$ alkylenyl)-N($R^{z3}$)S(O)$_2$N$R^{z3}R^{z4}$, —($C_1$-$C_6$ alkylenyl)-CN, or —($C_1$-$C_6$ alkylenyl)-$G^3$;

$R^{z1}$, $R^{z3}$, and $R^{z4}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^3$, or —$C_1$-$C_6$ alkylenyl-$G^3$;

$R^{z2}$, at each occurrence, is independently $C_1$-$C_6$ alkyl, $C_2$-$C_6$ alkenyl, $C_2$-$C_6$ alkynyl, $C_1$-$C_6$ haloalkyl, $G^3$, or —$C_1$-$C_6$ alkylenyl-$G^3$;

$G^3$ is aryl, heteroaryl, heterocycle, cycloalkyl, or cycloalkenyl, each of which is optionally substituted with 1, 2, 3, 4, or 5 $R^{3g}$ groups, $R^{3g}$, at each occurrence, is independently oxo, $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^a$, —OC(O)$R^b$, —OC(O)N$R^cR^d$, —$SR^a$, —S(O)$_2R^a$, —S(O)$_2$N$R^cR^d$, —C(O)$R^a$, —C(O)O$R^a$, —C(O)N$R^cR^d$, —N$R^cR^d$, —N($R^c$)C(O)$R^b$, —N($R^c$)S(O)$_2R^b$, —N($R^c$)C(O)O($R^b$), —N($R^c$)C(O)N$R^cR^d$, —N($R^c$)S(O)$_2$N$R^cR^d$, —($C_1$-$C_6$ alkylenyl)-CN, —($C_1$-$C_6$ alkylenyl)-O$R^a$, —($C_1$-$C_6$ alkylenyl)-OC(O)$R^b$, —($C_1$-$C_6$ alkylenyl)-OC(O)N$R^cR^d$, —($C_1$-$C_6$ alkylenyl)-S(O)$_2R^a$, —($C_1$-$C_6$ alkylenyl)-S(O)$_2$N$R^cR^d$, —($C_1$-$C_6$ alkylenyl)-C(O)$R^a$, —($C_1$-$C_6$ alkylenyl)-C(O)O$R^a$, —($C_1$-$C_6$ alkylenyl)-C(O)N$R^cR^d$, —($C_1$-$C_6$ alkylenyl)-N$R^cR^d$, —($C_1$-$C_6$ alkylenyl)-N($R^c$)C(O)$R^b$, —($C_1$-$C_6$ alkylenyl)-N($R^c$)S(O)$_2R^b$, —($C_1$-$C_6$ alkylenyl)-N($R^c$)C(O)O($R^b$), —($C_1$-$C_6$ alkylenyl)-N($R^c$)C(O)N$R^cR^d$, —($C_1$-$C_6$ alkylenyl)-N($R^c$)S(O)$_2$N$R^cR^d$, or —($C_1$-$C_6$ alkylenyl)-CN;

$R^a$, $R^c$, and $R^d$, at each occurrence, are each independently H, $C_1$-$C_6$ alkyl, $C_2$-$C_6$ alkenyl, $C_2$-$C_6$ alkynyl, or $C_1$-$C_6$ haloalkyl, and $R^b$, at each occurrence, is independently $C_1$-$C_6$ alkyl, $C_2$-$C_6$ alkenyl, $C_2$-$C_6$ alkynyl, or $C_1$-$C_6$ haloalkyl.

2. The method of claim 1, wherein $R^1$ is methyl.

3. The method of claim 1, wherein $R^3$ is —O—$C_1$-$C_6$ alkyl.

4. The method of claim 1, wherein $Y^1$ is $CR^4$.

5. The method of claim 1, wherein $Y^1$ is $CR^4$ and $R^3$ is —O—$C_1$-$C_3$ alkyl.

6. The method of claim 1, wherein the compound of formula (I) or the pharmaceutically acceptable salt thereof is selected from the group consisting of:

2-(2-chloro-5-fluorophenyl)-N-[4-(2,4-difluorophenoxy)-3-(4-ethoxy-1-methyl-6-oxo-1,6-dihydropyridin-3-yl)phenyl]acetamide;

N-[4-(2,4-difluorophenoxy)-3-(4-ethoxy-1-methyl-6-oxo-1,6-dihydropyridin-3-yl)phenyl]-2-(3,4-dihydro-2H-chromen-6-yl)acetamide;

2-(4-chloro-2-fluorophenyl)-N-[4-(2,4-difluorophenoxy)-3-(4-ethoxy-1-methyl-6-oxo-1,6-dihydropyridin-3-yl)phenyl]acetamide;

N-[4-(2,4-difluorophenoxy)-3-(4-ethoxy-1-methyl-6-oxo-1,6-dihydropyridin-3-yl)phenyl]-2-(1-methyl-1H-pyrazol-4-yl)acetamide;

N-[4-(2,4-difluorophenoxy)-3-(4-ethoxy-1-methyl-6-oxo-1,6-dihydropyridin-3-yl)phenyl]-2-(6-methylpyridin-3-yl)acetamide;

N-[4-(2,4-difluorophenoxy)-3-(4-ethoxy-1-methyl-6-oxo-1,6-dihydropyridin-3-yl)phenyl]-2-(1,5-dimethyl-1H-pyrazol-3-yl)acetamide;

N-[4-(2,4-difluorophenoxy)-3-(4-ethoxy-1-methyl-6-oxo-1,6-dihydropyridin-3-yl)phenyl]-2-(2-methyl-1,3-thiazol-5-yl)acetamide;

N-[4-(2,4-difluorophenoxy)-3-(4-ethoxy-1-methyl-6-oxo-1,6-dihydropyridin-3-yl)phenyl]-2-[3-(2-fluorophenyl)-1H-pyrazol-1-yl]acetamide;

5-[2-(2,4-difluorophenoxy)-5-{[3-(1H-pyrazol-1-yl)propyl]amino}phenyl]-4-ethoxy-1-methylpyridin-2(1H)-one;

5-{2-(2,4-difluorophenoxy)-5-[(6,7-dihydro-5H-pyrrolo[1,2-a]imidazol-2-ylmethyl)amino]phenyl}-4-ethoxy-1-methylpyridin-2(1H)-one;

5-[2-(2,4-difluorophenoxy)-5-{[(6-methylpyridin-2-yl)methyl]amino}phenyl]-4-ethoxy-1-methylpyridin-2(1H)-one;

5-[2-(2,4-difluorophenoxy)-5-{[(3-methylpyridin-2-yl)methyl]amino}phenyl]-4-ethoxy-1-methylpyridin-2(1H)-one;

5-[2-(2,4-difluorophenoxy)-5-{[(1-methyl-1H-pyrazol-5-yl)methyl]amino}phenyl]-4-ethoxy-1-methylpyridin-2(1H)-one;

methyl 4-{[4-(2,4-difluorophenoxy)-3-(4-ethoxy-1-methyl-6-oxo-1,6-dihydropyridin-3-yl)phenyl]amino}butanoate;

1-[4-(2,4-difluorophenoxy)-3-(4-ethoxy-1-methyl-6-oxo-1,6-dihydropyridin-3-yl)phenyl]-3-(3-phenoxyphenyl)urea;

1-[4-(2,4-difluorophenoxy)-3-(4-ethoxy-1-methyl-6-oxo-1,6-dihydropyridin-3-yl)phenyl]-3-(2,4-dimethylphenyl)urea;

1-[4-(2,4-difluorophenoxy)-3-(4-ethoxy-1-methyl-6-oxo-1,6-dihydropyridin-3-yl)phenyl]-3-(3,5-dimethylphenyl)urea;

1-[4-(2,4-difluorophenoxy)-3-(4-ethoxy-1-methyl-6-oxo-1,6-dihydropyridin-3-yl)phenyl]-3-[4-(trifluoromethoxy)phenyl]urea;

1-[4-(2,4-difluorophenoxy)-3-(4-ethoxy-1-methyl-6-oxo-1,6-dihydropyridin-3-yl)phenyl]-3-(2,5-dimethylphenyl)urea;

1-[4-(2,4-difluorophenoxy)-3-(4-ethoxy-1-methyl-6-oxo-1,6-dihydropyridin-3-yl)phenyl]-3-(4-fluorophenyl)urea;

1-(3-chlorophenyl)-3-[4-(2,4-difluorophenoxy)-3-(4-ethoxy-1-methyl-6-oxo-1,6-dihydropyridin-3-yl)phenyl]urea;

1-[4-(2,4-difluorophenoxy)-3-(4-ethoxy-1-methyl-6-oxo-1,6-dihydropyridin-3-yl)phenyl]-3-(3-methoxyphenyl)urea;

5-{2-(2,4-difluorophenoxy)-5-[(1,3-oxazol-5-ylmethyl)amino]phenyl}-4-ethoxy-1-methylpyridin-2(1H)-one;

5-[2-(2,4-difluorophenoxy)-5-{[(1-methyl-1H-imidazol-5-yl)methyl]amino}phenyl]-4-ethoxy-1-methylpyridin-2(1H)-one;

5-[2-(2,4-difluorophenoxy)-5-{[(1-ethyl-1H-pyrazol-3-yl)methyl]amino}phenyl]-4-ethoxy-1-methylpyridin-2(1H)-one;

N-[4-(2,4-difluorophenoxy)-3-(4-ethoxy-1-methyl-6-oxo-1,6-dihydropyridin-3-yl)phenyl]-5-oxo-5-phenylpentanamide;

N-[4-(2,4-difluorophenoxy)-3-(4-ethoxy-1-methyl-6-oxo-1,6-dihydropyridin-3-yl)phenyl]-3-(phenylsulfonyl)propanamide;

N-[4-(2,4-difluorophenoxy)-3-(4-ethoxy-1-methyl-6-oxo-1,6-dihydropyridin-3-yl)phenyl]-2-(3-phenoxyphenyl)acetamide;

N-[4-(2,4-difluorophenoxy)-3-(4-ethoxy-1-methyl-6-oxo-1,6-dihydropyridin-3-yl)phenyl]-2-[4-(methyl sulfonyl)phenyl]acetamide;

N-[4-(2,4-difluorophenoxy)-3-(4-ethoxy-1-methyl-6-oxo-1,6-dihydropyridin-3-yl)phenyl]-3-phenoxypropanamide;

N-[4-(2,4-difluorophenoxy)-3-(4-ethoxy-1-methyl-6-oxo-1,6-dihydropyridin-3-yl)phenyl]-2-(naphthalen-1-yl)acetamide;

N-[4-(2,4-difluorophenoxy)-3-(4-ethoxy-1-methyl-6-oxo-1,6-dihydropyridin-3-yl)phenyl]-2-{[(4-methylphenyl)sulfonyl]amino}acetamide;

N-[4-(2,4-difluorophenoxy)-3-(4-ethoxy-1-methyl-6-oxo-1,6-dihydropyridin-3-yl)phenyl]-2-(4-methylphenoxy)acetamide;

N-[4-(2,4-difluorophenoxy)-3-(4-ethoxy-1-methyl-6-oxo-1,6-dihydropyridin-3-yl)phenyl]-3-(2,3,4-trimethoxyphenyl)propanamide;

2-(benzyloxy)-N-[4-(2,4-difluorophenoxy)-3-(4-ethoxy-1-methyl-6-oxo-1,6-dihydropyridin-3-yl)phenyl]acetamide;

2-(1,2-benzoxazol-3-yl)-N-[4-(2,4-difluorophenoxy)-3-(4-ethoxy-1-methyl-6-oxo-1,6-dihydropyridin-3-yl)phenyl]acetamide;

N-[4-(2,4-difluorophenoxy)-3-(4-ethoxy-1-methyl-6-oxo-1,6-dihydropyridin-3-yl)phenyl]-2-(4-phenoxyphenyl)acetamide;

N-[4-(2,4-difluorophenoxy)-3-(4-ethoxy-1-methyl-6-oxo-1,6-dihydropyridin-3-yl)phenyl]-4-phenylbutanamide;

N-[4-(2,4-difluorophenoxy)-3-(4-ethoxy-1-methyl-6-oxo-1,6-dihydropyridin-3-yl)phenyl]-2-(naphthalen-2-yl)acetamide;

N-[4-(2,4-difluorophenoxy)-3-(4-ethoxy-1-methyl-6-oxo-1,6-dihydropyridin-3-yl)phenyl]-N'-phenylpentanediamide;

N-[4-(2,4-difluorophenoxy)-3-(4-ethoxy-1-methyl-6-oxo-1,6-dihydropyridin-3-yl)phenyl]-3-phenylpropanamide;

2-(biphenyl-4-yl)-N-[4-(2,4-difluorophenoxy)-3-(4-ethoxy-1-methyl-6-oxo-1,6-dihydropyridin-3-yl)phenyl]acetamide;

N-[4-(2,4-difluorophenoxy)-3-(4-ethoxy-1-methyl-6-oxo-1,6-dihydropyridin-3-yl)phenyl]-4-oxo-4-phenylbutanamide;

N-[4-(2,4-difluorophenoxy)-3-(4-ethoxy-1-methyl-6-oxo-1,6-dihydropyridin-3-yl)phenyl]-4-phenoxybutanamide;

2-[4-(benzyloxy)phenyl]-N-4-[2,4-difluorophenoxy)-3-(4-ethoxy-1-methyl-6-oxo-1,6-dihydropyridin-3-yl)phenyl]acetamide;

N-[4-(2,4-difluorophenoxy)-3-(4-ethoxy-1-methyl-6-oxo-1,6-dihydropyridin-3-yl)phenyl]-2-(2-methoxyphenyl)acetamide;

N-(2-{[4-(2,4-difluorophenoxy)-3-(4-ethoxy-1-methyl-6-oxo-1,6-dihydropyridin-3-yl)phenyl]amino}-2-oxoethyl)benzamide;

2-cyclohexyl-N-[4-(2,4-difluorophenoxy)-3-(4-ethoxy-1-methyl-6-oxo-1,6-dihydropyridin-3-yl)phenyl]acetamide;

2-[(1S,4R)-bicyclo[2.2.1]hept-2-yl]-N-[4-(2,4-difluorophenoxy)-3-(4-ethoxy-1-methyl-6-oxo-1,6-dihydropyridin-3-yl)phenyl]acetamide;

5-[5-{[2-(benzyloxy)-3-methoxybenzyl]amino}-2-(2,4-difluorophenoxy)phenyl]-4-ethoxy-1-methylpyridin-2(1H)-one;

5-[5-{[4-(benzyloxy)benzyl]amino}-2-(2,4-difluorophenoxy)phenyl]-4-ethoxy-1-methylpyridin-2(1H)-one;

5-{5-[(4-tert-butylbenzyl)amino]-2-(2,4-difluorophenoxy)phenyl}-4-ethoxy-1-methylpyridin-2(1H)-one;

5-{5-[(2,6-difluorobenzyl)amino]-2-(2,4-difluorophenoxy)phenyl}-4-ethoxy-1-methylpyridin-2(1H)-one;

5-[2-(2,4-difluorophenoxy)-5-{[3-(4-methoxyphenoxy)benzyl]amino}phenyl]-4-ethoxy-1-methylpyridin-2(1H)-one;

5-[5-({[5-(2-chlorophenyl)furan-2-yl]methyl}amino)-2-(2,4-difluorophenoxy)phenyl]-4-ethoxy-1-methylpyridin-2(1H)-one;

4-({[4-(2,4-difluorophenoxy)-3-(4-ethoxy-1-methyl-6-oxo-1,6-dihydropyridin-3-yl)phenyl]amino}methyl)benzonitrile;

2-({[4-(2,4-difluorophenoxy)-3-(4-ethoxy-1-methyl-6-oxo-1,6-dihydropyridin-3-yl)phenyl]amino}methyl)benzonitrile;

5-{2-(2,4-difluorophenoxy)-5-[(quinolin-4-ylmethyl)amino]phenyl}-4-ethoxy-1-methylpyridin-2(1H)-one;

5-[5-{[(5-chloro-3-methyl-1-phenyl-1H-pyrazol-4-yl)methyl]amino}-2-(2,4-difluorophenoxy)phenyl]-4-ethoxy-1-methylpyridin-2(1H)-one;

5-{2-(2,4-difluorophenoxy)-5-[({5-[2-(trifluoromethyl)phenyl]furan-2-yl}methyl)amino]phenyl}-4-ethoxy-1-methylpyridin-2(1H)-one;

5-{5-[(4-butoxybenzyl)amino]-2-(2,4-difluorophenoxy)phenyl}-4-ethoxy-1-methylpyridin-2(1H)-one;

5-{2-(2,4-difluorophenoxy)-5-[(4-phenoxybenzyl)amino]phenyl}-4-ethoxy-1-methylpyridin-2(1H)-one;

3-({[4-(2,4-difluorophenoxy)-3-(4-ethoxy-1-methyl-6-oxo-1,6-dihydropyridin-3-yl)phenyl]amino}methyl)benzonitrile;

5-{2-(2,4-difluorophenoxy)-5-[(4-fluorobenzyl)amino]phenyl}-4-ethoxy-1-methylpyridin-2(1H)-one;

5-{5-[(cyclopropylmethyl)amino]-2-(2,4-difluorophenoxy)phenyl}-4-ethoxy-1-methylpyridin-2(1H)-one;

1-(2-chloro-5-fluorophenyl)-N-(cyclopropylmethyl)-N-[4-(2,4-difluorophenoxy)-3-(4-ethoxy-1-methyl-6-oxo-1,6-dihydropyridin-3-yl)phenyl]methanesulfonamide;
2-(2-chloro-5-fluorophenyl)-N-(cyclopropylmethyl)-N-[4-(2,4-difluorophenoxy)-3-(4-ethoxy-1-methyl-6-oxo-1,6-dihydropyridin-3-yl)phenyl]acetamide;
N-[4-(benzyloxy)benzyl]-2-(2-chloro-5-fluorophenyl)-N-[4-(2,4-difluorophenoxy)-3-(4-ethoxy-1-methyl-6-oxo-1,6-dihydropyridin-3-yl)phenyl]acetamide;
2-(2-chloro-5-fluorophenyl)-N-[4-(2,4-difluorophenoxy)-3-(4-ethoxy-1-methyl-6-oxo-1,6-dihydropyridin-3-yl)phenyl]-N-(4-fluorobenzyl)acetamide;
2-(2-chloro-5-fluorophenyl)-N-[4-(2,4-difluorophenoxy)-3-(4-ethoxy-1-methyl-6-oxo-1,6-dihydropyridin-3-yl)phenyl]propanamide;
2-(2-chloro-5-fluorophenyl)-N-[4-(2,4-difluorophenoxy)-3-(4-ethoxy-1-methyl-6-oxo-1,6-dihydropyridin-3-yl)phenyl]-N-methylacetamide;
N-(cyclopropylmethyl)-N-[4-(2,4-difluorophenoxy)-3-(4-ethoxy-1-methyl-6-oxo-1,6-dihydropyridin-3-yl)phenyl]ethanesulfonamide;
N-benzyl-N-[4-(2,4-difluorophenoxy)-3-(4-ethoxy-1-methyl-6-oxo-1,6-dihydropyridin-3-yl)phenyl]ethanesulfonamide;
N-(2-chlorobenzyl)-N-[4-(2,4-difluorophenoxy)-3-(4-ethoxy-1-methyl-6-oxo-1,6-dihydropyridin-3-yl)phenyl]ethanesulfonamide;
N-[4-(2,4-difluorophenoxy)-3-(4-ethoxy-1-methyl-6-oxo-1,6-dihydropyridin-3-yl)phenyl]-N-(2-phenylethyl)ethanesulfonamide;
N-(cyclopropylmethyl)-N-[4-(2,4-difluorophenoxy)-3-(4-ethoxy-1-methyl-6-oxo-1,6-dihydropyridin-3-yl)phenyl]-1-phenylmethanesulfonamide;
N-benzyl-N-[4-(2,4-difluorophenoxy)-3-(4-ethoxy-1-methyl-6-oxo-1,6-dihydropyridin-3-yl)phenyl]-1-phenylmethanesulfonamide;
N-(2-chlorobenzyl)-N-[4-(2,4-difluorophenoxy)-3-(4-ethoxy-1-methyl-6-oxo-1,6-dihydropyridin-3-yl)phenyl]-1-phenylmethanesulfonamide;
N-[4-(2,4-difluorophenoxy)-3-(4-ethoxy-1-methyl-6-oxo-1,6-dihydropyridin-3-yl)phenyl]-1-phenyl-N-(2-phenylethyl)methanesulfonamide;
N-[2-(2-chlorophenyl)ethyl]-N-[4-(2,4-difluorophenoxy)-3-(4-ethoxy-1-methyl-6-oxo-1,6-dihydropyridin-3-yl)phenyl]ethanesulfonamide;
N-[4-(2,4-difluorophenoxy)-3-(4-ethoxy-1-methyl-6-oxo-1,6-dihydropyridin-3-yl)phenyl]-2-(3-phenyl-1H-pyrazol-1-yl)acetamide;
2-(5-chloro-2-fluorophenyl)-N-[4-(2,4-difluorophenoxy)-3-(4-ethoxy-1-methyl-6-oxo-1,6-dihydropyridin-3-yl)phenyl]acetamide;
N-[4-(2,4-difluorophenoxy)-3-(4-ethoxy-1-methyl-6-oxo-1,6-dihydropyridin-3-yl)phenyl]-2-(2-methyl-1,3-thiazol-4-yl)acetamide;
N-[4-(2,4-difluorophenoxy)-3-(4-ethoxy-1-methyl-6-oxo-1,6-dihydropyridin-3-yl)phenyl]-2-(1H-pyrazol-1-yl)acetamide;
N-[4-(2,4-difluorophenoxy)-3-(4-ethoxy-1-methyl-6-oxo-1,6-dihydropyridin-3-yl)phenyl]-2-(pyrimidin-5-yl)acetamide;
N-[4-(2,4-difluorophenoxy)-3-(4-ethoxy-1-methyl-6-oxo-1,6-dihydropyridin-3-yl)phenyl]-2-(3,5-dimethyl-1H-pyrazol-1-yl)acetamide;
N-[4-(2,4-difluorophenoxy)-3-(4-ethoxy-1-methyl-6-oxo-1,6-dihydropyridin-3-yl)phenyl]-2-(1H-1,2,4-triazol-1-yl)acetamide;
N-[4-(2,4-difluorophenoxy)-3-(4-ethoxy-1-methyl-6-oxo-1,6-dihydropyridin-3-yl)phenyl]-2-(pyrazin-2-yl)acetamide;
N-[2-(2-chlorophenyl)ethyl]-N-[4-(2,4-difluorophenoxy)-3-(4-ethoxy-1-methyl-6-oxo-1,6-dihydropyridin-3-yl)phenyl]-1-phenylmethanesulfonamide;
N-[4-(2,4-difluorophenoxy)-3-(4-ethoxy-1-methyl-6-oxo-1,6-dihydropyridin-3-yl)phenyl]-1-phenyl-N-(1,3-thiazol-2-ylmethyl)methanesulfonamide;
N-[4-(2,4-difluorophenoxy)-3-(4-ethoxy-1-methyl-6-oxo-1,6-dihydropyridin-3-yl)phenyl]-N-(pyridin-3-ylmethyl)ethanesulfonamide;
N-[4-(2,4-difluorophenoxy)-3-(4-ethoxy-1-methyl-6-oxo-1,6-dihydropyridin-3-yl)phenyl]-1-phenyl-N-(pyridin-3-ylmethyl)methanesulfonamide;
N-[4-(2,4-difluorophenoxy)-3-(4-ethoxy-1-methyl-6-oxo-1,6-dihydropyridin-3-yl)phenyl]-N-(pyrimidin-5-ylmethyl)ethanesulfonamide;
N-[4-(2,4-difluorophenoxy)-3-(4-ethoxy-1-methyl-6-oxo-1,6-dihydropyridin-3-yl)phenyl]-1-phenyl-N-(pyrimidin-5-ylmethyl)methanesulfonamide;
N-[4-(2,4-difluorophenoxy)-3-(4-ethoxy-1-methyl-6-oxo-1,6-dihydropyridin-3-yl)phenyl]-N-(pyrazin-2-ylmethyl)ethanesulfonamide;
N-[4-(2,4-difluorophenoxy)-3-(4-ethoxy-1-methyl-6-oxo-1,6-dihydropyridin-3-yl)phenyl]-1-phenyl-N-(pyrazin-2-ylmethyl)methanesulfonamide;
N-[4-(2,4-difluorophenoxy)-3-(4-ethoxy-1-methyl-6-oxo-1,6-dihydropyridin-3-yl)phenyl]-N-[(1-methyl-1H-pyrazol-4-yl)methyl]ethanesulfonamide;
N-[4-(2,4-difluorophenoxy)-3-(4-ethoxy-1-methyl-6-oxo-1,6-dihydropyridin-3-yl)phenyl]-N-[(1-methyl-1H-pyrazol-4-yl)methyl]-1-phenylmethanesulfonamide;
N-[4-(2,4-difluorophenoxy)-3-(4-ethoxy-1-methyl-6-oxo-1,6-dihydropyridin-3-yl)phenyl]-N-(1,3-thiazol-2-ylmethyl)ethanesulfonamide;
N-[4-(2,4-difluorophenoxy)-3-(4-ethoxy-1-methyl-6-oxo-1,6-dihydropyridin-3-yl)phenyl]-N-[(1-methyl-1H-imidazol-4-yl)methyl]ethanesulfonamide;
N-[4-(2,4-difluorophenoxy)-3-(4-ethoxy-1-methyl-6-oxo-1,6-dihydropyridin-3-yl)phenyl]-N-[(1-methyl-1H-imidazol-4-yl)methyl]-1-phenylmethanesulfonamide;
N-[4-(2,4-difluorophenoxy)-3-(4-ethoxy-1-methyl-6-oxo-1,6-dihydropyridin-3-yl)phenyl]-N-[(2S)-1,4-dioxan-2-ylmethyl]ethanesulfonamide;
N-[4-(2,4-difluorophenoxy)-3-(4-ethoxy-1-methyl-6-oxo-1,6-dihydropyridin-3-yl)phenyl]-N-(tetrahydro-2H-pyran-4-ylmethyl)ethanesulfonamide; and
N-[4-(2,4-difluorophenoxy)-3-(4-ethoxy-1-methyl-6-oxo-1,6-dihydropyridin-3-yl)phenyl]-N-[2-(tetrahydro-2H-pyran-4-yl)ethyl]ethanesulfonamide.

7. The method of claim 6, wherein the compound of formula (I) or the pharmaceutically acceptable salt thereof is N-(cyclopropylmethyl)-N-[4-(2,4-difluorophenoxy)-3-(4-ethoxy-1-methyl-6-oxo-1,6-dihydropyridin-3-yl)phenyl]ethanesulfonamide.

8. The method of claim 1, wherein the cancer is prostate cancer.

9. The method of claim 1, wherein the cancer is acute myelocytic leukemia.

10. The method of claim 2, wherein the cancer is prostate cancer.

11. The method of claim 2, wherein the cancer is acute myelocytic leukemia.

12. The method of claim 3, wherein the cancer is prostate cancer.

13. The method of claim 3, wherein the cancer is acute myelocytic leukemia.

14. The method of claim 4, wherein the cancer is prostate cancer.

15. The method of claim 4, wherein the cancer is acute myelocytic leukemia.

16. The method of claim 5, wherein the cancer is prostate cancer.

17. The method of claim 5, wherein the cancer is acute myelocytic leukemia.

18. The method of claim 6, wherein the cancer is prostate cancer.

19. The method of claim 6, wherein the cancer is acute myelocytic leukemia.

20. The method of claim 7, wherein the cancer is prostate cancer.

21. The method of claim 7, wherein the cancer is acute myelocytic leukemia.

* * * * *